US012697128B2

(12) United States Patent
Sauer et al.

(10) Patent No.: US 12,697,128 B2
(45) Date of Patent: Aug. 4, 2026

(54) ATRIAL CLIP ASSEMBLY AND DELIVERY DEVICE

(71) Applicant: LSI Solutions, Inc., Victor, NY (US)

(72) Inventors: Jude S. Sauer, Pittsford, NY (US); Benjamin James Boseck, Rochester, NY (US); Matthew Wrona, Fairport, NY (US); Michael W. Fitzsimmons, Rochester, NY (US)

(73) Assignee: LSI Solutions, Inc., Victor, NY (US)

( * ) Notice: Subject to any disclaimer, the term of this patent is extended or adjusted under 35 U.S.C. 154(b) by 0 days.

(21) Appl. No.: 18/612,814

(22) Filed: Mar. 21, 2024

(65) Prior Publication Data

US 2024/0415515 A1     Dec. 19, 2024

Related U.S. Application Data

(60) Provisional application No. 63/624,988, filed on Jan. 25, 2024, provisional application No. 63/527,438, filed on Jul. 18, 2023, provisional application No. 63/467,747, filed on May 19, 2023, provisional application No. 63/453,976, filed on Mar. 22, 2023.

(51) Int. Cl.
*A61B 17/122* (2006.01)
(52) U.S. Cl.
CPC .................................. *A61B 17/122* (2013.01)
(58) Field of Classification Search
CPC ............ A61B 17/12122; A61B 17/122; A61B 17/1227; A61B 17/1285; A61B 2017/00243; A61B 2017/00309
See application file for complete search history.

(56) References Cited

U.S. PATENT DOCUMENTS

| 6,488,689 B1 | 12/2002 | Kaplan et al. |
| 7,951,147 B2 | 5/2011 | Privitera et al. |
| 8,663,245 B2 | 3/2014 | Francischelli et al. |
| 8,814,778 B2 | 8/2014 | Kiser et al. |

(Continued)

FOREIGN PATENT DOCUMENTS

| WO | 2017204879 | 2/2017 |
| WO | 2022109475 | 5/2022 |
| WO | 2023014925 | 2/2023 |

OTHER PUBLICATIONS

International Search Report and Written Opinion for International Application No. PCT/US2024/021041, filed Mar. 22, 2024, mailed Aug. 6, 2024, 9 pages.

*Primary Examiner* — Ryan J. Severson
(74) *Attorney, Agent, or Firm* — Michael E. Coyne

(57)     ABSTRACT

An atrial clip assembly includes a first arm assembly having a first arm body that includes a first support portion, and a first spine portion, with a first portion of the first spine portion extending along and within a corresponding first portion of the first support portion. The first arm assembly further includes a first suture, wherein a first portion of the first suture is disposed around the first portion of the first spine portion, and wherein a second portion of the first suture extends external to the first support portion. The atrial clip assembly also includes a second arm assembly including a second arm body that includes a second support portion. The atrial clip assembly further includes a hinge portion coupling a first end of the first arm body to a first end of the second arm body, the hinge portion being flexible.

11 Claims, 69 Drawing Sheets

(56)                    References Cited

U.S. PATENT DOCUMENTS

| | | | |
|---|---|---|---|
| 9,393,023 | B2 | 7/2016 | Privitera et al. |
| 9,408,659 | B2 | 8/2016 | Privitera et al. |
| 9,463,024 | B2 | 10/2016 | Kiser et al. |
| 9,724,105 | B2 | 8/2017 | Kaplan et al. |
| 9,848,898 | B2 | 12/2017 | Friedman et al. |
| 9,888,925 | B2 | 2/2018 | Bertolero et al. |
| 9,901,351 | B2 | 2/2018 | Winkler et al. |
| 9,901,352 | B2 | 2/2018 | Fago et al. |
| 10,166,024 | B2 | 1/2019 | Williamson, IV et al. |
| 10,182,824 | B2 | 1/2019 | Monti et al. |
| 10,201,352 | B2 | 2/2019 | Fago et al. |
| 10,278,704 | B2 | 5/2019 | Kiser et al. |
| 10,285,712 | B2 | 5/2019 | Cosgrove, III et al. |
| 10,314,585 | B2 | 6/2019 | Williamson, IV et al. |
| 10,433,854 | B2 | 10/2019 | Miller et al. |
| 10,456,141 | B2 | 10/2019 | Armenteros et al. |
| 10,524,791 | B2 | 1/2020 | Bertolero et al. |

| | | | |
|---|---|---|---|
| 10,869,668 | B2 | 12/2020 | Privitera et al. |
| 10,898,204 | B2 | 1/2021 | Winkler et al. |
| 10,925,615 | B2 | 2/2021 | Deville et al. |
| 11,191,547 | B2 | 12/2021 | Deville et al. |
| 11,266,413 | B2 | 3/2022 | Winkler et al. |
| 11,389,175 | B2 | 7/2022 | Fago et al. |
| 11,471,161 | B2 | 10/2022 | Hughett, Sr. et al. |
| 12,564,411 | B2 | 3/2026 | Mata et al. |
| 2008/0033457 | A1* | 2/2008 | Franischelli ..... A61B 17/1285 |
| | | | 606/157 |
| 2008/0039879 | A1 | 2/2008 | Chin et al. |
| 2008/0208324 | A1 | 8/2008 | Glithero et al. |
| 2009/0209986 | A1 | 8/2009 | Stewart et al. |
| 2018/0199944 | A1* | 7/2018 | Hughett, Sr. ...... A61B 17/1227 |
| 2019/0314025 | A1 | 10/2019 | Patel et al. |
| 2021/0196279 | A1 | 7/2021 | Foshee et al. |
| 2021/0267603 | A1 | 9/2021 | Foshee et al. |
| 2024/0382210 | A1* | 11/2024 | Sauer, Md ........... A61B 17/122 |
| 2024/0415515 | A1* | 12/2024 | Sauer, Md ......... A61B 17/1285 |

* cited by examiner

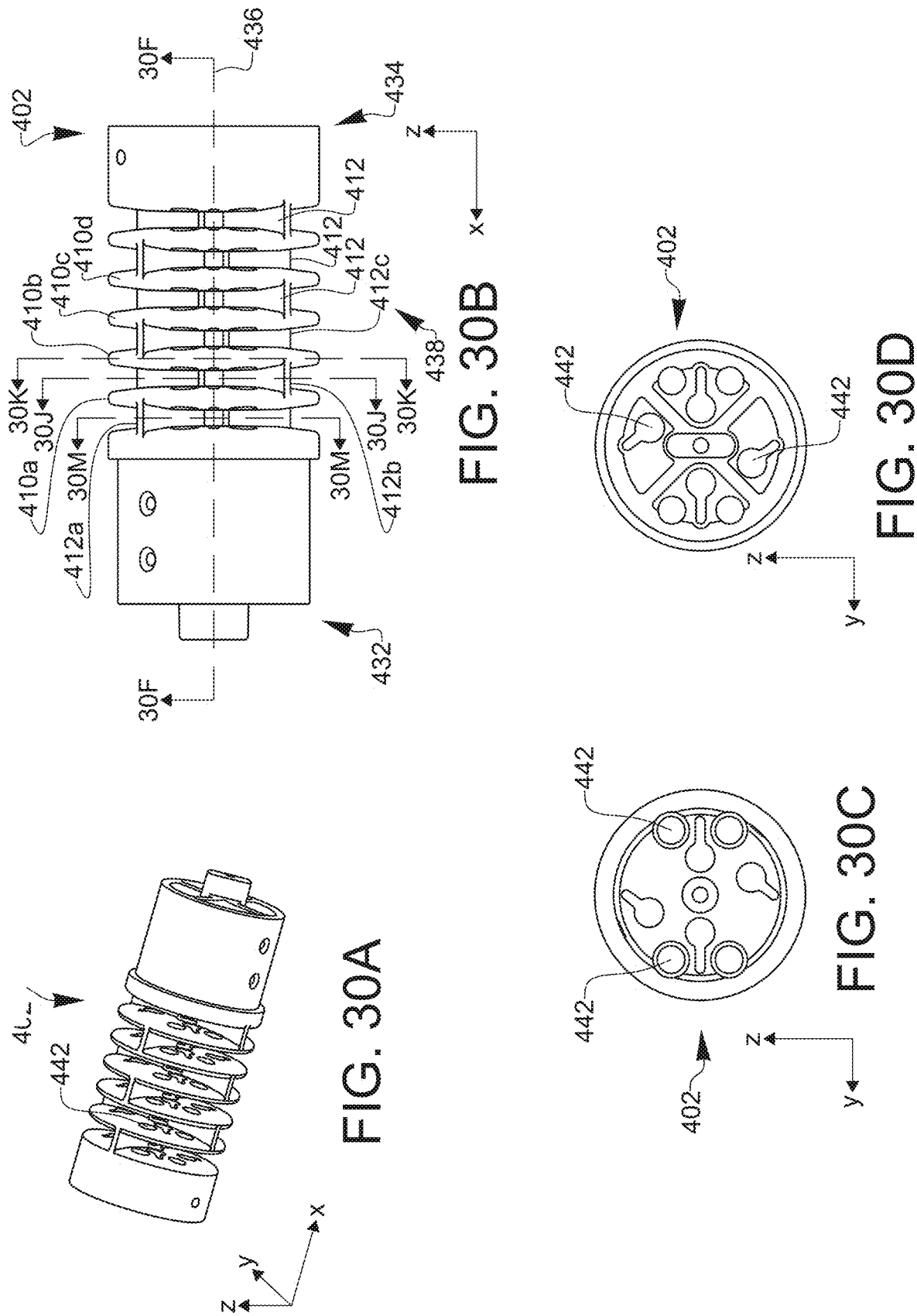

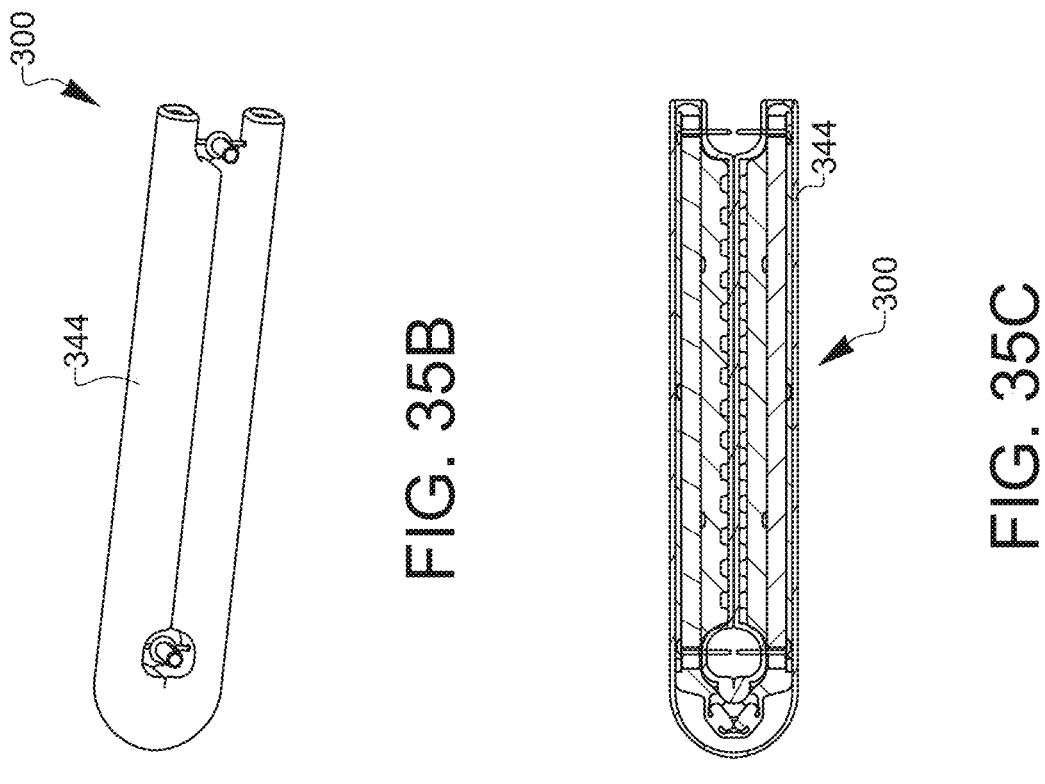
FIG. 35B
FIG. 35C
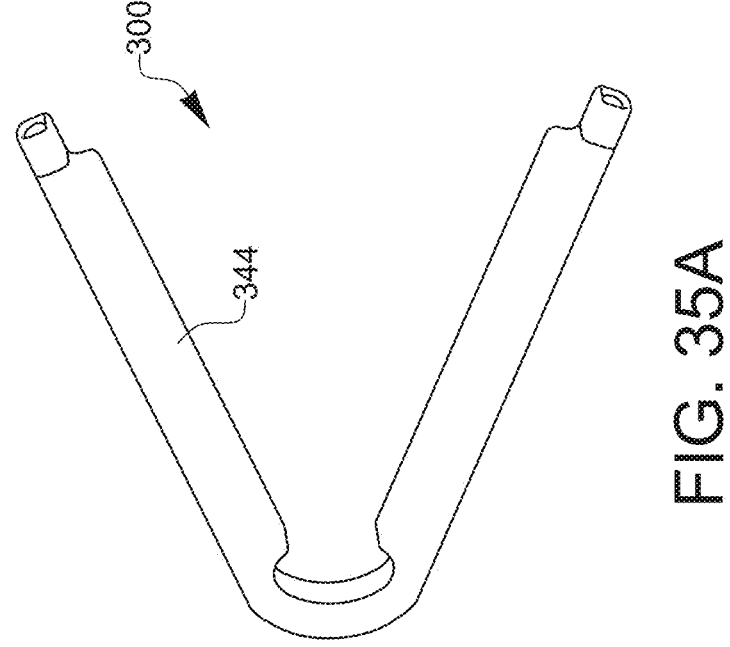
FIG. 35A

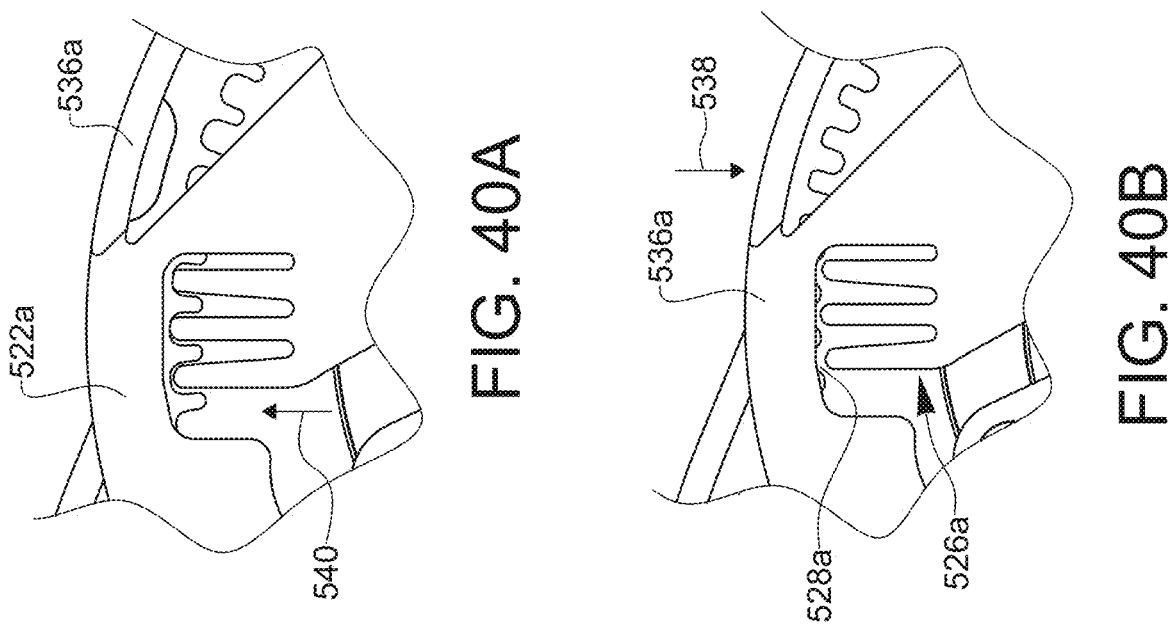
FIG. 40A
FIG. 40B
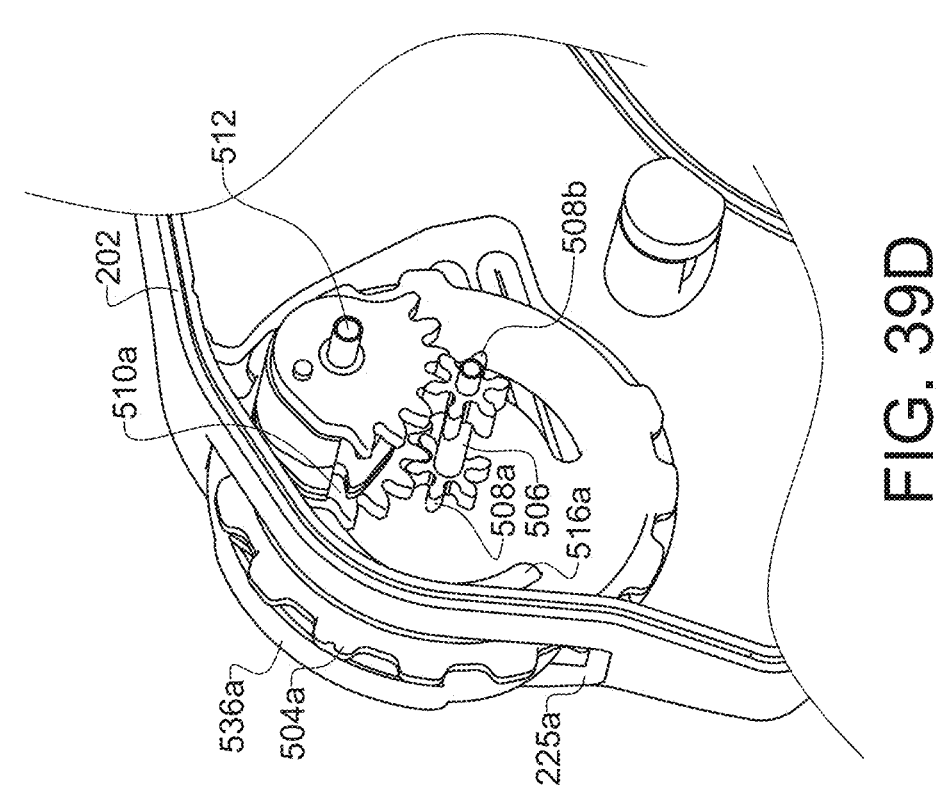
FIG. 39D

ATRIAL CLIP ASSEMBLY AND DELIVERY DEVICE

CROSS-REFERENCE TO RELATED APPLICATIONS

This application claims the benefit of each of U.S. Provisional Patent Application No. 63/453,976, filed Mar. 22, 2023, U.S. Provisional Patent Application No. 63/467,747, filed May 19, 2023, U.S. Provisional Patent Application No. 63/527,438, filed Jul. 18, 2023, and U.S. Provisional Patent Application No. 63/624,988, filed Jan. 25, 2024, the contents of each which is hereby incorporated by reference in its entirety.

FIELD OF THE INVENTION

The claimed invention relates to surgical devices, and more specifically to an atrial clip assembly and a delivery device for the atrial clip assembly.

BACKGROUND

Atrial fibrillation ("AF") is a common cardiac arrhythmia affecting millions of people and is associated with ischemic stroke. AF leads to insufficient contraction of the left atrium, lowered endurance, and irregular heartrate. The inactivity of sufficient blood flow within the left atrium leads to hypercoagulability and thus to an increased risk for thrombus formation.

Left atrial appendage ("LAA") thrombosis and embolization is recognized as the principal mechanism of stroke related to AF. This stroke mechanism can be correlated with reduced LAA flow velocity, thrombus formation, hypertension, and atheromatous disease of the aorta. The LAA is an accessory chamber of the heart that fills and empties in response to both ventricular and atrial dynamics. Variable morphology of the LAA with respect to shape, volume, length, and width, specifically, larger LAA volume, depth, and number of lobes may be related to likelihood of thrombus formation. At present, pharmacological based anticoagulation therapy, particularly with warfarin, is recognized as a highly effective treatment for medical management of patients with AF. While highly effective, warfarin use has a narrow therapeutic range and is associated with a potential risk of major hemorrhage and pharmacological contraindications. When these risks or other impediments to anticoagulation outweigh the risk of stroke related to AF, removing or isolating the LAA may be an attractive alternative approach for the prevention of embolic events.

Occluding the LAA from communication with the left atrium at the time of other cardiac surgery is a common means of isolating the LAA. The LAA can be occluded surgically by ligation, plication, or amputation, a procedure which can be performed routinely in patients as an adjunct to heart valve surgery. Transvenous occlusion of the LAA is also a known approach in preventing embolism in patients with AF, utilizing catheter deployment of an implantable device to seal the mouth of the LAA. Percutaneous LAA occlusion is another known approach for occluding the LAA from blood flow and thus preventing thrombus formation and subsequent thromboembolic complications. The advantages of the percutaneous LAA occlusion technique include a less invasive procedure, a faster recovery as compared with surgical ligation, and the reduced risk of potential bleeding in the absence of anticoagulation therapy. However, occlusion of the LAA remains challenging. While novel approaches to LAA occlusion have been developed, they can be more complex and may potentially have increased risks of LAA injury, incomplete occlusion, and device dislocation.

BRIEF DESCRIPTION OF THE DRAWINGS

FIGS. 9A to 11 and 33A to 34B are various views of an embodiment of an atrial clip assembly;

FIGS. 14 to 29, 31A, 31B, 32A to 32D, 33A to 33D, 34A to 34B, and 35A to 35C illustrate various views of further embodiments of an introducer device for the atrial clip assembly;

FIGS. 30A to 30M illustrate various views of an embodiment of the flexible coupling of the introducer device of FIGS. 14 to 29;

FIGS. 38A to 43C are various views of an embodiment of a first adjustment assembly and a second adjustment assembly;

DETAILED DESCRIPTION OF THE INVENTION

Figures 1A, 1B, 1C:
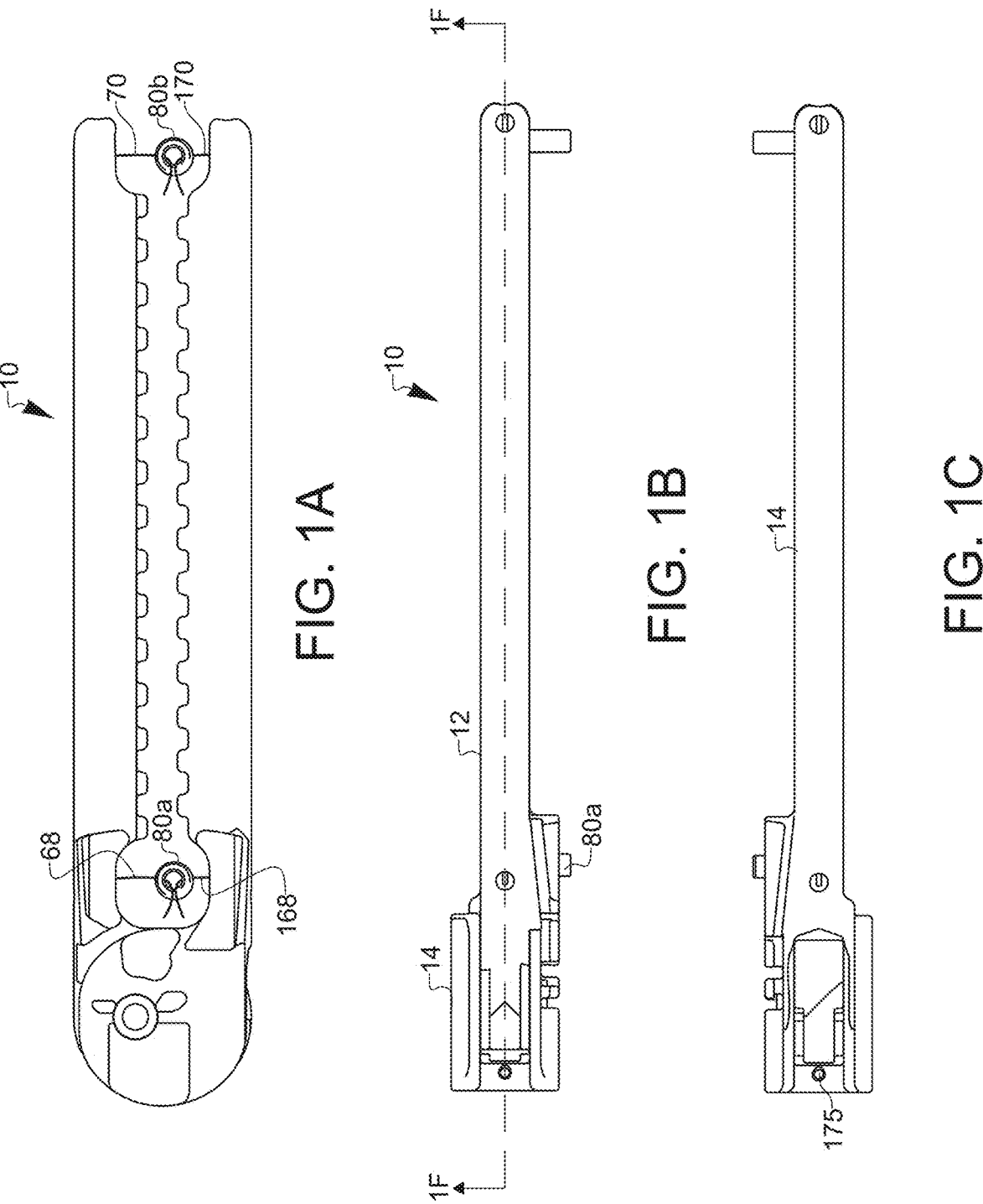
FIGS. 1A to 1H are various views of an embodiment of an atrial clip assembly.
Figures 1D, 1E:
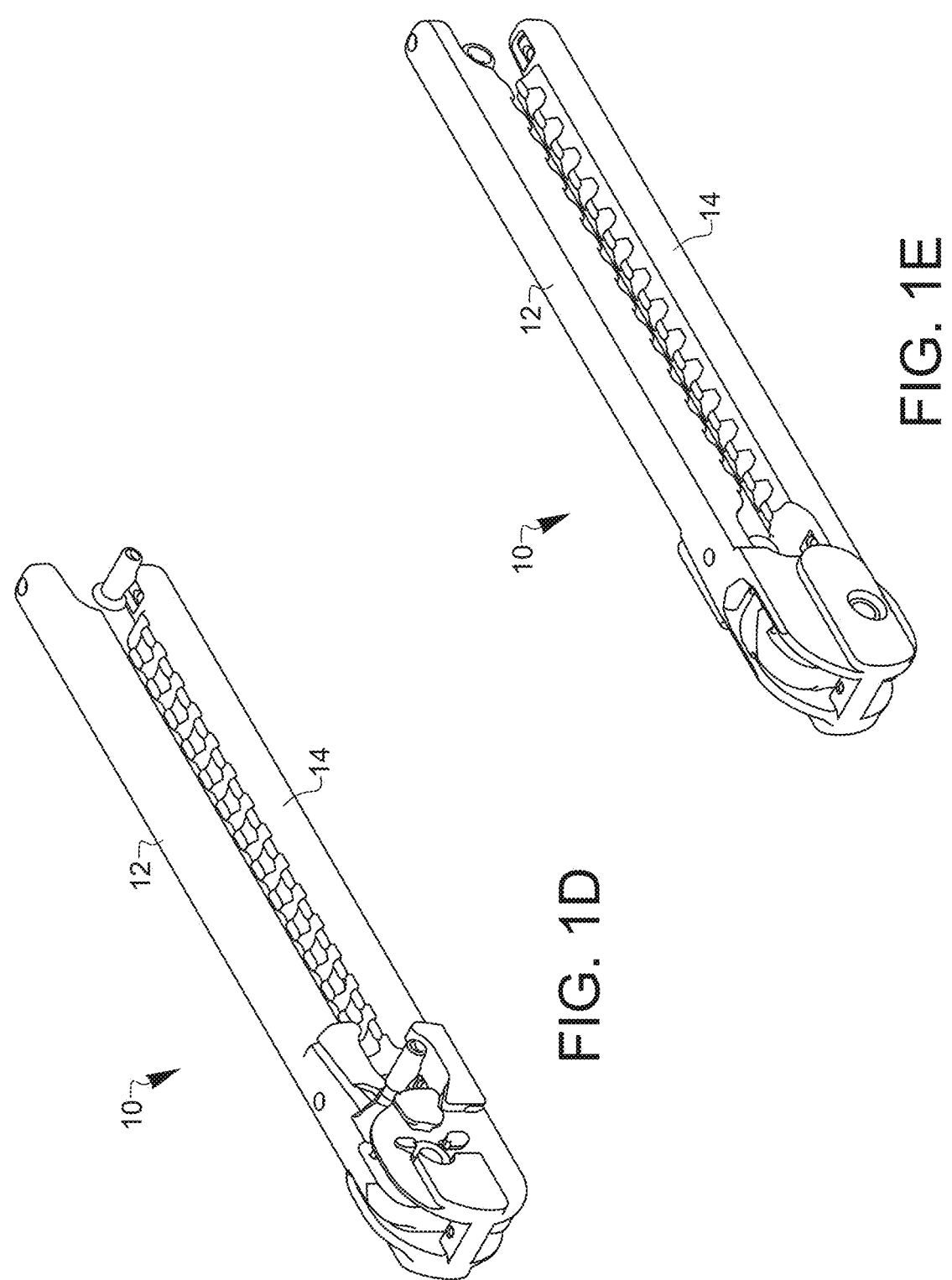

As illustrated in FIGS. 1A to 1H, an embodiment of an atrial clip assembly 10 includes a first arm assembly 12 coupled to a second arm assembly 14. The first arm assembly 12 may be coupled to the second arm assembly 14 in any suitable manner, such as pivotably coupled to the second arm assembly 14, and in some embodiments, pivotably and displaceably coupled to the second arm assembly 14. The atrial clip assembly 10 may be configured to be applied to the left atrial appendage ("LAA") of a human heart, and a portion of the LAA may be placed between the first arm assembly 12 and the second arm assembly 14, and one or more portions of suture may be coupled to each of the first arm assembly 12 and the second arm assembly 14 to secure the first arm assembly 12 and the second arm assembly 14 in a position constricting a portion of the LAA.

The first arm assembly 12 may include a first arm body 16, which is illustrated in FIGS. 4A to 4E. The first arm body 16 may be elongated and may extend from a first end 18 to a second end 20 along a first arm body axis 22. The first arm body 16 may also include a first support portion 24 that extends from a first end 26 to a second end 28 along the first arm body axis 22, and the first support portion 24 may extend from the second end 20 towards the first end 18 such that the first end 26 is disposed offset from the first end 18 of the first arm body 16. The first support portion 24 may have a rectangular or generally rectangular shape (e.g., cross-sectional shape) along all or a portion of the first arm body axis 22. A plurality of projections 30 may extend from an engagement surface 32 (e.g., a bottom surface) of the first support portion 24.

The first arm body 16 may also include a first coupling portion 34 disposed at the first end 18 of the first arm body 16, and the first coupling portion 34 may extend along a first coupling axis 36 that may be disposed at an angle between 30° and 90° to the first arm body axis 22. The first coupling portion 34 may be planar or substantially planar and may be defined by a first lateral surface 42 and a second lateral surface 44, and each of the surfaces 42, 44 may be parallel to the X-Z plane of the reference coordinate system of FIG. 4A. An elongated slot 40 may be formed through the first lateral surface 42 and the second lateral surface 44 of the first coupling portion 34 and may extend along the first coupling axis 36. A portion 38 of the first coupling portion 34 may be coupled to the first end 26 of the first support portion 24. A first notch edge portion 46 may extend along a portion of the first support portion 24 from the first end 26 towards the second end 28, and the first notch edge portion 46 may have a concave, arcuate, or semi-circular shape when viewed along the Y-axis of the reference coordinate system of FIGS. 4A and 4B. A second notch edge portion 48 may extend along a portion of the first support portion 24 from the second end 28 towards the first end 26, and the second notch edge portion 48 may have a concave, semi-concave, or semi-circular shape when viewed along the Y-axis of the reference coordinate system of FIGS. 4A and 4B. A support ledge 74 may be disposed along all or a portion of the portion 38, and the support ledge may extend from a lateral edge or lateral surface of the first support portion 24. An upper surface of the support ledge 74 may include a channel that is configured to support one or more portions of suture that may be used to secure the atrial clip assembly 10 in the closed position or to secure the atrial clip assembly 10 to the introducer device 200. The portion 38 of the first coupling portion 34 may be coupled to the first end 26 of the first support portion 24 in any suitable manner, and the first coupling portion 34 and the first support portion 24 may be integrally formed as a single, unitary part. The first arm body 16 may be injection molded as a single piece part, and may be made from or comprise a plastic material (for example, ABS or nylon).

Figure 1F:
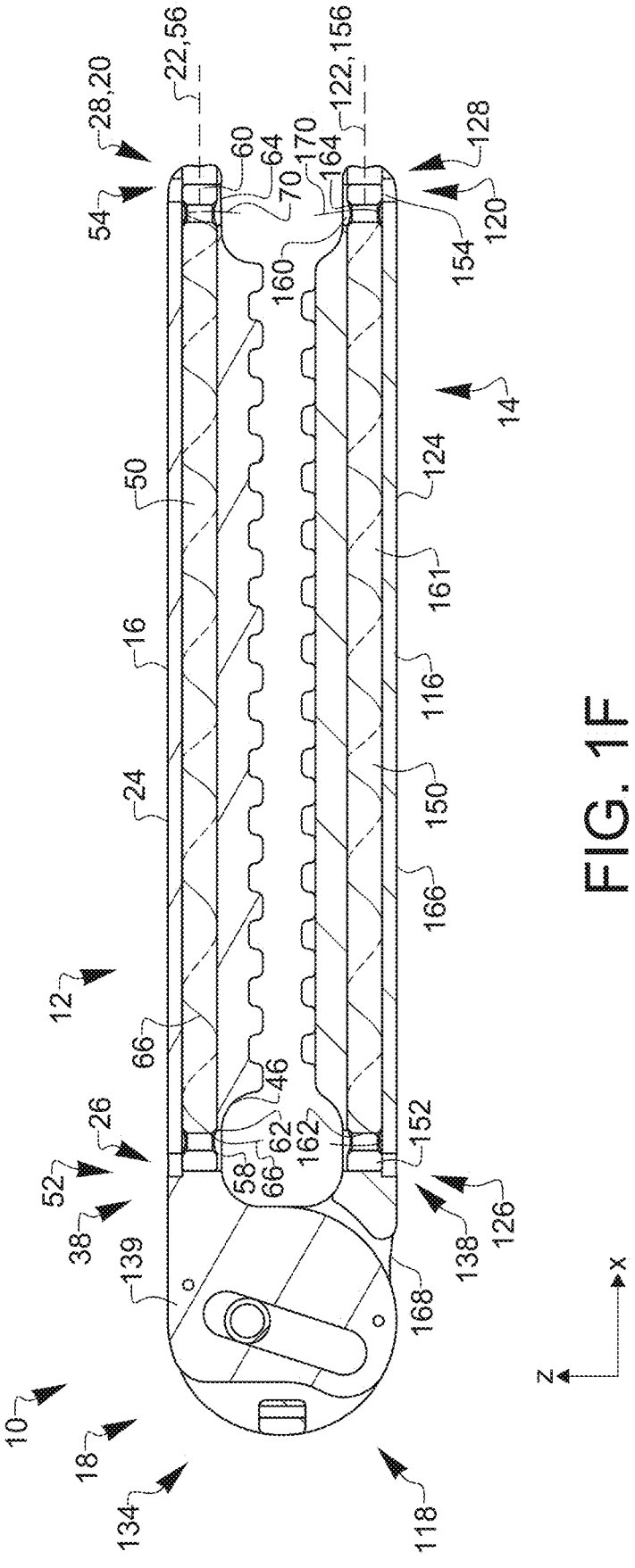
Figure 1G:
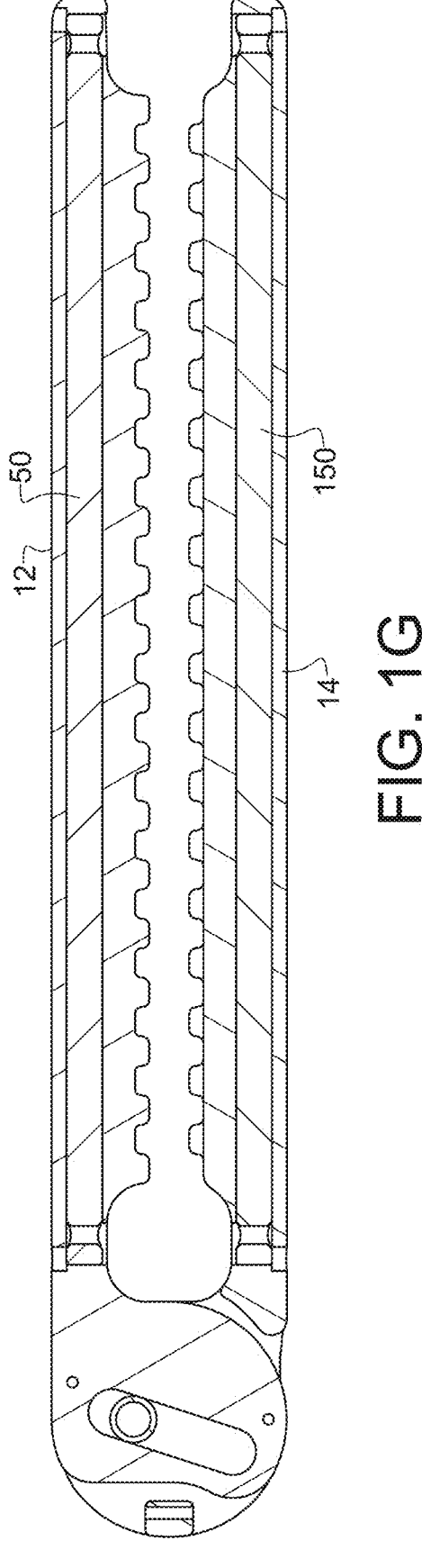
Figure 1H:
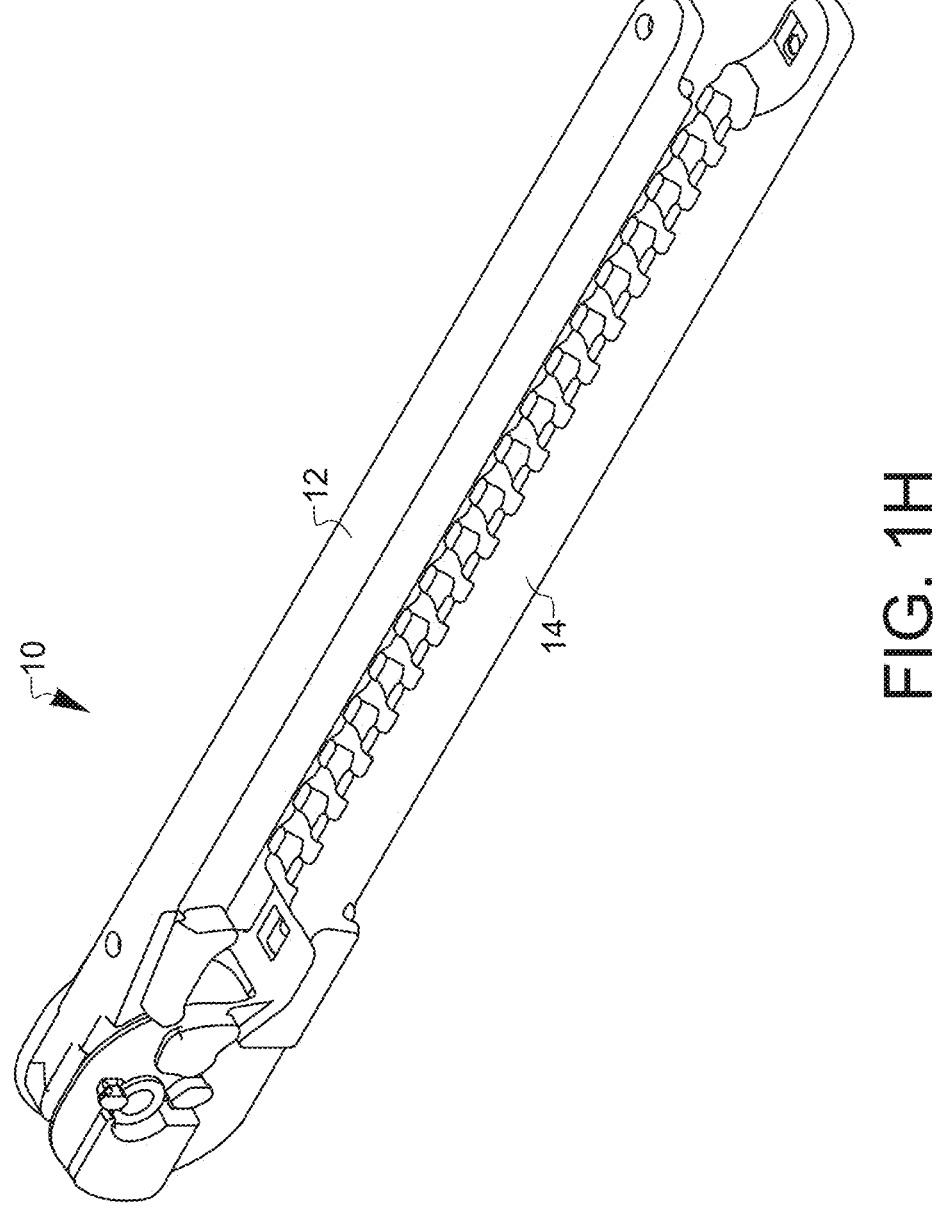
Figures 2A, 2B:
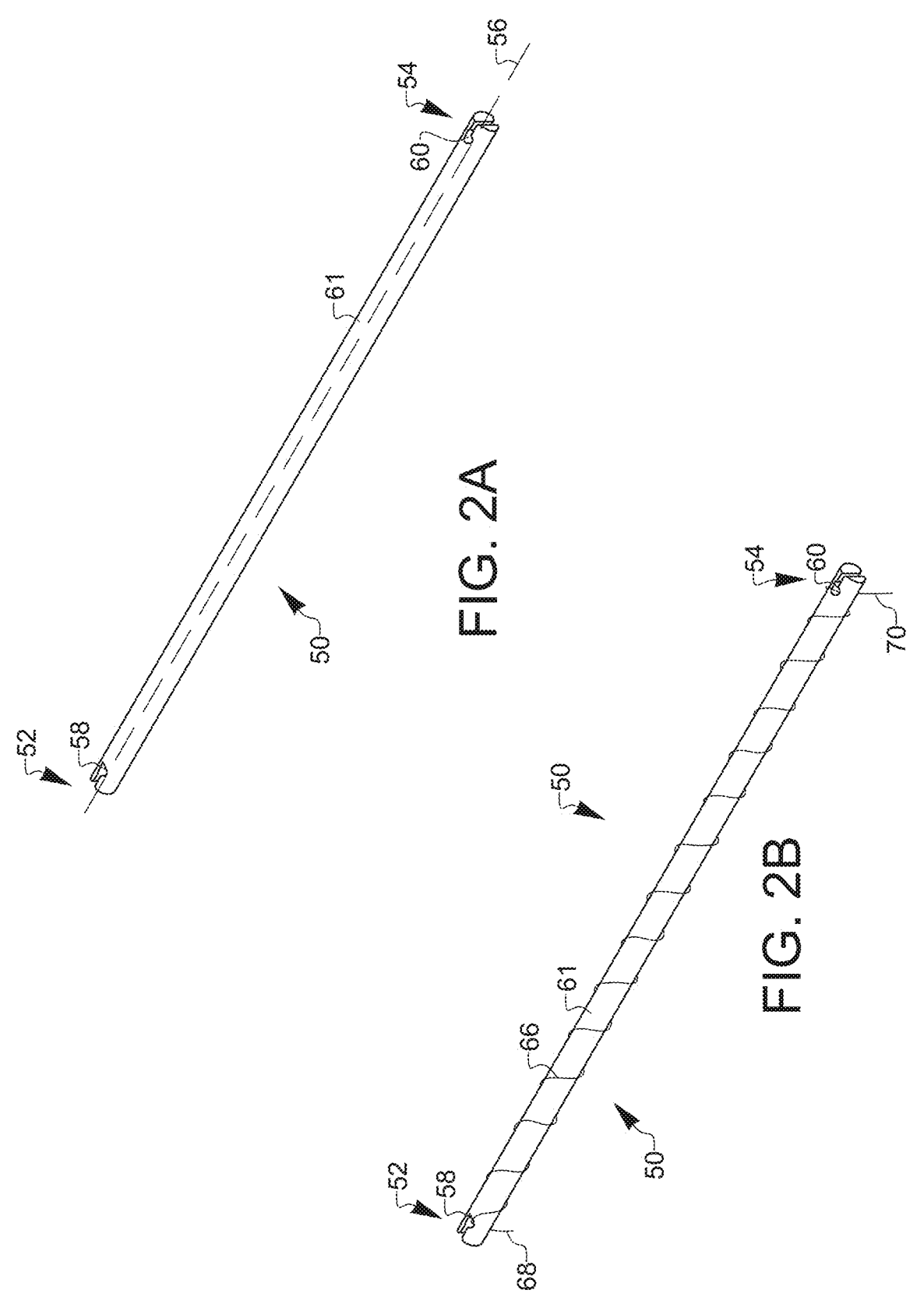
FIGS. 2A and 2B are perspective views of an embodiment of a first spine portion of the atrial clip assembly of FIGS. 1A to 1H.

As illustrated in the cross-sectional view of FIG. 1F, the first arm assembly 12 may also include a first spine portion 50 that extends along all or a portion of the first support portion 24 of the first arm body 16. The first spine portion 50 may be elongated and may extend from a first end 52 to a second end 54 along a first spine axis 56 that may be aligned with the first arm body axis 22. The first end 52 may be at or adjacent to (e.g., slightly offset from) the first end 26 of the first support portion 24, and the second end 54 may be at or adjacent to (e.g., slightly offset from) the second end 28 of the first support portion 24. The first spine portion 50 may have any suitable cross-sectional shape or combination of shapes. For example, as illustrated in FIG. 2A, the first spine portion 50 may have an exterior surface 61 having a cylindrical shape which may be uniform or substantially uniform from the first end 52 (or from a point adjacent to the first end 52) to the second end 54 (or to a point adjacent to the second end 54). The first spine portion 50 may have a first aperture 58 adjacent to the first end 52, and the first aperture 58 may extend along an axis that is normal to the first spine axis 56. The first spine portion 50 may also have a second aperture 60 adjacent to the second end 54, and the second aperture 60 may extend along an axis that is normal to the first spine axis 56.

The first spine portion 50 may be fabricated or made from or of a stiffer material than the first arm body 16, and the first spine portion 50 may be made from or comprise a metal material, such as titanium, steel, or aluminum, for example. The first spine portion 50 may be co-molded with the first arm body 16 in any suitable manner. For example, the first spine portion 50 may be placed in a mold used to form the first arm body 16, and the part of the first arm body 16 may be formed around to surround the first spine portion 50. As such, a first arm aperture 62 may be formed on a surface at least partially defining the first notch edge portion 46 of the first support portion 24 (e.g., in the first support portion 24 at or adjacent to the first end 26) and the first arm aperture 62 may be aligned with the first aperture 58 of the first spine portion 50. Further, a second farm aperture 64 may be formed on a surface at least partially defining the second notch edge portion 48 of the first support portion 24 (e.g., in the first support portion 24 at or adjacent to the second end 28) and the second arm aperture 64 may be aligned with second aperture 60 of the first spine portion 50.

In some embodiments of the atrial clip assembly 10, the first arm assembly 12 may also include one or more portions of suture 66 may be wrapped around the exterior surface 61 of the first spine portion 50 prior to molding the first support portion 24 over the first spine portion 50 such that the one or more portions of suture 66 disposed within the first support portion 24 are prevented from displacing relative to the first support portion 24 and are anchored by the first support portion 24. The one or more portions of suture 66 may be wrapped around the exterior surface 61 of the first spine portion 50 in any suitable manner, and the one or more portions of suture 66 may be wrapped around the exterior surface 61 of the first spine portion 50 in a helical manner, for example, as illustrated in FIG. 2B. After molding, a first end 68 of the one or more portions of suture 66 may extend through the first arm aperture 62 of the first support portion 24 and all or a portion of the first aperture 58 of the first spine portion 50. Also after molding, a second end 70 of the one or more portions of suture 66 may extend through the second arm aperture 64 of the first support portion 24 and all or a portion of the second aperture 60 of the first spine portion 50. The one or more portions of suture 66 may be any material or combination of materials capable of securing (or cooperating to secure) the first arm assembly 12 to the second arm assembly 14, as will be described in more detail below. As such, the one or more portions of suture 66 may be any suture, wire, thread, fabric, or cable, for example.

As illustrated in FIG. IF, the atrial clip assembly 10 also includes the second arm assembly 14. The second arm assembly 14 may include a second arm body 116, which is illustrated in FIGS. 3A to 3F. The second arm body 116 may be elongated and may extend from a first end 118 to a second end 120 along a second arm body axis 122. The second arm assembly 14 may also include a second support portion 124 that extends from a first end 126 to a second end 128 along the second arm body axis 122, and the second support portion 124 may extend from the second end 120 towards the first end 118 such that the first end 126 is disposed offset from the first end 118 of the second arm body 116. The second support portion 124 may have a rectangular or generally rectangular shape (e.g., cross-sectional shape) along all or a portion of the second arm body axis 122. A plurality of projections 130 may extend from an engagement surface 132 (e.g., a top surface) of the second support portion 124. The engagement surface 132 of the second support portion 124 may be configured to be opposed to (i.e., facing) the engagement surface 32 of the first support portion 24 when the first arm assembly 12 and second arm assembly 14 is in an engaged position (or when the atrial clip assembly 10 is in an engaged position). As such, one or more of the plurality of projections 30 of the first arm assembly 12 and one or more of the plurality of projections 130 of the second arm assembly 14 are configured to engage portions of the LAA to ensure a tight grip on the LAA.

Figures 3A, 3B:
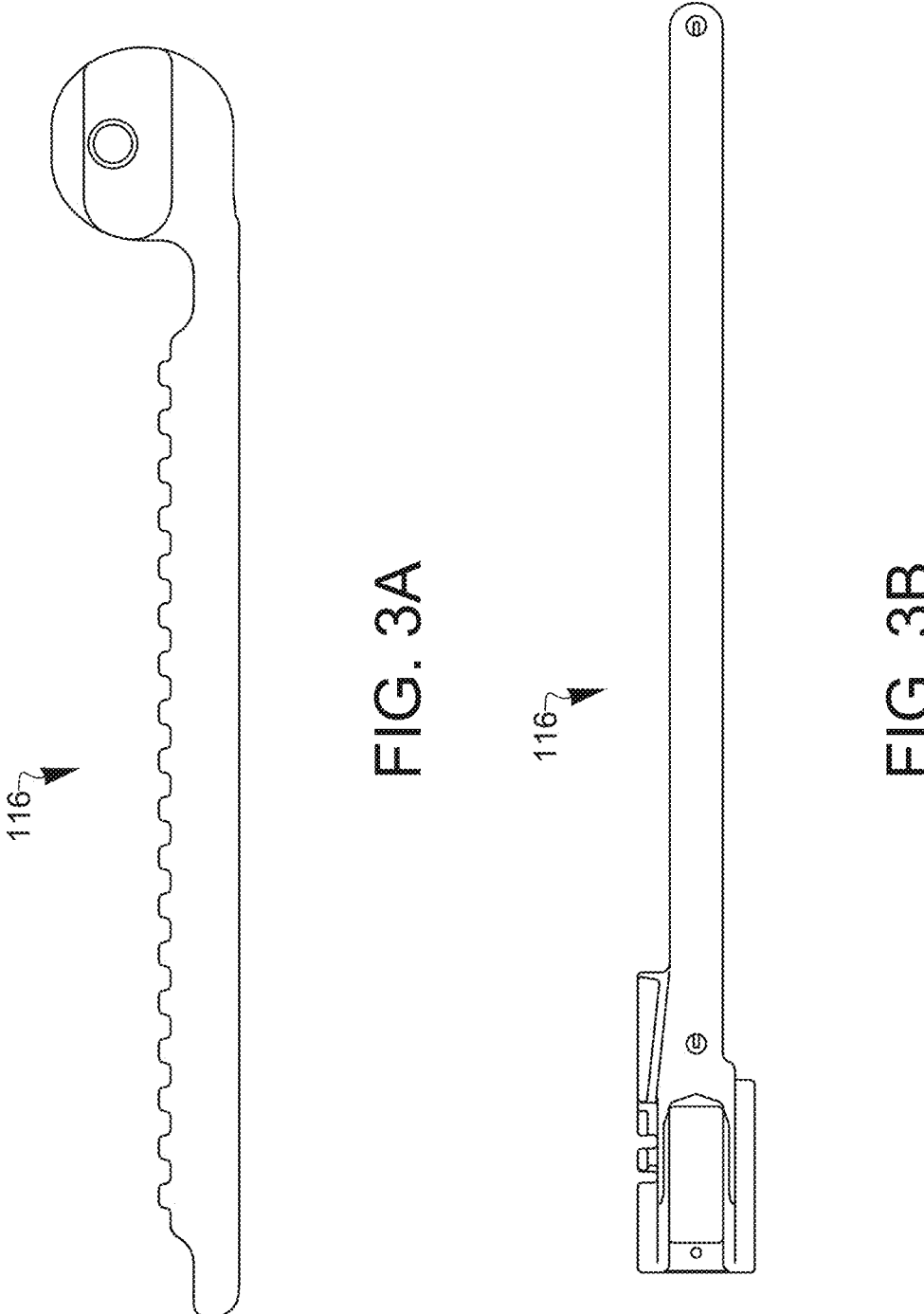
FIGS. 3A and 3F are various views of an embodiment of a second arm body of the atrial clip assembly of FIGS. 1A to 1H.
Figures 3C, 3D:
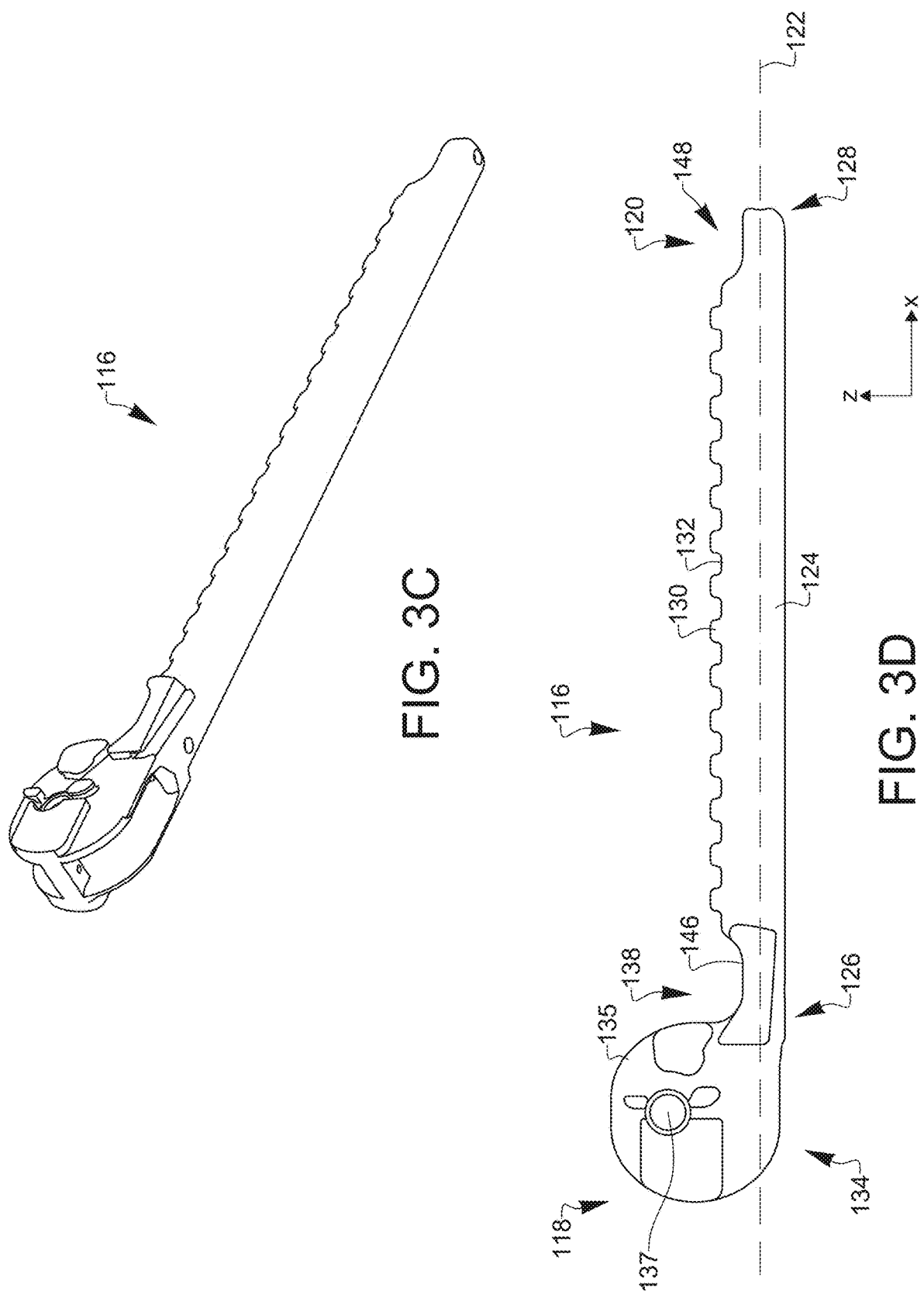
Figures 3E, 3F:
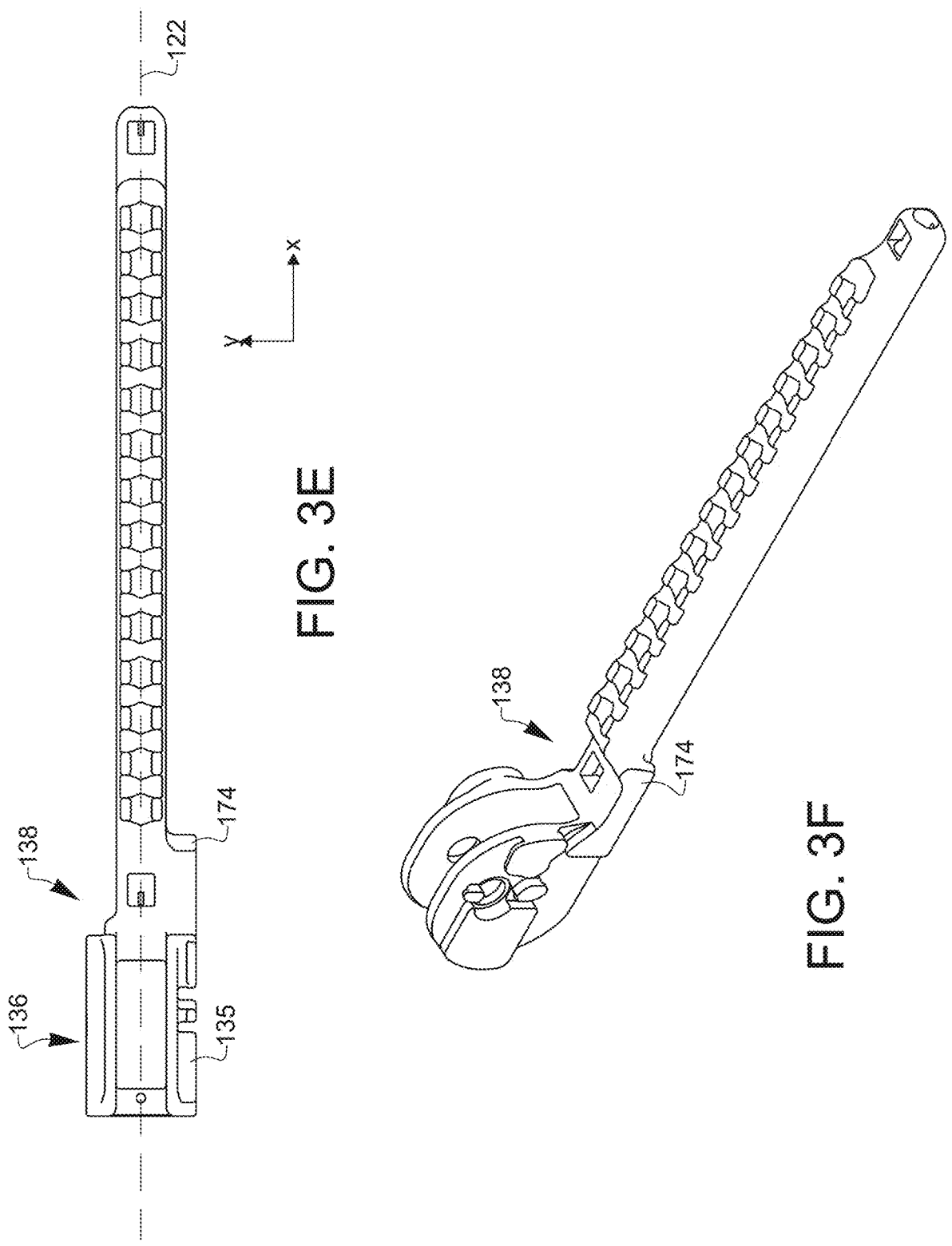
Figures 4A, 4B, 4C:
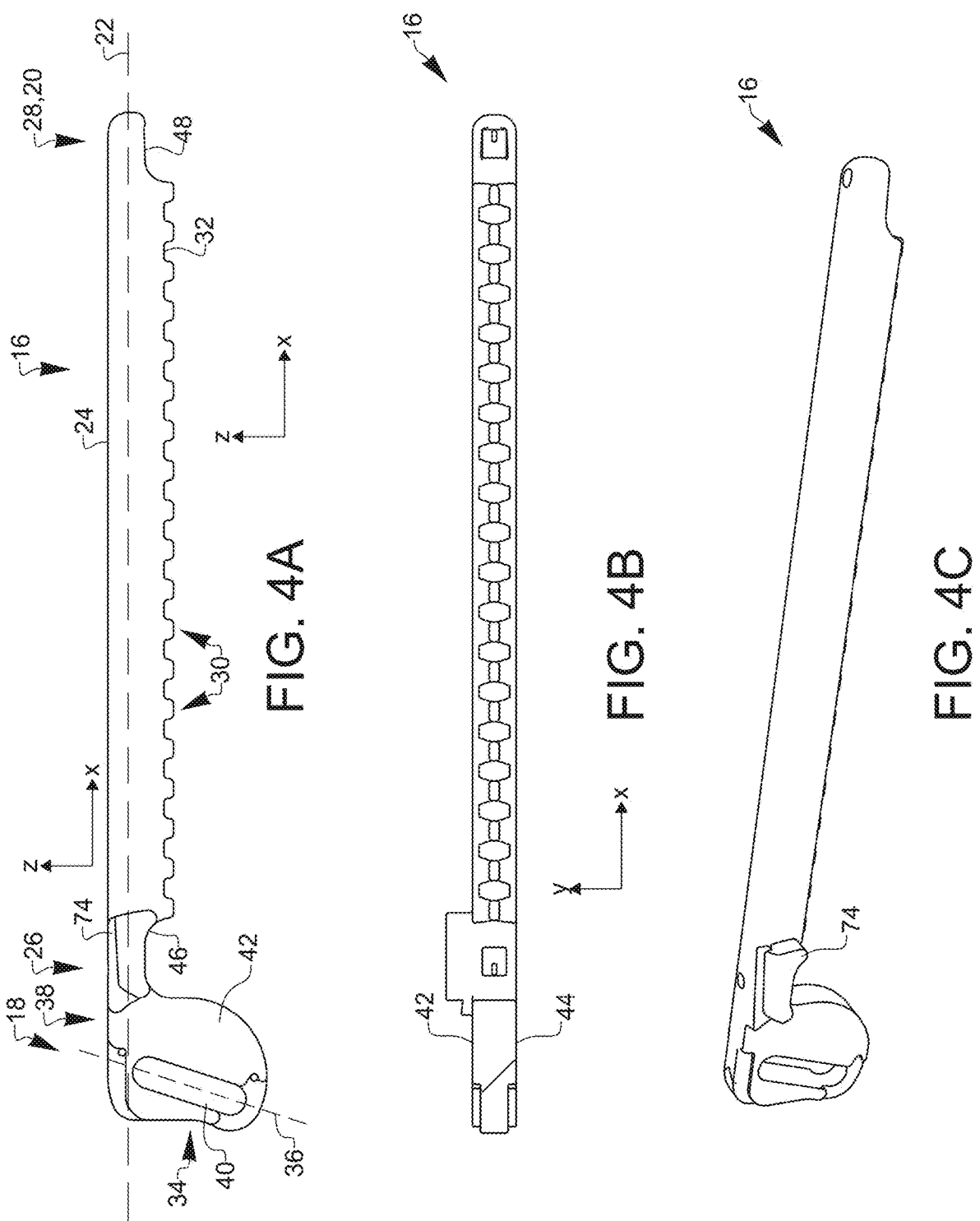
FIGS. 4A and 4E are various views of an embodiment of a first arm body of the atrial clip assembly of FIGS. 1A to 1H.
Figures 4D, 4E:
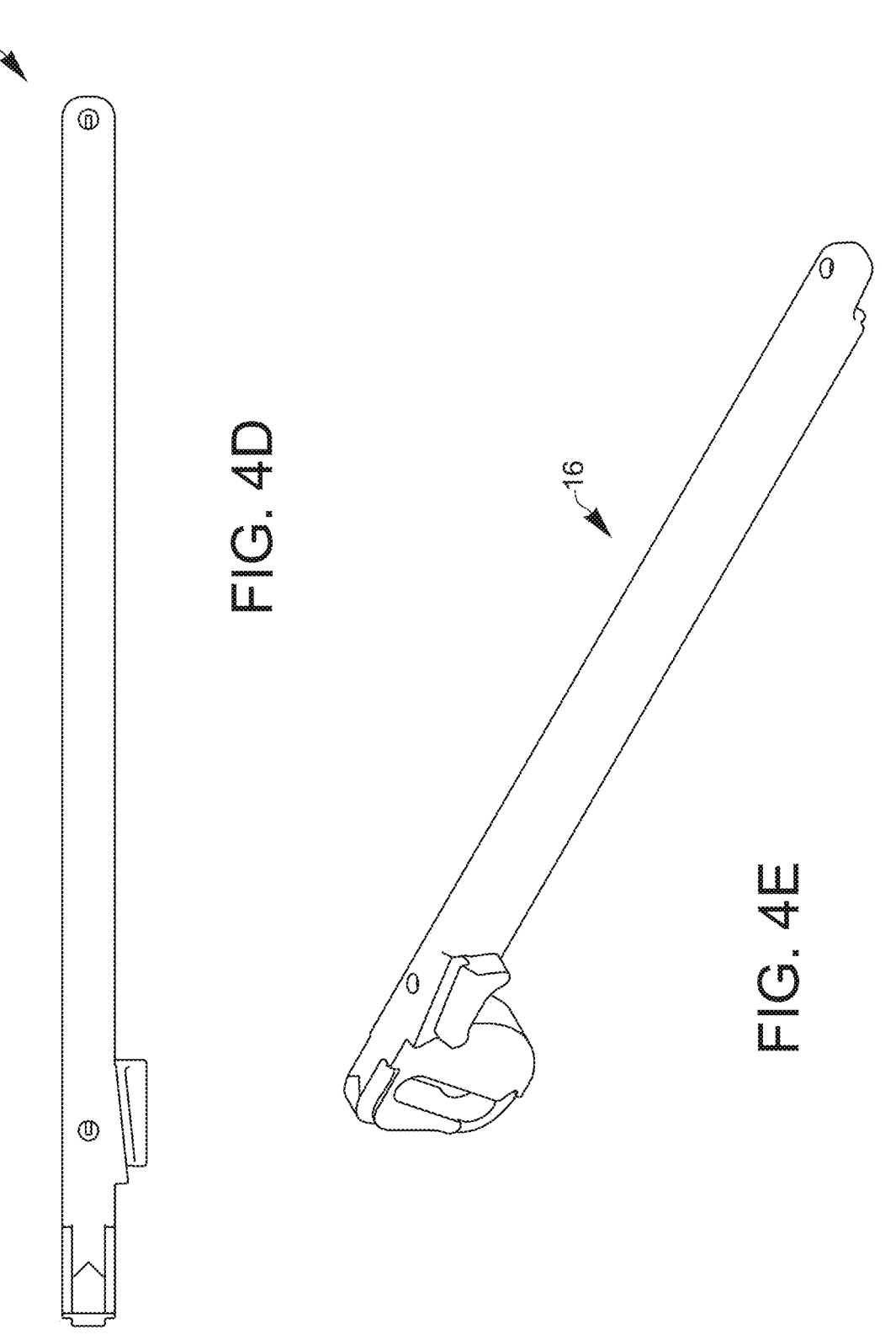

The second arm body 116 may also include a second coupling portion 134 disposed at the first end 118 of the second arm body 116, and the second coupling portion 134 may include a first tab 135 and a second tab 136, with each of the first tab 135 and the second tab 136 being planar (parallel to the X-Z plane of the reference coordinate system of FIG. 3D) and offset from the second arm body axis 122 to create a gap. The first tab 135 and the second tab 136 are configured to receive the first lateral surface 42 and the second lateral surface 44 of the first coupling portion 34 in the gap created by the first tab 135 and the second tab 136. An axis aperture 137 may be disposed through a portion of the first tab 135 and the second tab 136. The atrial clip assembly 10 may include a cylindrical axle 139 that extends through the axis aperture 137, and the cylindrical axle 139 may be received within the slot 40 of the first arm assembly 12 such that the first arm assembly 12 may pivot relative to the second arm assembly 14 (and vice versa) about the cylindrical axle 139. Further, the cylindrical axle 139 may have a diameter slightly smaller than a width of the slot 40 such that the cylindrical axle 139 may linearly displace within the slot 40 along the first coupling axis 36 to allow the first arm assembly 12 to displace relative to the second arm assembly 14 (and vice versa) while maintaining the ability to pivot. Such displacement allows the first arm assembly 12 to maintain a parallel relationship with the second arm assembly 14 when applied to the LAA so as to maintain an even pressure across the clipped portion of the LAA.

A portion 138 of the second coupling portion 134 may be coupled to the first end 126 of the second support portion 124. A first notch edge portion 146 may extend along a portion of the second support portion 124 from the first end 126 towards the second end 128, and the first notch edge portion 146 may have a concave, arcuate, or semi-circular shape when viewed along the Y-axis of the reference coordinate system of FIGS. 3D and 3E. A second notch edge portion 148 may extend along a portion of the second support portion 124 from the second end 128 towards the first end 126, and the second notch edge portion 148 may have a concave, semi-concave, or semi-circular shape when viewed along the Y-axis of the reference coordinate system of FIGS. 3D and 3E. A support ledge 174 may be disposed along all or a portion of the portion 138, and the support ledge 174 may extend from a lateral edge or lateral surface of the second support portion 124. A lower surface of the support ledge 174 may include a channel that is configured to support one or more portions of suture that may be used to secure the atrial clip assembly 10 in the closed position or to secure the atrial clip assembly 10 to the introducer device 200. The portion 138 of the second coupling portion 134 may be coupled to the first end 126 of the second support portion 124 in any suitable manner, and the second coupling portion 134 and the second support portion 124 may be integrally formed as a single, unitary part. The second arm body 116 may be injection molded as a single piece part, and may be made from or comprise a plastic material (for example, ABS or nylon).

As illustrated in the cross-sectional view of FIG. 1F, the second arm assembly 14 may also include a second spine portion 150 that extends along all or a portion of the second support portion 124 of the second arm body 116. The second spine portion 150, may be identical to the first spine portion (illustrated in FIG. 2A) and may be elongated and may extend from a first end 152 to a second end 154 along a second spine axis 156 that may be aligned with the second arm body axis 122. The first end 152 may be at or adjacent to (e.g., slightly offset from) the first end 126 of the second support portion 124, and the second end 54 may be at or adjacent to (e.g., slightly offset from) the second end 128 of the second support portion 124. The second spine portion 150 may have a first aperture 158 adjacent to the first end 152, and the first aperture 518 may extend along an axis that is normal to the second spine axis 156. The second spine portion 150 may also have a second aperture 160 adjacent to the second end 154, and the second aperture 160 may extend along an axis that is normal to the second spine axis 156.

Similarly or identically to the first spine portion 50, the second spine portion 150 may be co-molded with the second arm body 116 in any suitable manner. For example, the second spine portion 150 may be placed in a mold used to form the second arm body 116, and the part of the second arm body 116 may be formed around to surround the second spine portion 150. As such, a first arm aperture 162 may be formed on a surface at least partially defining the first notch edge portion 146 of the second support portion 124 (e.g., in the second support portion 124 at or adjacent to the first end 126) and the first arm aperture 162 may be aligned with the first aperture 158 of the second spine portion 150. Further, a second farm aperture 164 may be formed on a surface at least partially defining the second notch edge portion 148 of the second support portion 124 (e.g., in the second support portion 124 at or adjacent to the second end 128) and the second arm aperture 164 may be aligned with second aperture 160 of the second spine portion 150.

In some embodiments of the atrial clip assembly 10, the second arm assembly 14 may also include one or more portions of suture 166 that may be wrapped around an exterior surface 161 of the second spine portion 150 prior to molding the second support portion 124 over the second spine portion 150, and the one or more portions of suture 166 wrapped around the exterior surface 161 of the second spine portion 150 may be identically configured to the one or more portions of suture 66 that may be wrapped around an exterior surface 61 of the first spine portion 50 previously discussed. After molding, a first end 168 of the one or more portions of suture 166 may extend through the first arm aperture 162 of the second support portion 124 and all or a portion of the first aperture 158 of the second spine portion 150. Also after molding, a second end 170 of the one or more portions of suture 166 may extend through the second arm aperture 164 of the second support portion 124 and all or a portion of the second aperture 160 of the second spine portion 150.

When the first arm assembly 12 and the second arm assembly 14 are applied to the LAA (for example, by using an introducer 200 that will be discussed in more detail below, and when the first arm assembly 12 and second arm assembly 14 are in an engaged position (or when the atrial clip assembly 10 is in an engaged position) engaging the portion of the LAA, the first arm assembly 12 and the second arm assembly 14 may be secured together in any suitable manner to apply an even pressure across the portion of the LAA to isolate the interior of the LAA. In some embodiments, the first end 68 of the one or more portions of suture 66 of the first arm assembly 12 may be secured to the first end 168 of the one or more portions of suture 166 of the second arm assembly 14. Alternatively, or in addition, the second end 70 of the one or more portions of suture 66 of the first arm assembly 12 may be secured to the second end 170 of the one or more portions of suture 166 of the second arm assembly 14. For example, as illustrated in the embodiment of FIGS. 1A to 1C, a first crimpable sleeve 80a (illustrated in an uncrimped configuration for clarity) may be used to secure the first end 68 and the first end 168, and/or a second crimpable sleeve 80b (illustrated in an uncrimped configuration for clarity) may be used to secure the second end 70 and the second end 170. The crimpable sleeves 80a, 80b may be crimped or secured using a COR-KNOT® or COR-KNOT MINI® device manufactured by LSI Solutions, Inc. to secure both the first ends 68, 168 and the second ends 70, 170 within the crimped sleeve (not shown).

The first notch edge portion 46 of the first arm assembly 12 and the first notch edge portion 146 of the second arm assembly 14 may cooperate to provide a suitable space or gap for the cylindrical first crimpable sleeve 80a such that the first crimpable sleeve 80a does not contact or interfere with the desired positioning of the first arm assembly 12 and the second arm assembly 14 when in the engaged position. Similarly, the second notch edge portion 48 of the first arm assembly 12 and the second notch edge portion 148 of the second arm assembly 14 may cooperate to provide a suitable space or gap for the cylindrical second crimpable sleeve 80b such that the second crimpable sleeve 80b does not contact or interfere with the desired positioning of the first arm assembly 12 and the second arm assembly 14 when in the engaged position.

Figures 9A, 9B, 9C:
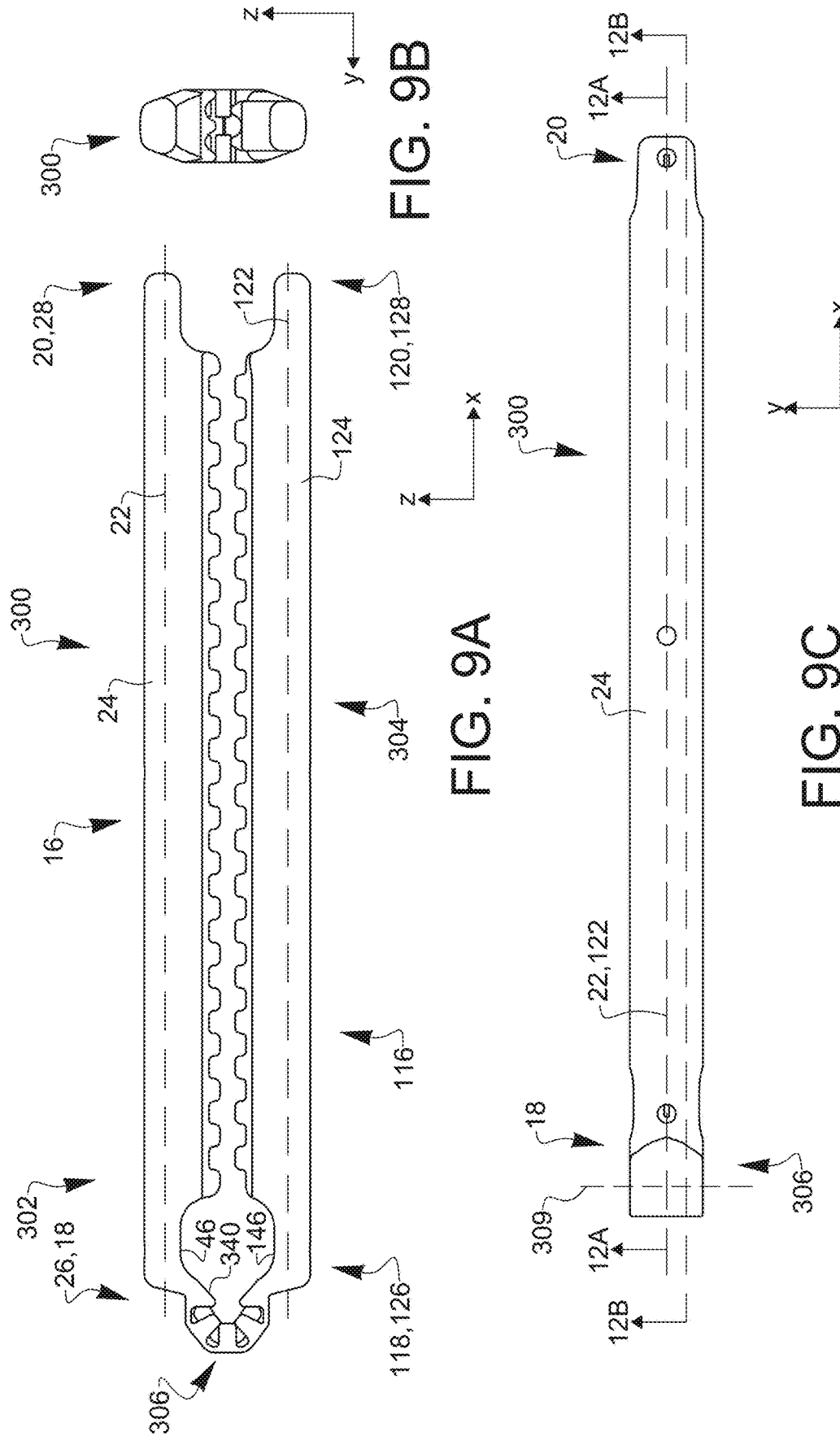
Figure 11:
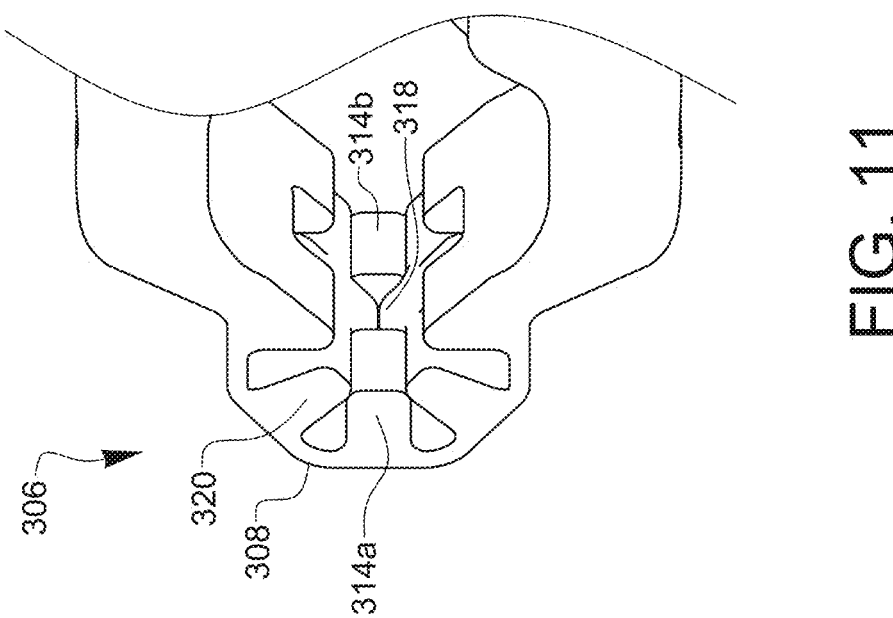
Figure 10:
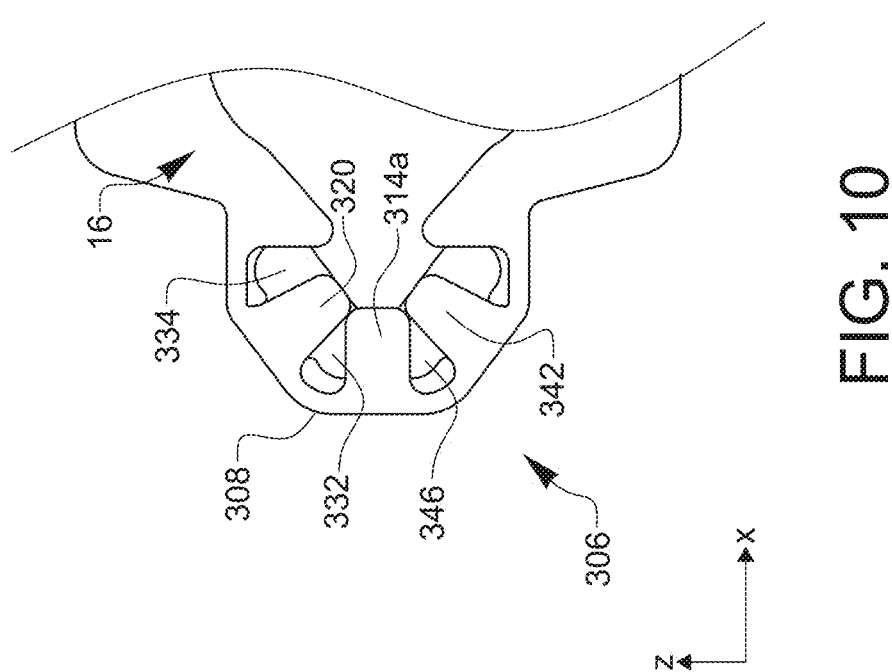
Figures 12A, 12B:
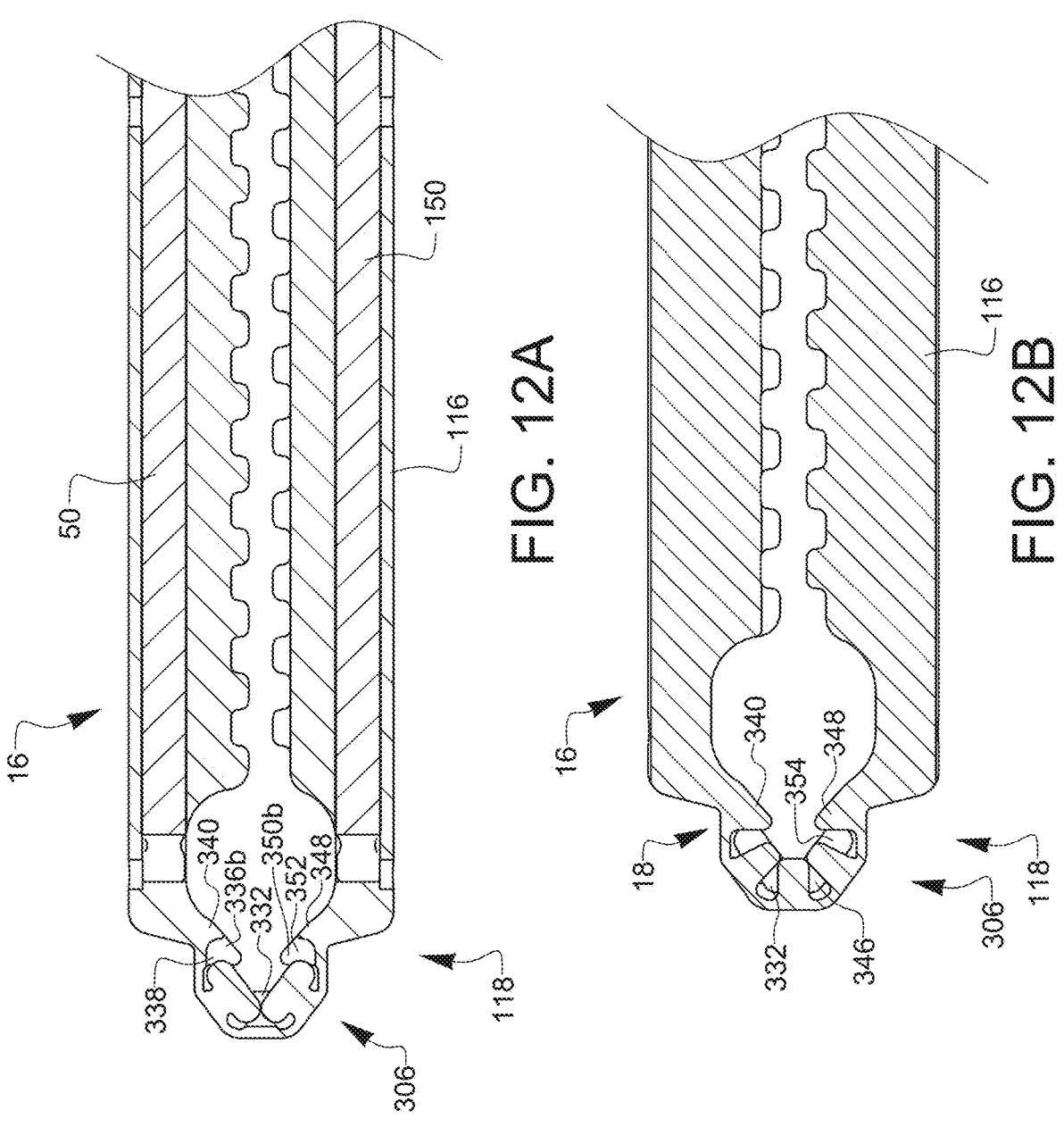
FIGS. 12A and 12B are sectional views of the embodiment of the atrial clip assembly of FIGS. 9A to 9C.
Figures 36A, 36B:
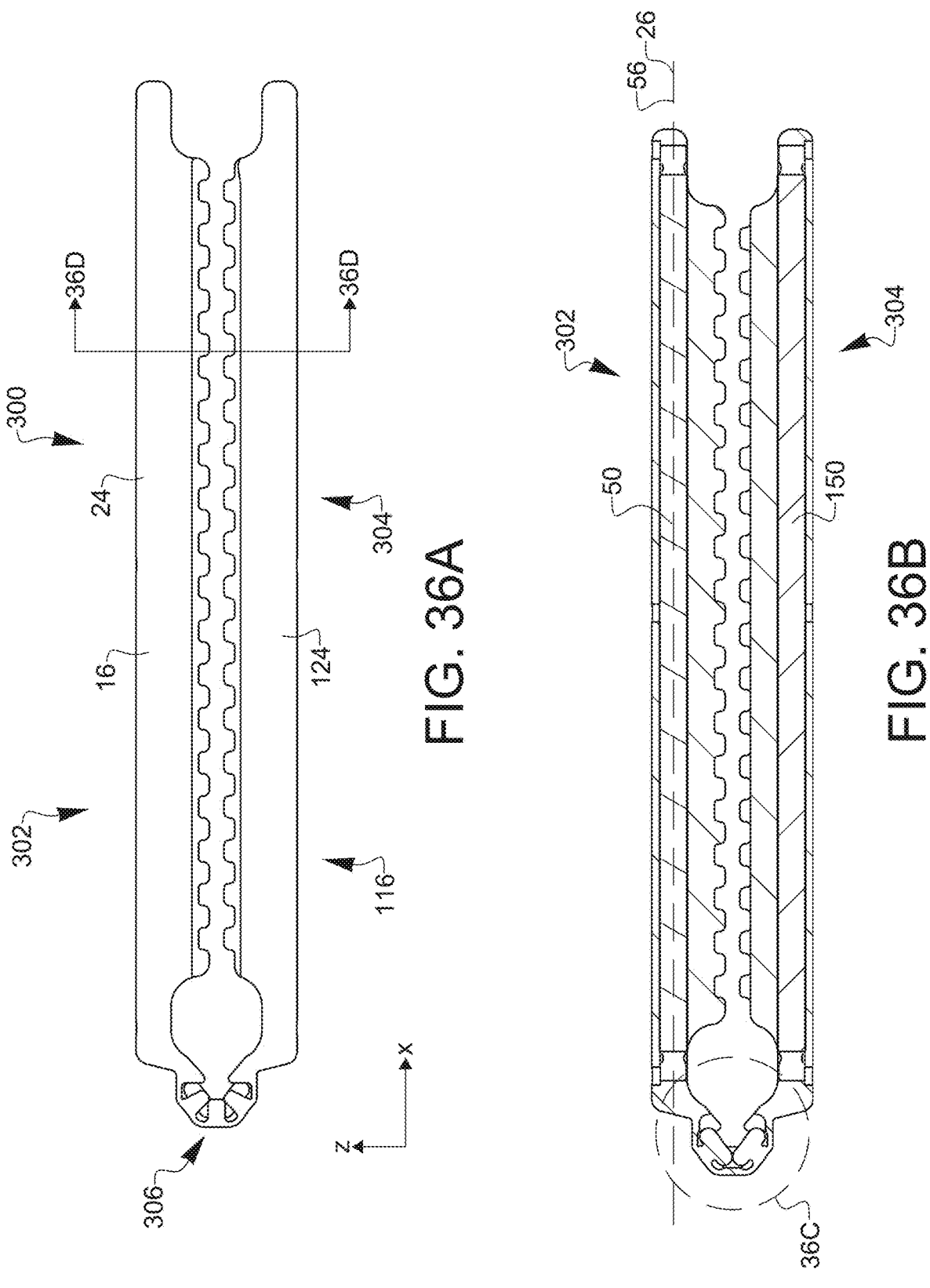
FIGS. 36A to 36D are various views of an embodiment of an atrial clip assembly.
Figure 36D:
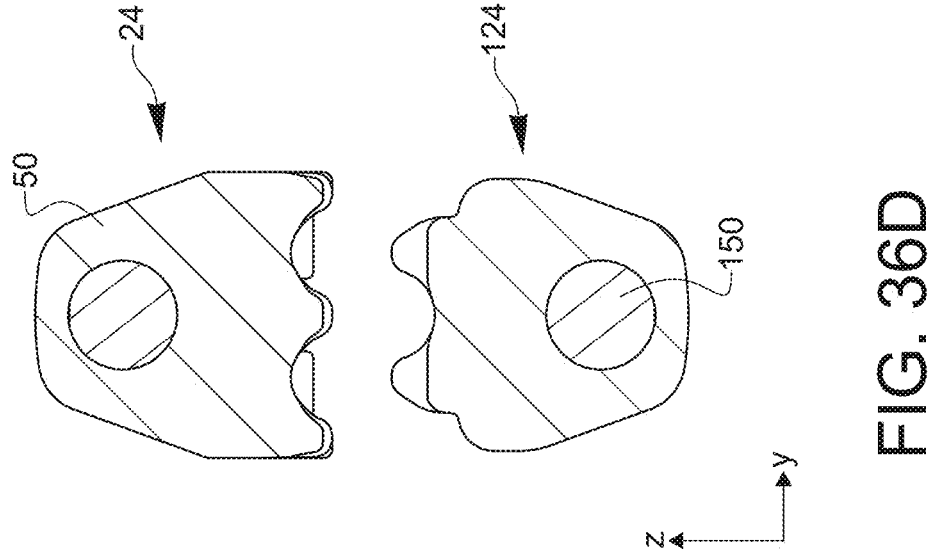
Figure 36C:
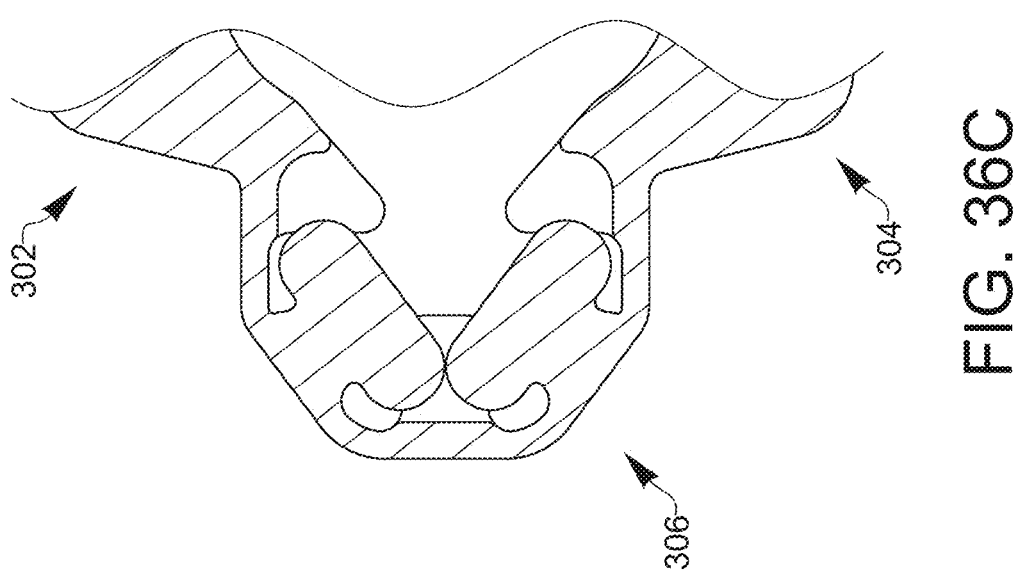

As illustrated in FIGS. 9A to 9C and 36A to 36D, a further embodiment of an atrial clip assembly 300 is provided that may be similar to the atrial clip assembly 10 with the exception of a living hinge coupling, and specific features of the atrial clip assembly 300 that are similar or identical to those of the atrial clip assembly 10 will share the same reference numbers. In particular, as illustrated in FIGS. 9a and 36A, the first arm assembly 302 of the atrial clip assembly 300 may include the first arm body 16 which may extend from the first end 18 to the second end 20 along the first arm body axis 22, and the first arm body 16 may include the first support portion 24 that extends from the first end 26 to the second end 28 along the first arm body axis 22. In this embodiment, the first arm body 16 and the first support portion 24 may be identical or coextensive such that the first end 18 of the first arm body 16 corresponds to the first end 26 of the first support portion 24 and the second end 20 of the first arm body 16 corresponds to second end 28 of the first support portion 24. However, first end 26 of the first support portion 24 may be offset (along the X-axis of the reference coordinate system of FIG. 9A) from the first end 18 of the first arm body 16, as with the atrial clip assembly 300. The first notch edge portion 46 may extend along a portion of the first support portion 24 from a point at or adjacent to the first end 26 towards the second end 28, and the first notch edge portion 46 may have a concave, arcuate, or semi-circular shape when viewed along the Y-axis of the reference coordinate system of FIG. 9A.

Further, the second arm assembly 304 of the atrial clip assembly 300 may include second arm body 116 which may extend from the first end 118 to the second end 120 along the second arm body axis 122, and the second arm assembly 304 may include the second support portion 124 that extends from the first end 126 to the second end 128 along the second arm body axis 122. In this embodiment, the second arm body 116 and the second support portion 124 may be identical or coextensive such that the first end 118 of the second arm body 116 corresponds to the first end 126 of the second support portion 124 and the second end 120 of the second arm body 116 corresponds to second end 128 of the second support portion 124. However, first end 126 of the second support portion 124 may be offset (along the X-axis of the reference coordinate system of FIG. 9A) from the first end 118 of the second arm body 116, as with the atrial clip assembly 300. The first notch edge portion 146 may extend along a portion of the second support portion 124 from a point at or adjacent to the first end 126 towards the second end 128, and the first notch edge portion 146 may have a concave, arcuate, or semi-circular shape when viewed along the Y-axis of the reference coordinate system of FIG. 9A.

Referring to FIGS. 9A, 10, 11, 36A, and 36C, the atrial clip assembly 300 may also have a hinge portion 306 that couples the first arm assembly 302 and the second arm assembly 304, and the hinge portion 306 may extend from the first end 18 of the first arm body 16 of the first arm assembly 302 to the first end 118 of the second arm body 116 of the second arm assembly 304. The hinge portion 306 may be a "living hinge" and may be integrally formed with the first end 18 of the first arm body 16 of the first arm assembly 302 and the first end 118 of the second arm body 116 of the second arm assembly 304 such that the hinge portion 306, the first arm body 16 of the first arm assembly 302, and the second arm body 116 of the second arm assembly 304 are a single, unitary part, and this part may be manufactured or fabricated as an injection-molded plastic part. The hinge portion 306 may be flexible and may be configured to be bent or to rotate about a pivot axis 309 (see FIG. 9C) that may be parallel to the Y-axis of the reference coordinate system of FIG. 9A. In some embodiments, the hinge portion

306 may have one or more features that are configured to prevent rotation of the hinge portion 306 about any axis that is not parallel to the Y-axis.

Figure 13A:
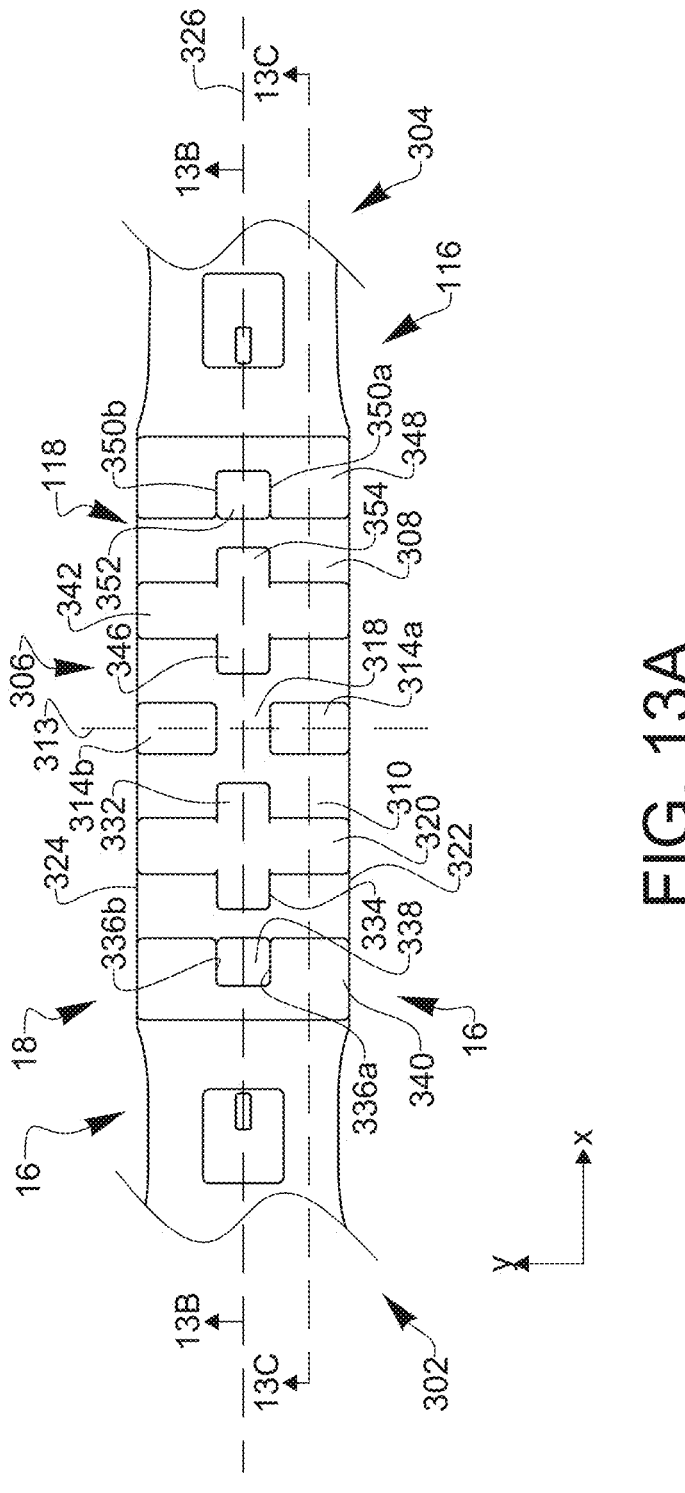
FIG. 13A is a partial top views of a hinge portion of the embodiment of the atrial clip assembly of the embodiment of the atrial clip assembly of FIGS. 9A to 9C.

Referring to FIG. 13A, which is a top view of the hinge portion 306 in a linear "flat" configuration, which may be the configuration in which the atrial clip assembly 300 is manufactured, the hinge portion 306 may include a base member 308 that may extend from the first end 18 of the first arm body 16 to the first end 118 of the second arm body 116 along a base axis 326 that may be parallel to the X-axis of the reference coordinate system of FIG. 13A. The base member 308 may be at least partially defined by a top surface 310 and a bottom surface 312 (illustrated in the cross-sectional view of FIG. 13B) which may each be planar or substantially planar and may be parallel to the X-Y plane of the reference coordinate system of FIG. 13A.

Figures 13B, 13C:
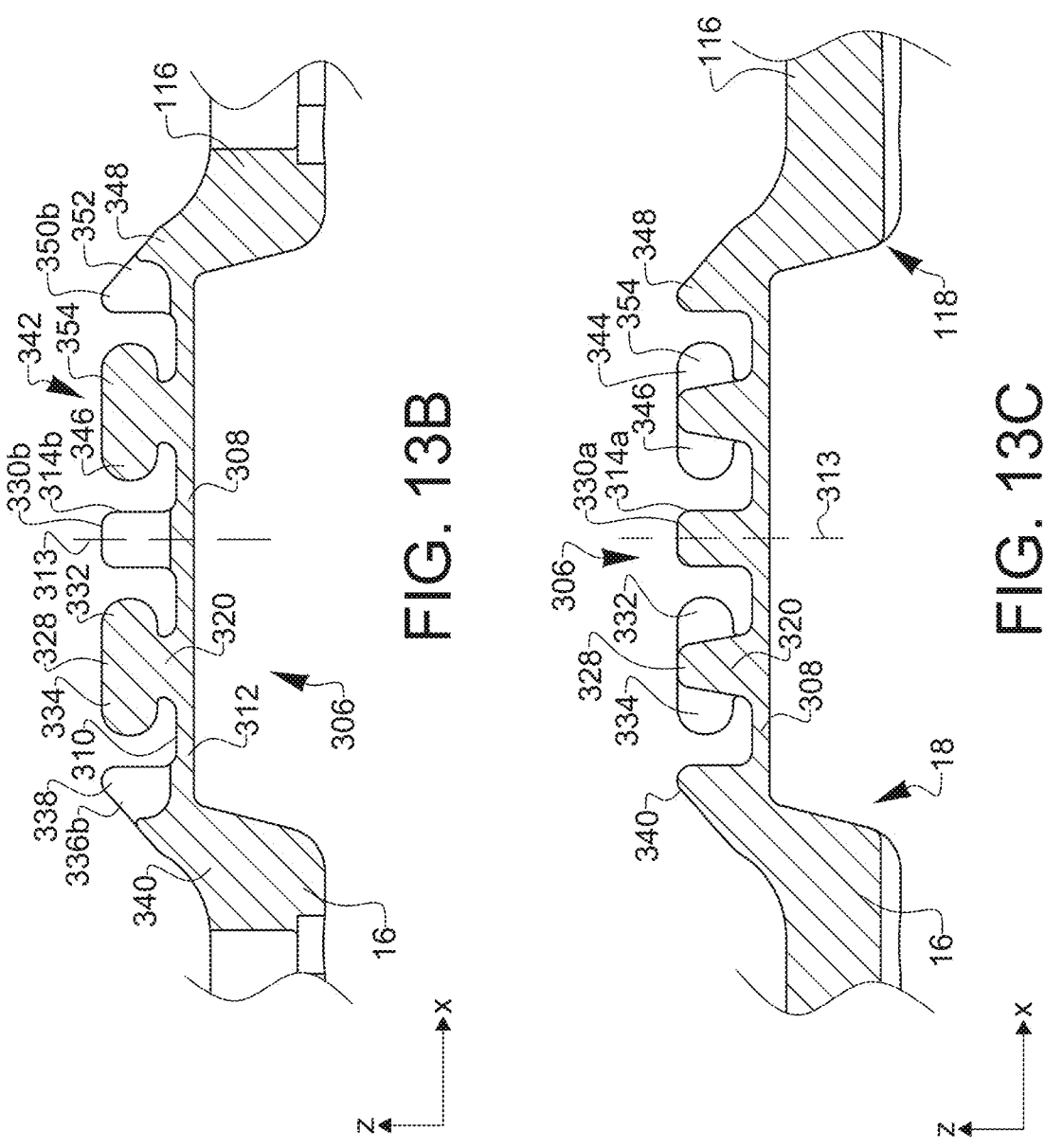
FIGS. 13B and 13C are sectional views of the hinge portion of the embodiment of the atrial clip assembly of FIG. 13A.

The hinge portion 306 may also include a first support protrusion 314a and a second support protrusion 314b that may each upwardly extend from the top surface 310, and the first support protrusion 314a and the second support protrusion 314b may be aligned along, and each symmetrically disposed about, a reference plane 313 that may be parallel to the Y-Z plane of the reference coordinate system of FIGS. 13A and 13B. An inner lateral wall 316a of the first support protrusion 314a and an inner lateral wall 316b of the second support protrusion 314b may each be disposed parallel (or substantially parallel) to the X-Z plane of the reference coordinate system of FIGS. 13A and 13B such that the inner lateral walls 316a, 316b define a center gap 318 disposed along the Y-axis of the reference coordinate system of FIG. 9A.

The hinge portion 306 may also include a first engagement protrusion 320 that may upwardly extend from the top surface 310 base member 308 and may laterally extend from a first lateral edge 322 of the base member 308 to a second lateral edge 324 of the base member 308 along (or substantially along) an axis normal to the base axis 326. A top surface 328 (needs new ##) of the first engagement protrusion 320 may be parallel to the top surface 310 of the base member 308 and the top surface 328 may be aligned or generally aligned with a top surface 330a, 330b of one or both of the first and second support protrusion 314a, 314b. A first inner tab 332 may extend from a first portion of the top portion of the first engagement protrusion 320 towards the center gap 318 along the base axis 326, and the first inner tab 332 may have a width (parallel to the Y-axis of the reference coordinate system of FIG. 13A) that is less than (or slightly less than) the distance between the inner lateral walls 316a, 316b that defines the center gap 318. Thus, when the atrial clip assembly 300 is in the engaged (closed) position illustrated in FIG. 9A, all or a portion of the first inner tab 332 is disposed within a first portion of the center gap 318 defined between the inner lateral walls 316a, 316b. When the atrial clip assembly 300 is in the disengaged (open) position illustrated in FIGS. 33A to 33D, the first inner tab 332 may be disposed outside of the center gap 318 defined between the inner lateral walls 316a, 316b. However, in some embodiments, the first inner tab 332 may extend a sufficient distance towards the center gap 318 that a portion of the first inner tab 332 may be disposed within the first portion of the center gap 318 defined between the inner lateral walls 316a, 316b in the disengaged or partially disengaged position.

Referring again to FIG. 13A, a first lateral wall 336a and a second lateral wall 336b may be formed in a first end protrusion 340 disposed at or extending from the first end 18 of the first arm body 16, and the first lateral wall 336a and a second lateral wall 336b may at least partially define a first end notch 338 disposed in the first end protrusion 340. The first lateral wall 336a and the second lateral wall 336b may be symmetrically disposed about the base axis 326 and aligned with the corresponding inner lateral walls 316a, 316b defining the center gap 318 such that the first end notch 338 is aligned with the center gap 318.

A first outer tab 334 may extend from a second portion of the top portion of the first engagement protrusion 320 towards the first end notch 338 along the base axis 326, and the first outer tab 334 may have a width (parallel to the Y-axis of the reference coordinate system of FIG. 13A) that is less than (or slightly less than) the distance between the first lateral wall 336a and the second lateral wall 336b that defines the first end notch 338. Thus, when the atrial clip assembly 300 is in the engaged (closed) position illustrated in FIG. 9A, all or a portion of the first outer tab 334 is disposed within the first end notch 338 defined between the first lateral wall 336a and the second lateral wall 336b. When the atrial clip assembly 300 is in the disengaged (open) position illustrated in FIGS. 33A to 33D, the first outer tab 334 may be disposed outside of the first end notch 338 defined between the first lateral wall 336a and the second lateral wall 336b. However, in some embodiments, the first outer tab 334 may extend a sufficient distance towards the first end notch 338 that a portion of the first outer tab 334 may be disposed within a portion of the first end notch 338 defined between the first lateral wall 336a and the second lateral wall 336b in the disengaged or partially disengaged position.

The hinge portion 306 may also include a second engagement protrusion 342 that may be identical or substantially identical to the first engagement protrusion 320, and symmetrically disposed about the reference plane 313 from the first engagement protrusion 320. In particular, the second engagement protrusion 342 may upwardly extend from the top surface 310 base member 308 and may laterally extend from the first lateral edge 322 of the base member 308 to the second lateral edge 324 of the base member 308 along (or substantially along) an axis normal to the base axis 326. A top surface 344 of the second engagement protrusion 342 may be parallel to the top surface 310 of the base member 308 and the top surface 342 may be aligned or generally aligned with a top surface 330a, 330b of one or both of the first and second support protrusion 314a, 314b. A second inner tab 346 may extend from a first portion of the top portion of the second engagement protrusion 342 towards the center gap 318 along the base axis 326, and the second inner tab 346 may have a width (parallel to the Y-axis of the reference coordinate system of FIG. 13A) that is less than (or slightly less than) the distance between the inner lateral walls 316a, 316b that defines the center gap 318. Thus, when the atrial clip assembly 300 is in the engaged (closed) position illustrated in FIG. 9A, all or a portion of the second inner tab 346 is disposed within a second portion of the center gap 318 defined between the inner lateral walls 316a, 316b. When the atrial clip assembly 300 is in the disengaged (open) position illustrated in FIGS. 33A to 33D, the second inner tab 346 may be disposed outside of the portion of the center gap 318 defined between the inner lateral walls 316a, 316b. However, in some embodiments, the second inner tab 346 may extend a sufficient distance towards the center gap 318 that a portion of the second inner tab 346 may be disposed within the second portion of the center gap 318 defined between the inner lateral walls 316a, 316b in the disengaged or partially disengaged position.

Referring again to FIG. 13A, a first lateral wall 350*a* and a second lateral wall 350*b* may be formed in a second end protrusion 348 disposed at or extending from the first end 118 of the second arm body 116, and the first lateral wall 350*a* and the second lateral wall 350*b* may at least partially define a second end notch 352 disposed in the second end protrusion 348. The first lateral wall 350*a* and the second lateral wall 350*b* may be symmetrically disposed about the base axis 326 and aligned with the corresponding inner lateral walls 316*a*, 316*b* defining the center gap 318 such that the second end notch 352 is aligned with the center gap 318.

A second outer tab 354 may extend from a second portion of the top portion of the second engagement protrusion 342 towards the second end notch 352 along the base axis 326, and the second outer tab 354 may have a width (parallel to the Y-axis of the reference coordinate system of FIG. 13A) that is less than (or slightly less than) the distance between the first lateral wall 350*a* and the second lateral wall 350*b* that defines the second end notch 352. Thus, when the atrial clip assembly 300 is in the engaged (closed) position illustrated in FIG. 9A, all or a portion of the second outer tab 354 is disposed within all or a portion of the second end notch 352 defined between the first lateral wall 350*a* and the second lateral wall 350*b*. When the atrial clip assembly 300 is in the disengaged (open) position illustrated in FIGS. 33A to 33D, the second outer tab 354 may be disposed outside of the second end notch 352 defined between the first lateral wall 350*a* and the second lateral wall 350*b*. However, in some embodiments, the second outer tab 354 may extend a sufficient distance towards the second end notch 352 that a portion of the second outer tab 354 may be disposed within a portion of the second end notch 352 defined between the first lateral wall 350*a* and the second lateral wall 350*b* in the disengaged or partially disengaged position.

As previously explained, the hinge portion 306 may be flexible and may be configured to be bent or to rotate about the pivot axis 309 (see FIG. 9C). When or as the atrial clip assembly 300 is displaced from the disengaged position illustrated in FIGS. 33A to 33D to the engaged position illustrated in FIG. 9A, all or a portion of the first inner tab 332 of the first engagement protrusion 320 is disposed within a first portion of the center gap 318, and all or a portion of the first outer tab 334 of the first engagement protrusion 320 is disposed within the first end notch 338 of the first end protrusion 340. Further, all or a portion of the second inner tab 346 of the second engagement protrusion 342 is disposed within a second portion of the center gap 318 and all or a portion of the second outer tab 354 of the second engagement protrusion 342 is disposed within all or a portion of the second end notch 352 of the second end protrusion 348. Thus, the interaction of the tabs within the center gap 318 and notches 338, 352 maintains the alignment of the first arm assembly 302 and the second arm assembly 304 about the X-Z plane of the reference coordinate system of FIGS. 13A and 13B such that the atrial clip assembly 300 may be pivoted only about the pivot axis 309 that may be parallel to the Y-axis of the reference coordinate system of FIG. 9A, thereby eliminating twisting or torsional forces about an axis parallel to the X-axis of the reference coordinate system of FIG. 9A or other twisting or torsional forces.

As illustrated in FIGS. 35A to 35C, the atrial clip assembly 10, 300 may be at least partially covered in a sheath 444. The sheath 444 may cover all, a portion, or two or more portions of the atrial clip assembly 10, 300. For example, the sheath 444 may cover (and/or surround) all or a portion of the first arm assembly 302, and the sheath 444 (or a separate sheath 444) may cover (and/or surround) all or a portion of the second arm assembly 304. In one embodiment, the sheath 444 may be a tube that receives or fully covers the first arm assembly 302, the hinge portion 306, and the second arm assembly 304. The sheath 444 may be made from a material that may facilitate connection or attachment to the patient's tissue, such as a cloth material, a synthetic material, a mesh material, or a combination of these, or any other suitable material(s).

When the first arm assembly 302 and the second arm assembly 304 are applied to the LAA (for example, by using an introducer 200 that will be discussed in more detail below, and when the first arm assembly 302 and second arm assembly 304 are in an engaged position (or when the atrial clip assembly 300 is in an engaged position) engaging the portion of the LAA, the first arm assembly 302 and the second arm assembly 304 may be secured together in any suitable manner to apply an even pressure across the portion of the LAA to isolate the interior of the LAA. As with the atrial clip assembly 10, the atrial clip assembly 300 may include the one or more portions of suture 66 that may be wrapped around the exterior surface 61 of the first spine portion 50, such as in a helical manner, and the one or more portions of suture 166 that may be wrapped around an exterior surface 161 of the second spine portion 150, such as in a helical manner. In such an embodiment, the first end 68 of the one or more portions of suture 66 of the first arm assembly 302 may be secured to the first end 168 of the one or more portions of suture 166 of the second arm assembly 304. Alternatively, or in addition, the second end 70 of the one or more portions of suture 66 of the first arm assembly 302 may be secured to the second end 170 of the one or more portions of suture 166 of the second arm assembly 304. For example, as illustrated in the embodiment of FIGS. 1A to 1C (and 34A and 35B), the first crimpable sleeve 80*a* (illustrated in an uncrimped configuration for clarity) may be used to secure the first end 68 and the first end 168, and/or a second crimpable sleeve 80*b* (illustrated in an uncrimped configuration for clarity) may be used to secure the second end 70 and the second end 170. In FIGS. 9A, 12A, 12B, 33D, 34B, 35C, 36A, and 36B, the one or more portions of suture 66 of the first spine portion 50 and the one or more portions of suture 166 of the second spine portion 150 are omitted for clarity. Further, in some embodiments of the atrial clip assembly 10, 300 the one or more portions of suture 66 of the first spine portion 50 and/or the one or more portions of suture 166 of the second spine portion 150 may not be used, and any manner of securing the first arm assembly 12, 302 and the second arm assembly 14, 304 may be used instead.

Figure 5:
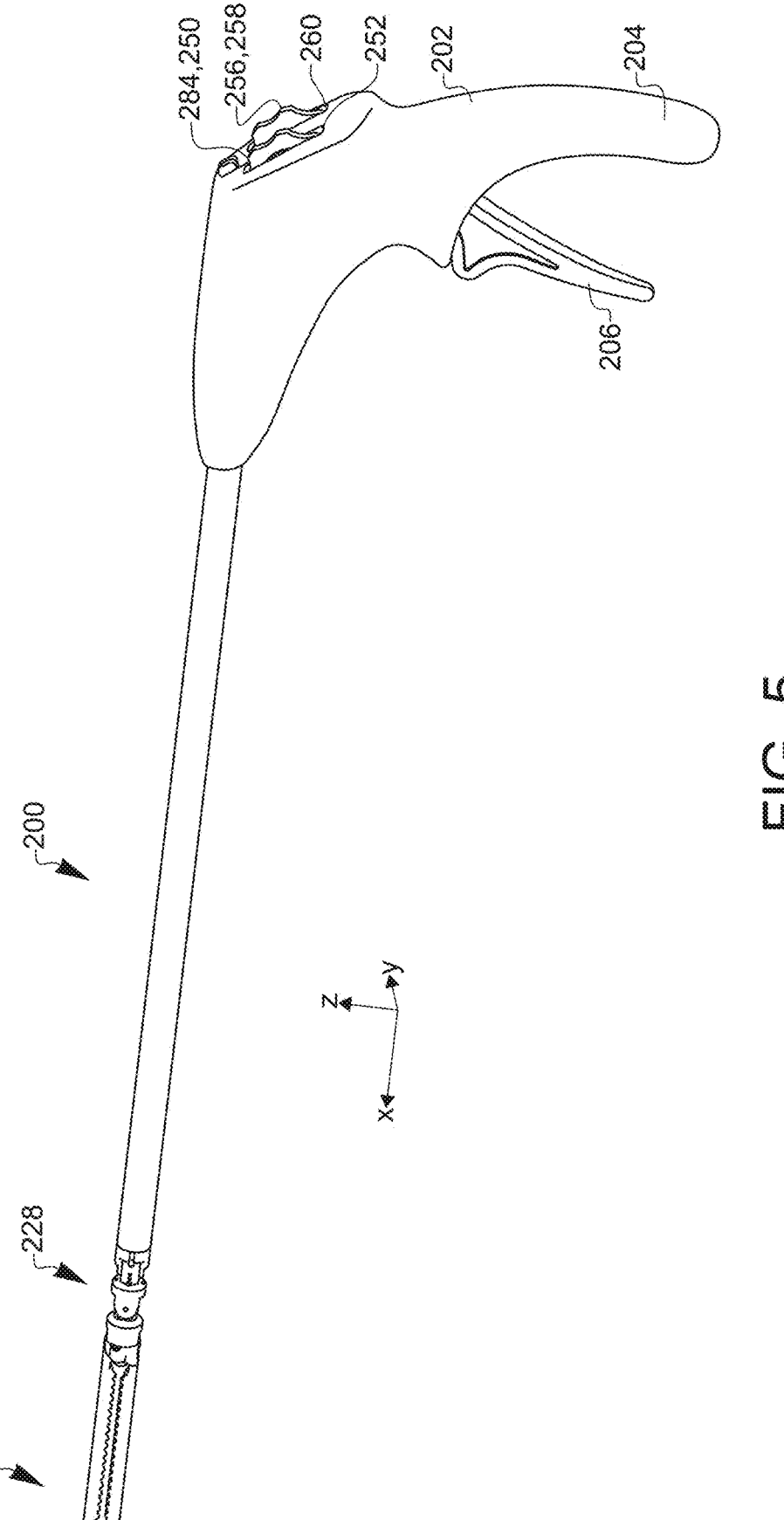
FIG. 5 is a perspective view of an embodiment of an introducer device for engaging the atrial clip assembly of FIGS. 1A to 1H during a procedure.
Figure 7:
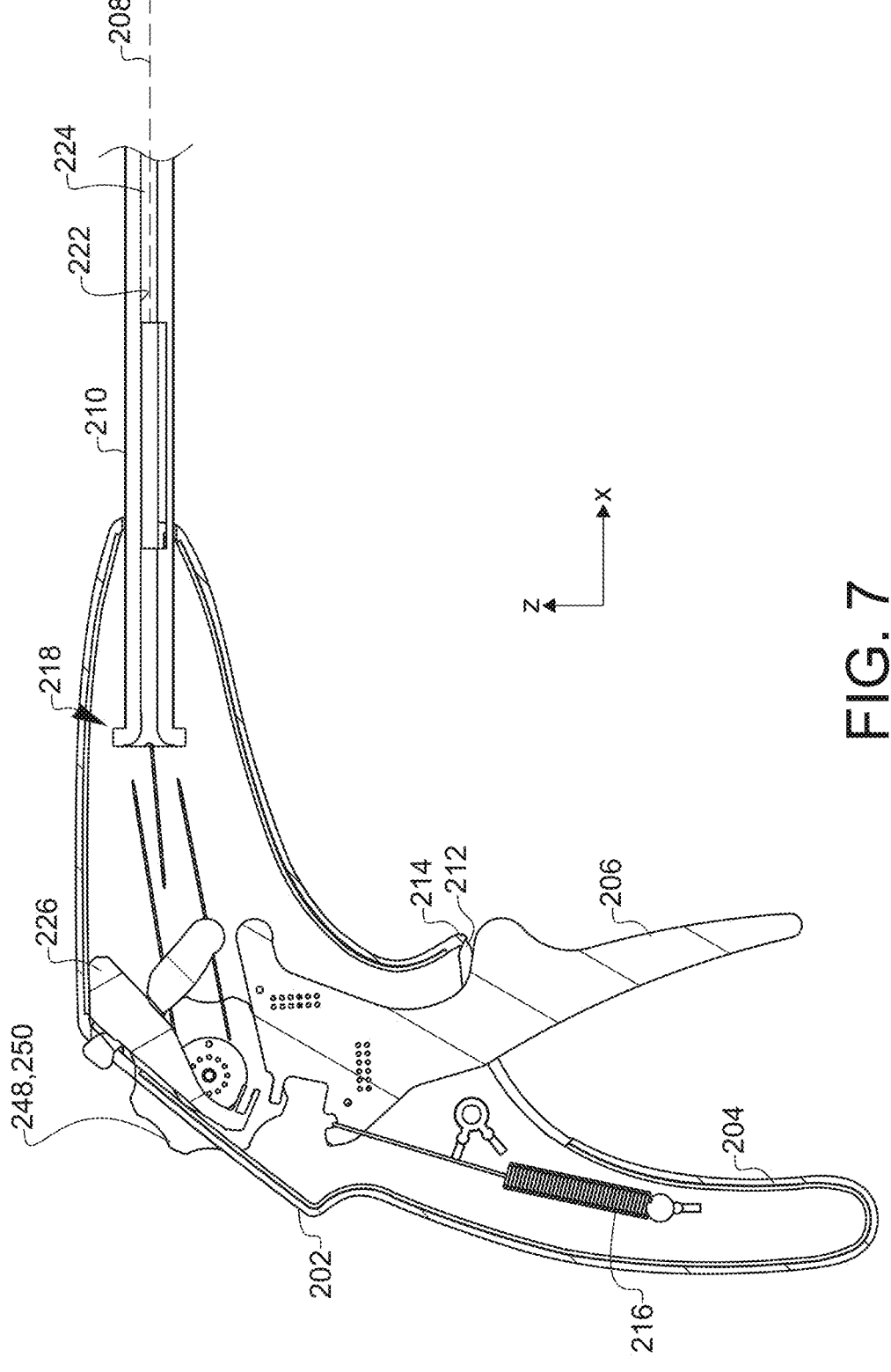
FIG. 7 is a detailed side view of FIG. 6.
Figure 8A:
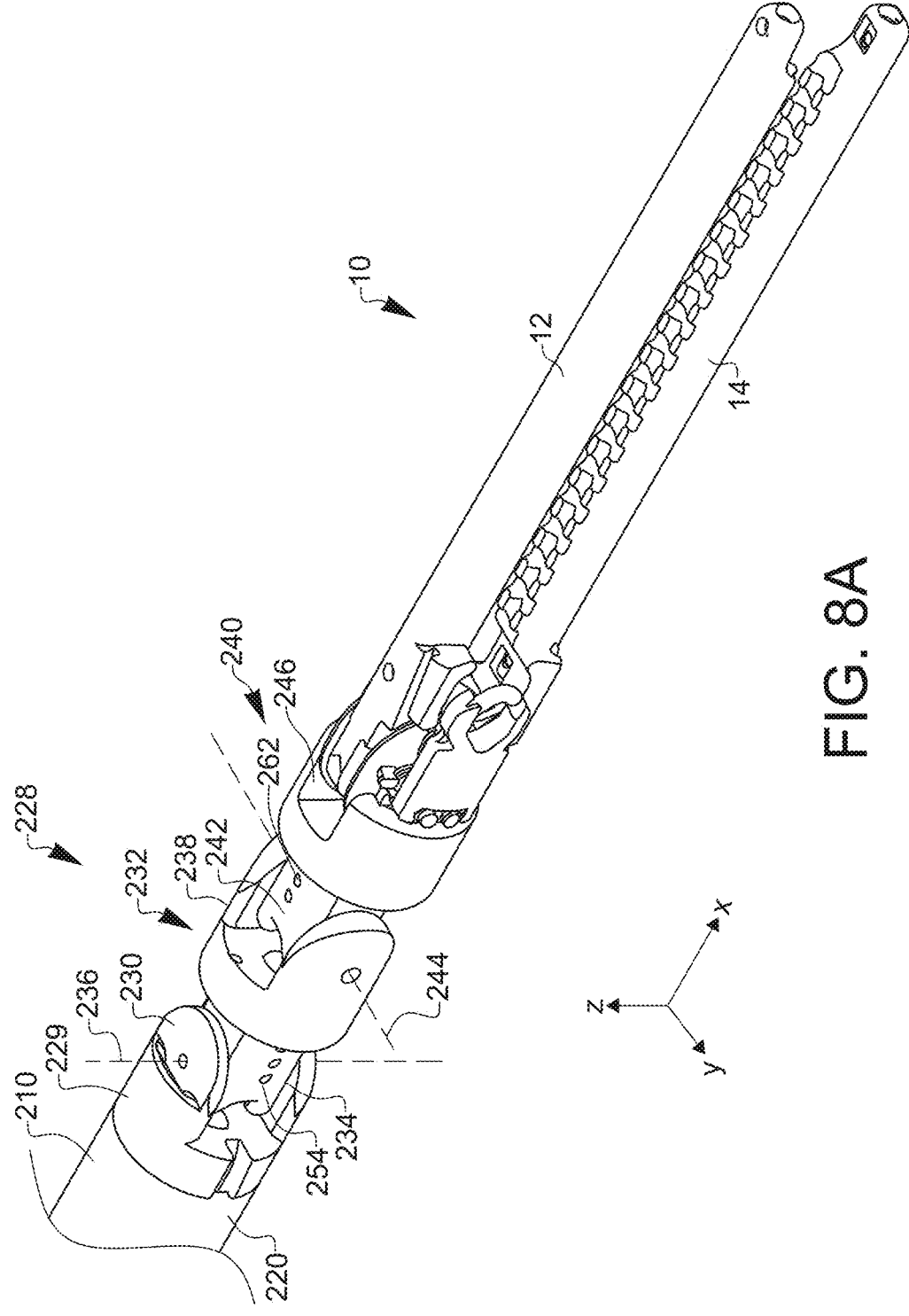
FIGS. 8A and 8D are various views of an embodiment of a coupling assembly of the embodiment of the introducer device of FIG. 5.
Figures 8B, 8C:
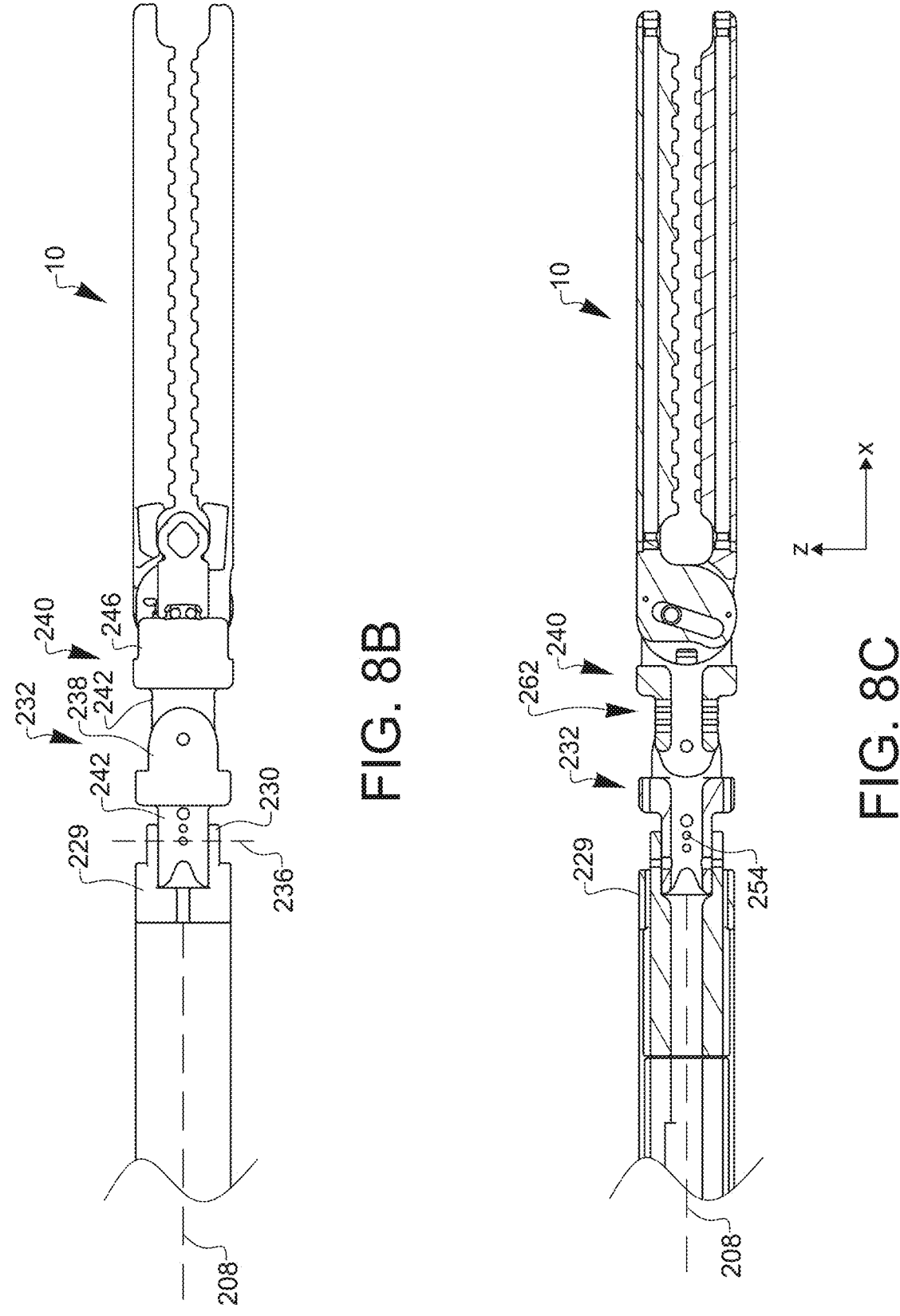
Figure 8D:
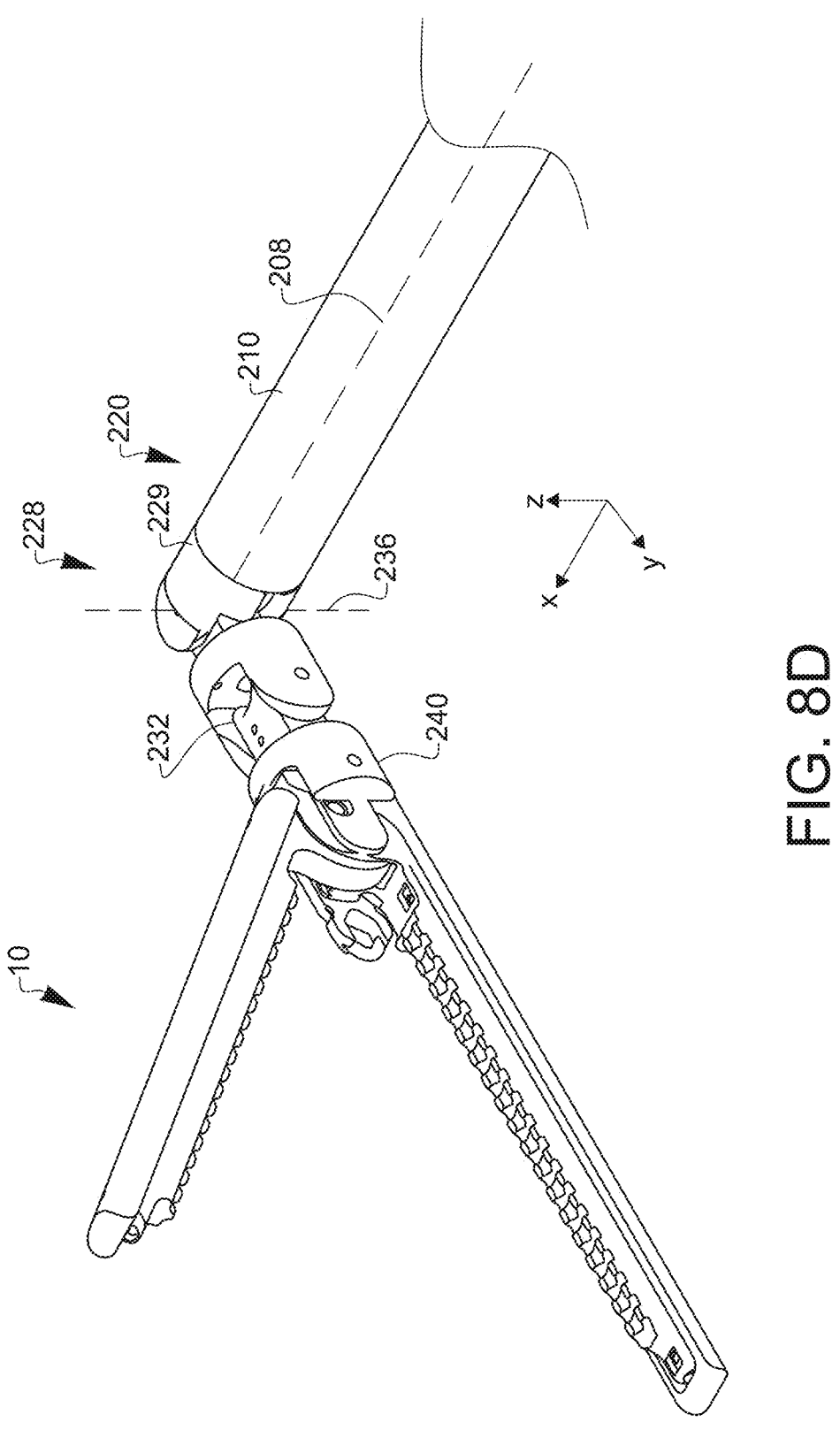

With reference to FIG. 5, the introducer device 200 may be used to position the atrial clip assembly 10, 300 around or adjacent to the LAA and to secure the atrial clip assembly 10, 300 to a portion of the LAA. The introducer device 200 may include a housing portion 202 having a grip portion 204 that is adapted to be grasped by a user to engage and displace an actuation lever 206 from a first lever position (illustrated in FIG. 5) to a second lever position (not shown, but pivoted towards the grip portion 204 by a user). The actuation lever 206 may be indirectly coupled to the atrial clip assembly 10, 300 such that when the actuation lever 206 is in the first lever position, the atrial clip assembly 10, 300 is in the open position (illustrated in FIG. 8D). When the atrial clip assembly 10, 300 is positioned in a desired location (such as adjacent to the LAA), the actuation lever 206 is pivoted from the first lever position to the second lever position, in which the atrial clip assembly 10, 300 is displaced into the engaged position (Illustrated in FIG. 5). With reference to FIG. 7 (in which a portion of the housing portion 202 is omitted for clarity), a first portion of the actuation lever 206 may be rotatably coupled to the housing portion 202 at a first portion (e.g., a pivot point) of the housing portion 202 such that the actuation lever 206 pivots between the first lever position to the second lever position about the pivot point. The actuation lever 206 may pivot about a pivot axis that may extend through the pivot point and may be normal to a shaft axis 208 that extends along a shaft 210 that is coupled to the housing portion 202. In particular, the first portion of the actuation lever 206 may be a pair of aligned bosses that are received into corresponding cylindrical internal walls that are each formed on a corresponding interior portion of the housing portion 202 at the pivot point of the housing portion 202. As shown in FIG. 7, a portion 212 of the actuation lever 206 may contact a portion 214 of the housing portion 202 when the actuation lever 206 is in the first lever position to prevent the actuation lever 12 from overextending beyond the first lever position. A first end of a spring 216 may be coupled to a portion of the actuation lever 206 and a second end of the spring 216 may be coupled to a portion of the interior portion of the housing portion 202 such that the actuation lever 206 is biased into the first lever position by the spring 216.

With reference to FIG. 7, the introducer device 200 may include a selective locking mechanism 226 to maintain or lock the position of the atrial clip assembly 10 in a desired position by manipulation of the actuation lever 206. By way of example, a user may engage the selective locking mechanism 226 by pivoting the actuation lever 206 towards the housing portion 202 to a specified position in which the selective locking mechanism 226 is engaged in a lock position in which the first arm assembly 12 and the second arm assembly 14 of the atrial clip assembly 10 are maintained, or locked, in the closed position. Further pivoting of the actuation lever 206 towards the housing portion 202 disengages the selective locking mechanism 226 and the first arm assembly 12 and the second arm assembly 14 are no longer maintained in the open position. The selective locking mechanism 226 may be identical to that selective locking mechanism described in U.S. patent application Ser. No. 18/107,392 filed on Feb. 8, 2023 and U.S. Provisional Patent App. No. 63/308,271 filed on Feb. 9, 2022, each of which is herein incorporated by reference in its entirety.

Figure 6:
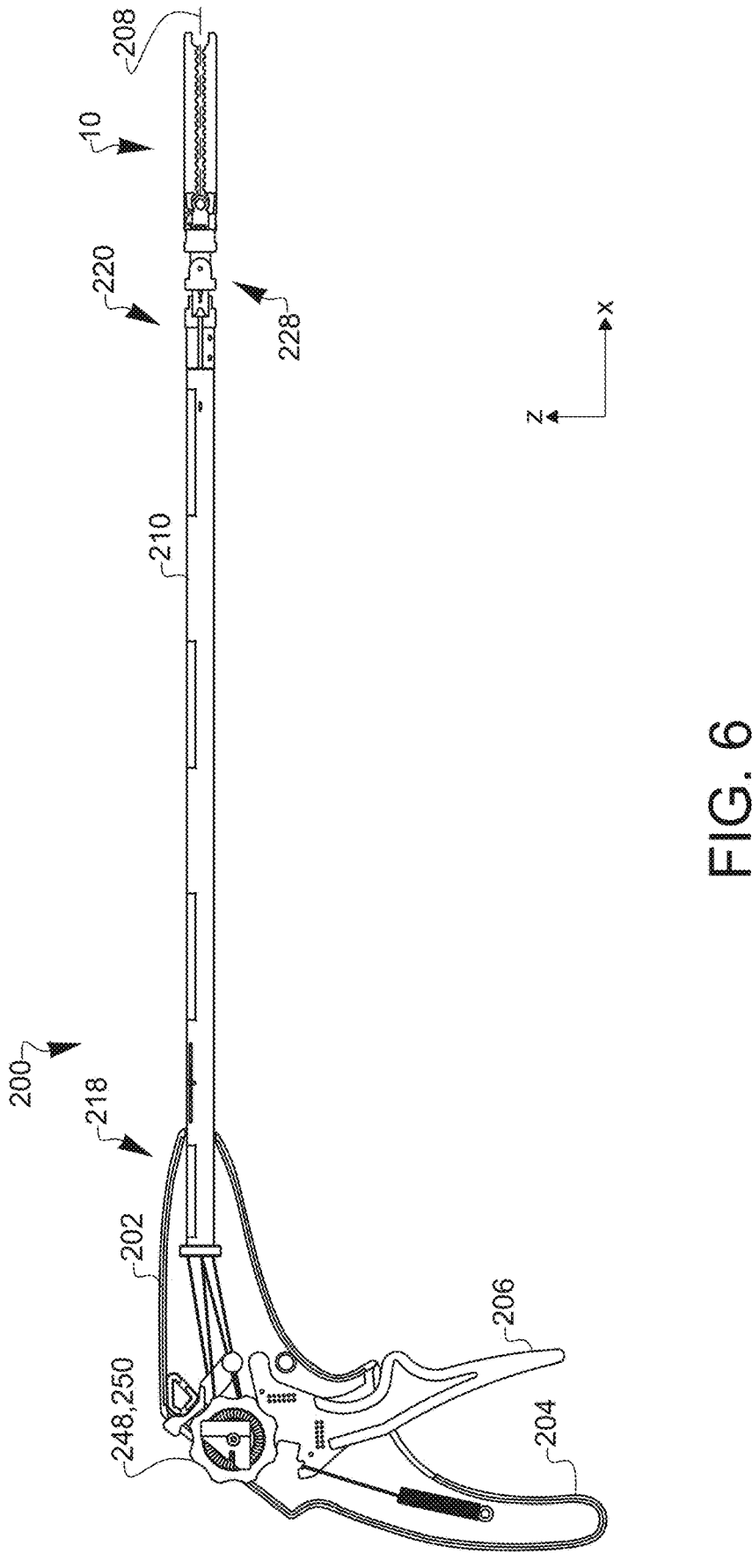
FIG. 6 is a side view of the embodiment of the introducer device of FIG. 5 (with a portion of the housing portion removed for clarity)

Referring to FIG. 6, the introducer device 200 includes the shaft 210 that extends from a proximal end 218 to a distal end 220 along the shaft axis 208, and the shaft axis 208 may be linear. One or more portions of the shaft 210 may be coupled to a second portion of the housing portion 202 such that the shaft 210, and the shaft 210 may be fixed relative to the housing portion 202. However, one or more portions of the shaft 210 may be rotatably coupled to the second portion of the housing portion 202 such that the shaft 210 rotates relative to the housing portion 202 about the shaft axis 208. The shaft 210 may be rigid, but in other embodiments, the shaft 210 may be flexible or may have one or more portions that are flexible.

The shaft 210, or one or more portions of the shaft 210, may have the general shape of an elongated hollow tube having an interior surface 222 (illustrated in FIG. 7) that defines an interior portion 224 that extends from the proximal end 218 to the distal end 220 of the shaft 210. The shaft 210 and the interior surface 222 may have any suitable cross-sectional shape or combination of shapes normal to the shaft axis 208. For example, the shaft 210 may have the general shape of an elongated cylinder, and the interior surface 222 may have a circular cross-sectional shape when viewed normal to the shaft axis 208.

The introducer device 200 also includes a coupling assembly 228 disposed or coupled to the distal end 220 of the shaft 210. The coupling assembly 228 is configured to be releasably coupled to the atrial clip assembly 10, 300 to allow the atrial clip assembly 10 to be properly positioned on the LAA and to displace the atrial clip assembly 10 from the open position (illustrated in FIG. 8D) to the engaged position (Illustrated in FIG. 5). The coupling assembly 228 incudes a hub portion 229 that is fixedly coupled to the distal end 220 of the shaft 210, and the hub portion 229 may include a yoke portion 230, and an aperture may extend through the hub portion 229 along the shaft axis 208, as illustrated in the cross-sectional view of FIG. 8C. The coupling assembly 228 also includes a first rotational assembly 232 that is rotatably coupled to the hub portion 229. In particular, the first rotational assembly 232 includes a base portion 234 disposed within and rotatably coupled to the yoke portion 230 of the hub portion 229 such that the base portion 234 (and the entire first rotational assembly 232) rotates about an axis 236 normal to the shaft axis 208 and parallel to the Z-axis of the reference coordinate system of FIGS. 8A and 8D). A yoke portion 238 is coupled to the base portion 234 distal to the base portion 234. For example, a pin (not shown) may be disposed from a first portion of the yoke portion 230 of the hub portion 229 to a second portion of the yoke portion 230 of the hub portion 229, and the pin may extend through an aperture through the base portion 234, and the pin may extend along the axis 236. An aperture may extend through the first rotational assembly 232 along a longitudinal axis of the first rotational assembly 232, as illustrated in the cross-sectional view of FIG. 8C.

The coupling assembly 228 also includes a second rotational assembly 240 that is rotatably coupled to the first rotational assembly 232. In particular, the second rotational assembly 240 includes a base portion 242 disposed within and rotatably coupled to the yoke portion 238 of the first rotational assembly 232 such that the base portion 242 (and the entire second rotational assembly 240) rotates about an axis 244 normal to the shaft axis 208 and normal to the axis 236 of the first rotational assembly 232, and the axis may be disposed within the X-Y plane of the reference coordinate system of FIGS. 8A and 8D). For example, a pin (not shown) may be disposed from a first portion of the yoke portion 238 of the first rotational assembly 232 to a second portion of the yoke portion 238 of the first rotational assembly 232, and the pin may extend through an aperture through the base portion 242 of the second rotational assembly 240, and the pin may extend along the axis 244. An aperture may extend through the second rotational assembly 240 along a longitudinal axis of the second rotational assembly 240, as illustrated in the cross-sectional view of FIG. 8C.

The atrial clip assembly 10, 300 may be removably coupled to the second rotational assembly 240 in any suitable manner to allow the atrial clip assembly 10 to be displaced from the open position to the engaged (closed) position when the actuation lever 206 is pivoted from the first lever position to the second lever position. For example, the atrial clip assembly 10, 300 may be removably coupled to a yoke portion 246 of the second rotational assembly 240. In particular, one or more portions of the first coupling portion 34 of the first arm assembly 12 and/or one or more portions of the second coupling portion 134 of the second arm assembly 14 may be coupled to the yoke portion 246 of the second rotational assembly 240, and the first arm assembly 12 and the second arm assembly 14 may initially be in the first open position of FIG. 8D. The first arm assembly 12 and/or the second arm assembly 14 may be coupled to the yoke portion 246 using one or more portions of suture, and the one or more portions of suture may extend through the apertures of the hub portion 229, the first rotational assembly 232, the second rotational assembly 240 and the interior portion 224 of the shaft 210 to couple to the actuation lever 206 such that displacing the actuation lever 206 from the first lever position to the second lever position, via tension in the one or more portions of suture, closes or displaces the atrial clip assembly 10 from the open position to the closed position. The one or more portions of suture may also extend through one or more apertures formed on the first coupling portion 34 of the first arm assembly 12 and/or the second coupling portion 134 of the second arm assembly 14, such as aperture 175 formed on a portion of the second coupling portion 134 of the second arm assembly 14, as illustrated in FIG. 1C. When the atrial clip assembly 10 is placed in the closed position, the one or more portions of suture may be cut to be removed from the atrial clip assembly 10 via a slot in the shaft 210.

The position of the atrial clip assembly 10 may be adjusted relative to the shaft 210 using the coupling assembly 228. In particular, the first rotational assembly 232 may be coupled to a first adjustment portion 248 to rotatably displace the first rotational assembly 232 relative to the hub portion 229. In some embodiments, the first adjustment portion 248 may be an adjustment wheel 250 rotatably coupled to an internal portion of the housing portion 202, and a spring may bias the adjustment wheel 250 into frictional engagement with a portion of the housing portion 202 to prevent undesired rotation of the adjustment wheel 250. A portion of the adjustment wheel 250 may extend out a slot 252 formed in a portion of the housing portion 202 to allow the adjustment wheel 250 to be turned by a user. One or more portions of suture (not shown) may be coupled to the adjustment wheel 250 and to the base portion 234 of the first rotational assembly 232 (for example, through apertures 254) such that rotation of the adjustment wheel 250 may rotate the first rotational assembly 232 relative to the hub portion 229 about the axis 236.

In addition, the second rotational assembly 240 may be coupled to a second adjustment portion 256 to rotatably displace the second rotational assembly 240 relative to the first rotational assembly 232. In some embodiments, the second adjustment portion 256 may be an adjustment wheel 258 rotatably coupled to an internal portion of the housing portion 202, and a spring may bias the adjustment wheel 258 into frictional engagement with a portion of the housing portion 202 to prevent undesired rotation of the adjustment wheel 258. A portion of the adjustment wheel 258 may extend out a slot 260 formed in a portion of the housing portion 202 to allow the adjustment wheel 258 to be turned by a user. One or more portions of suture (not shown) may be coupled to the adjustment wheel 258 and to the base portion 242 of the second rotational assembly 240 (for example, through apertures 262) such that rotation of the adjustment wheel 258 may rotate the second rotational assembly 240 relative to the first rotational assembly 232 about the axis 244.

Figure 14:
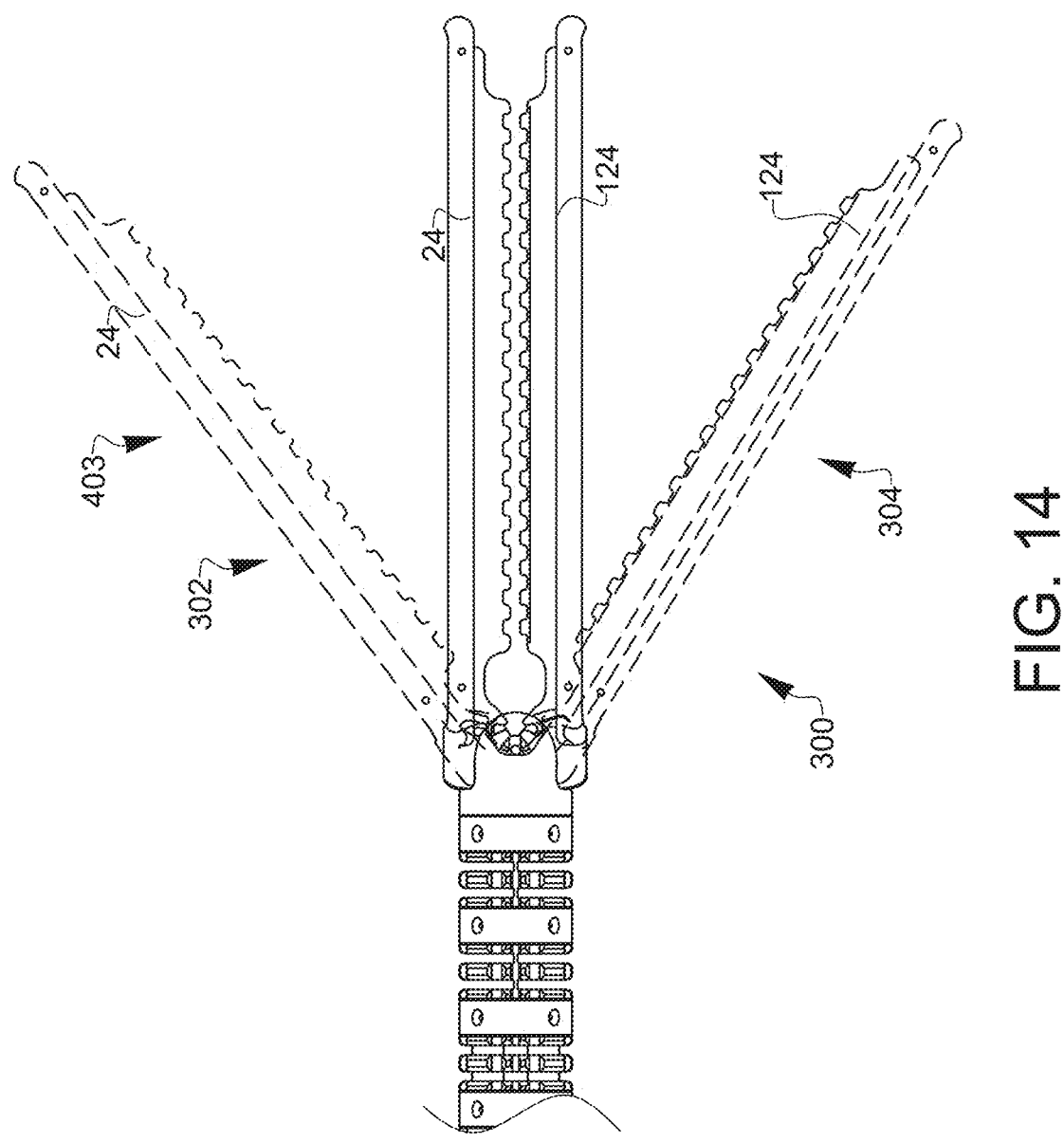
Figure 15:
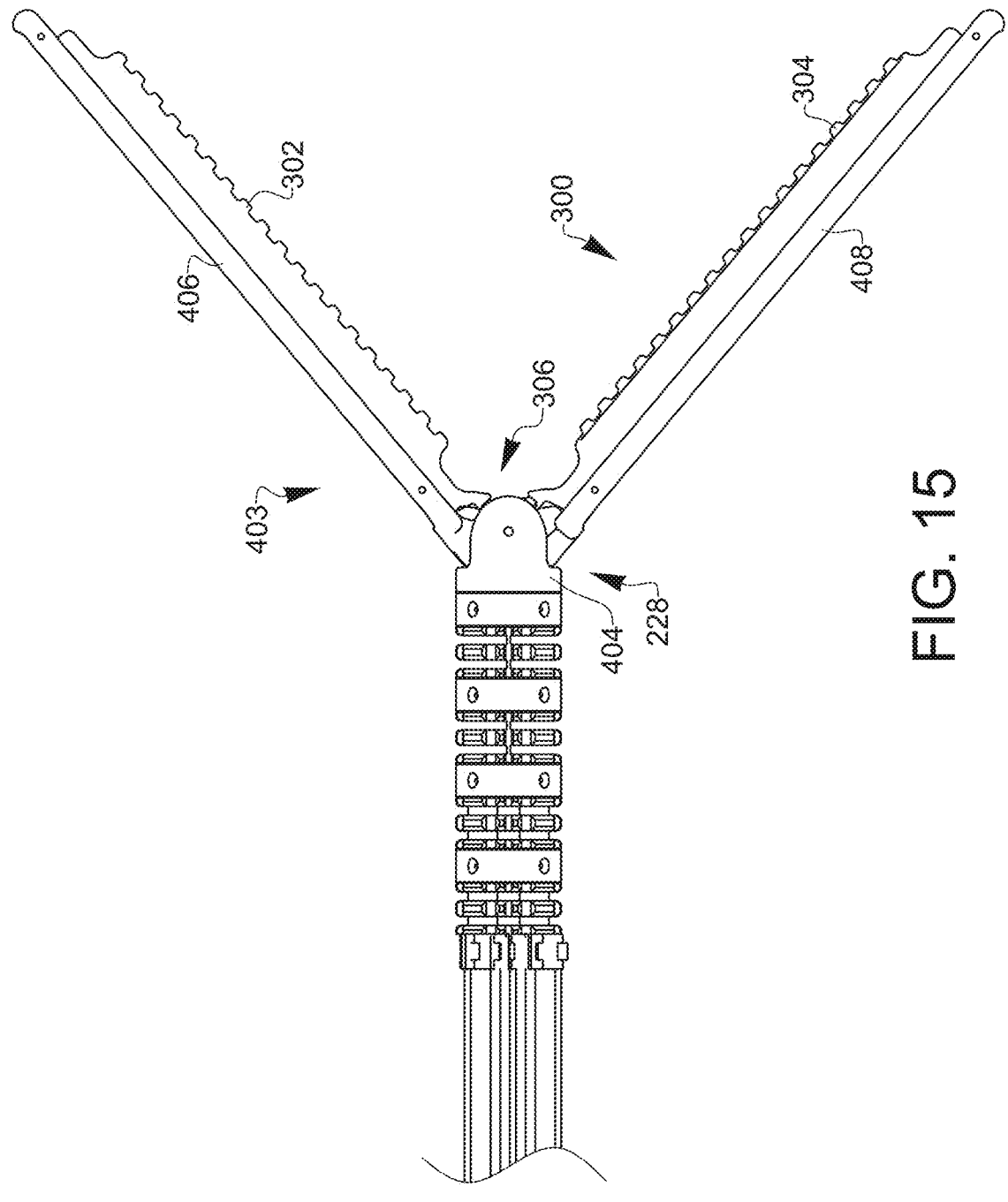
Figures 16, 17:
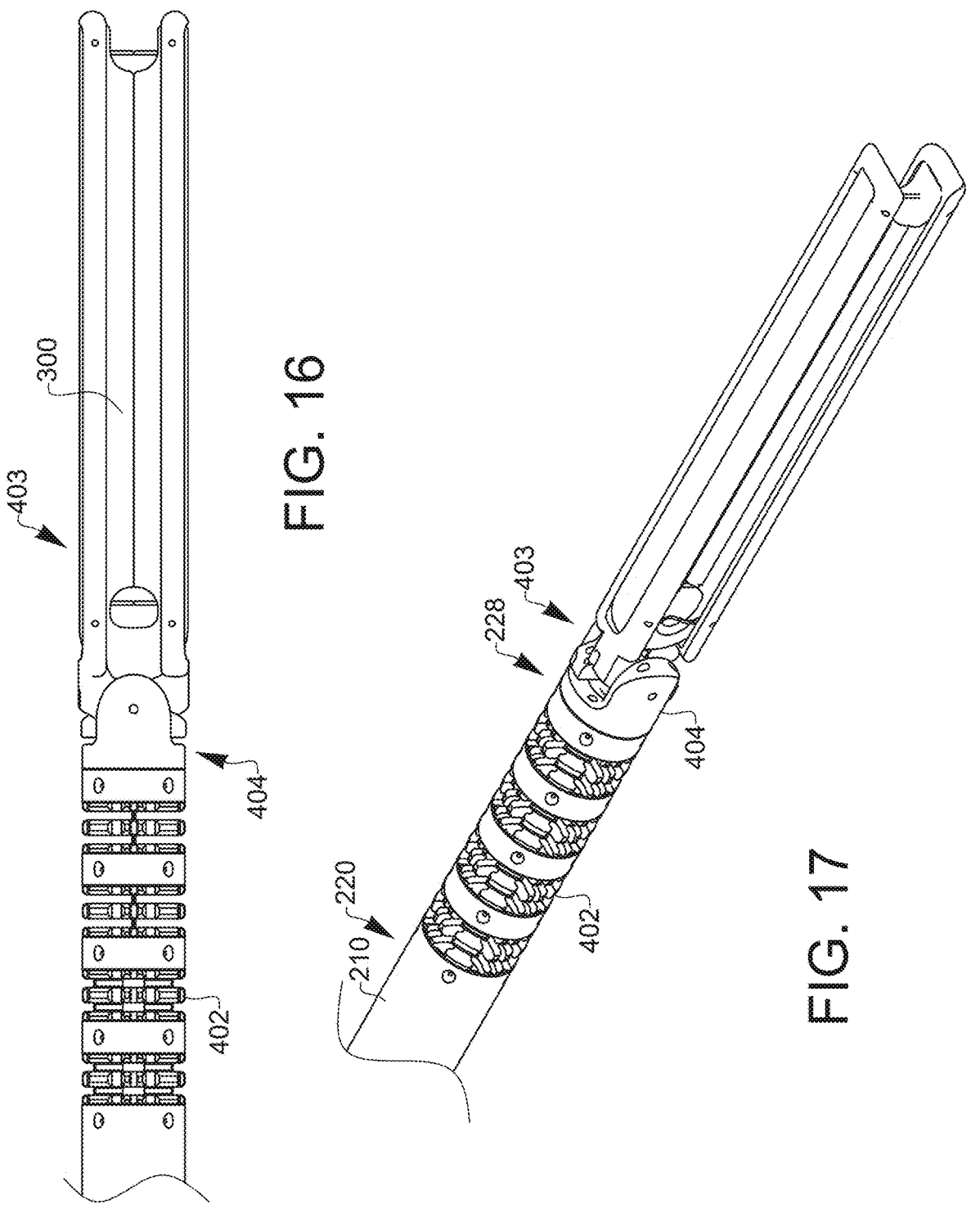
Figure 18A:
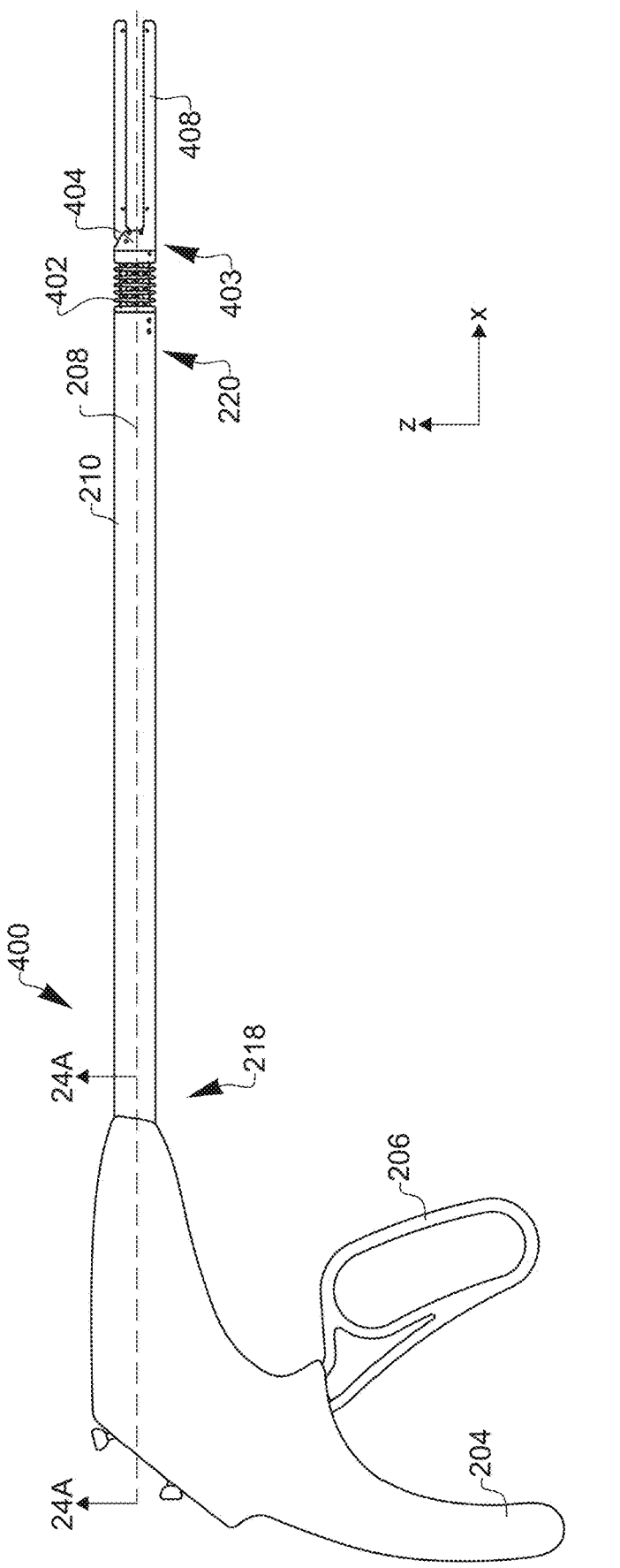
Figure 19:
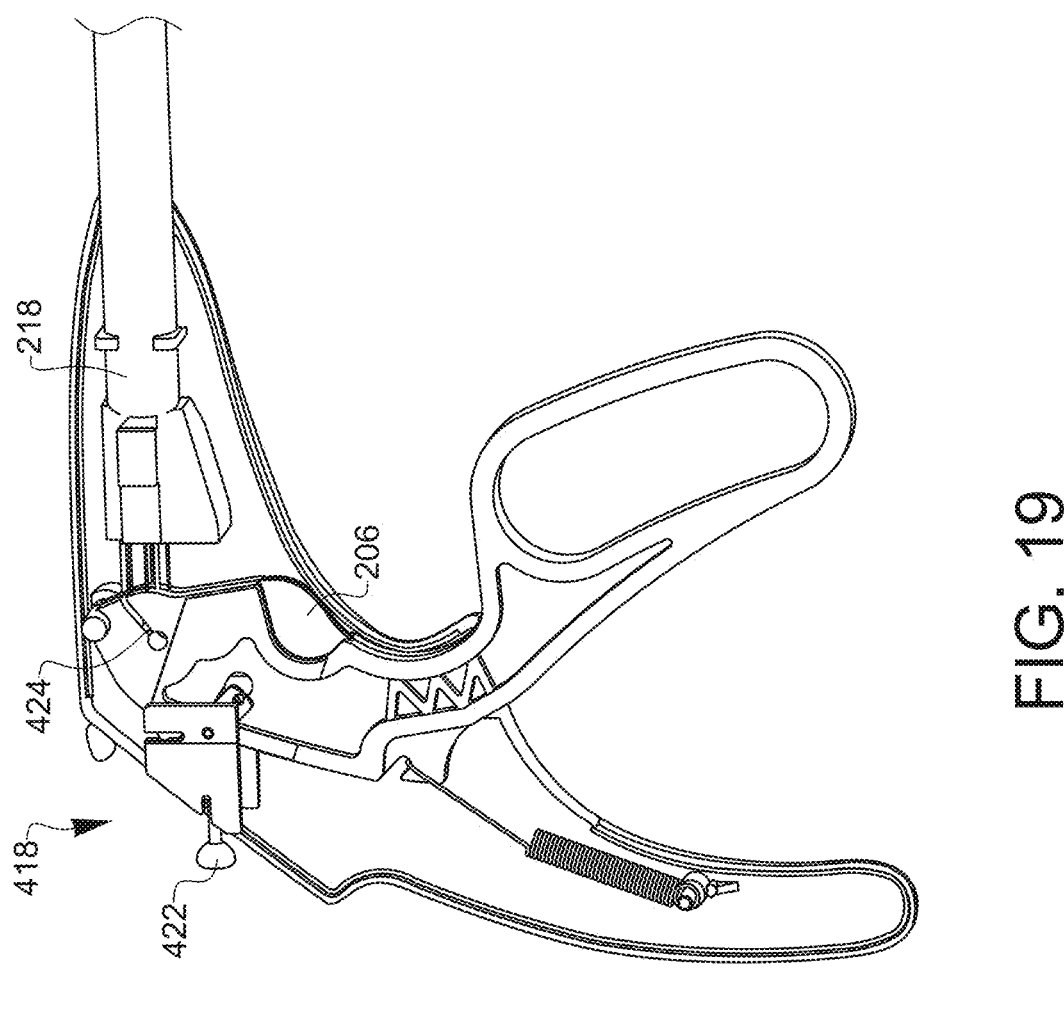
Figure 18B:
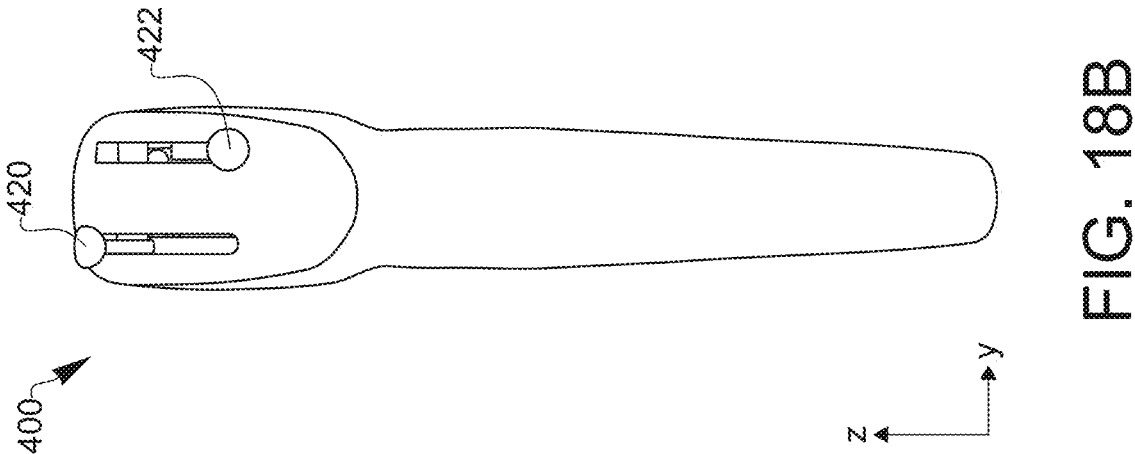

While the introducer device is 200 is discussed with reference to the atrial clip assembly 10, any clip assembly, such as the atrial clip assembly 300, may also be introduced and applied using the introducer device is 200. For example, FIG. 14 illustrates the jaw assembly 403 securing the atrial clip assembly 300 in the closed position and, in dashed lines, in the open position. FIG. 15 also illustrates the jaw assembly 403 securing the atrial clip assembly 300 in the open position.

Figures 28, 29:
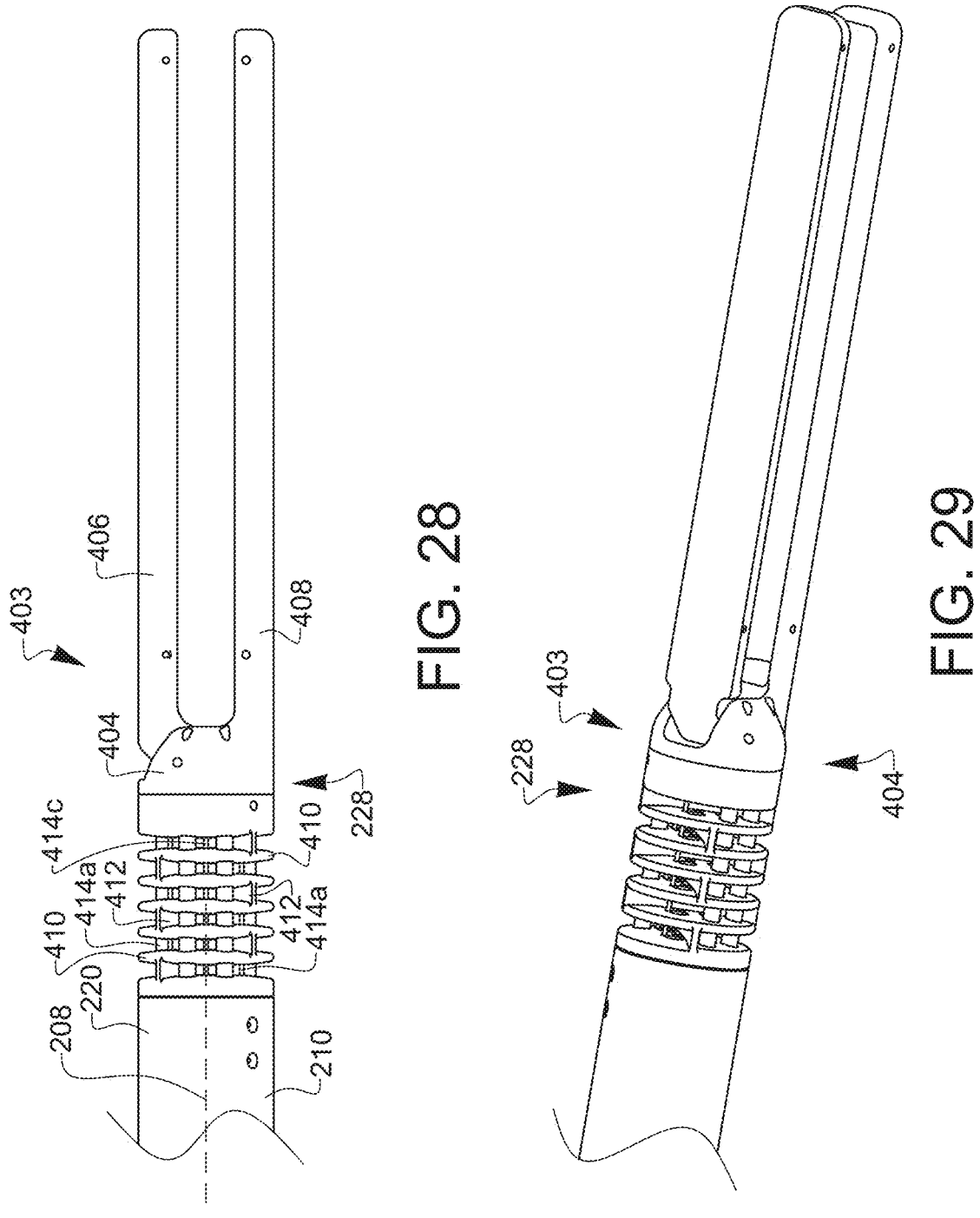
Figures 30E, 30F:
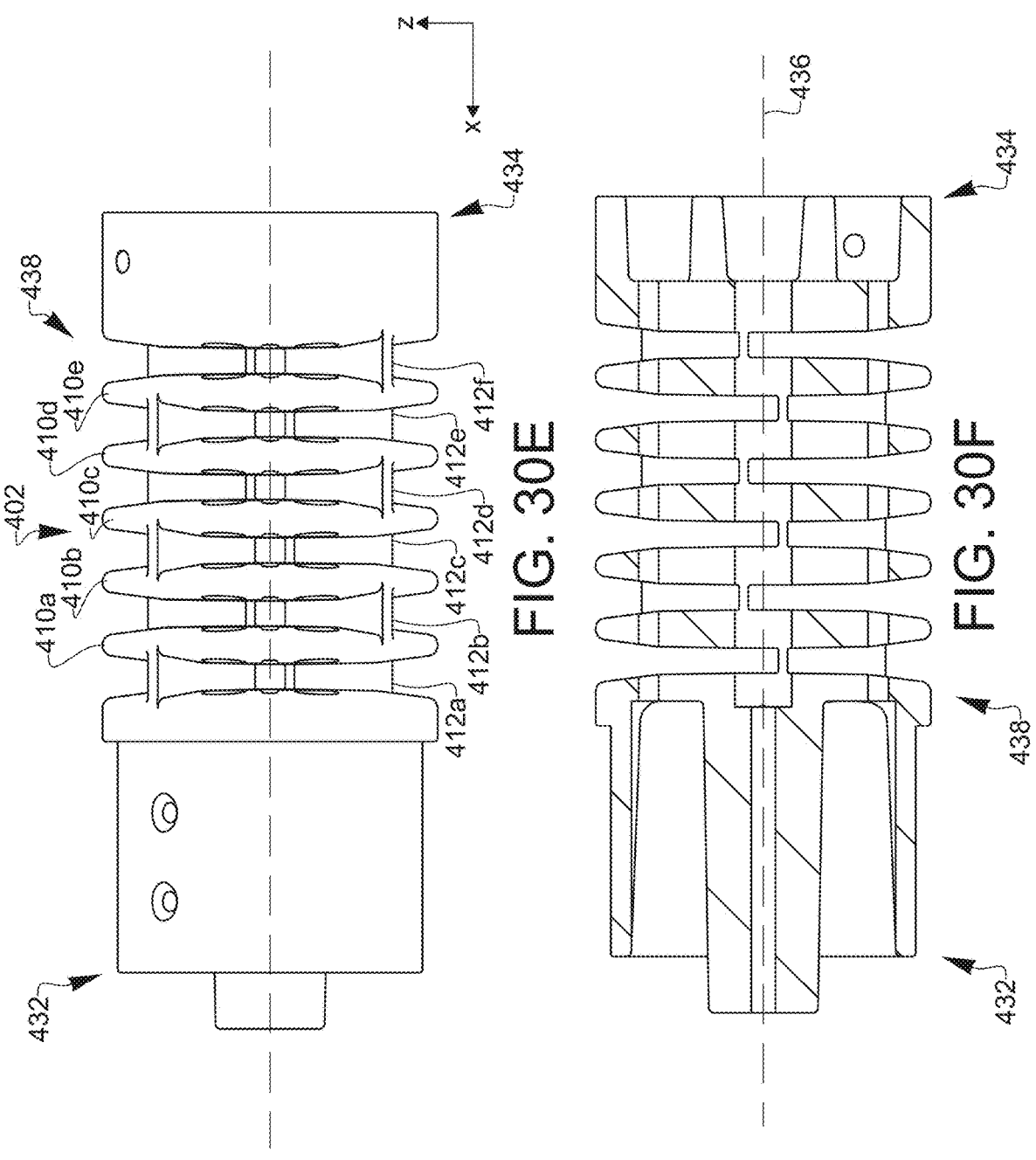
Figures 30G, 30H:
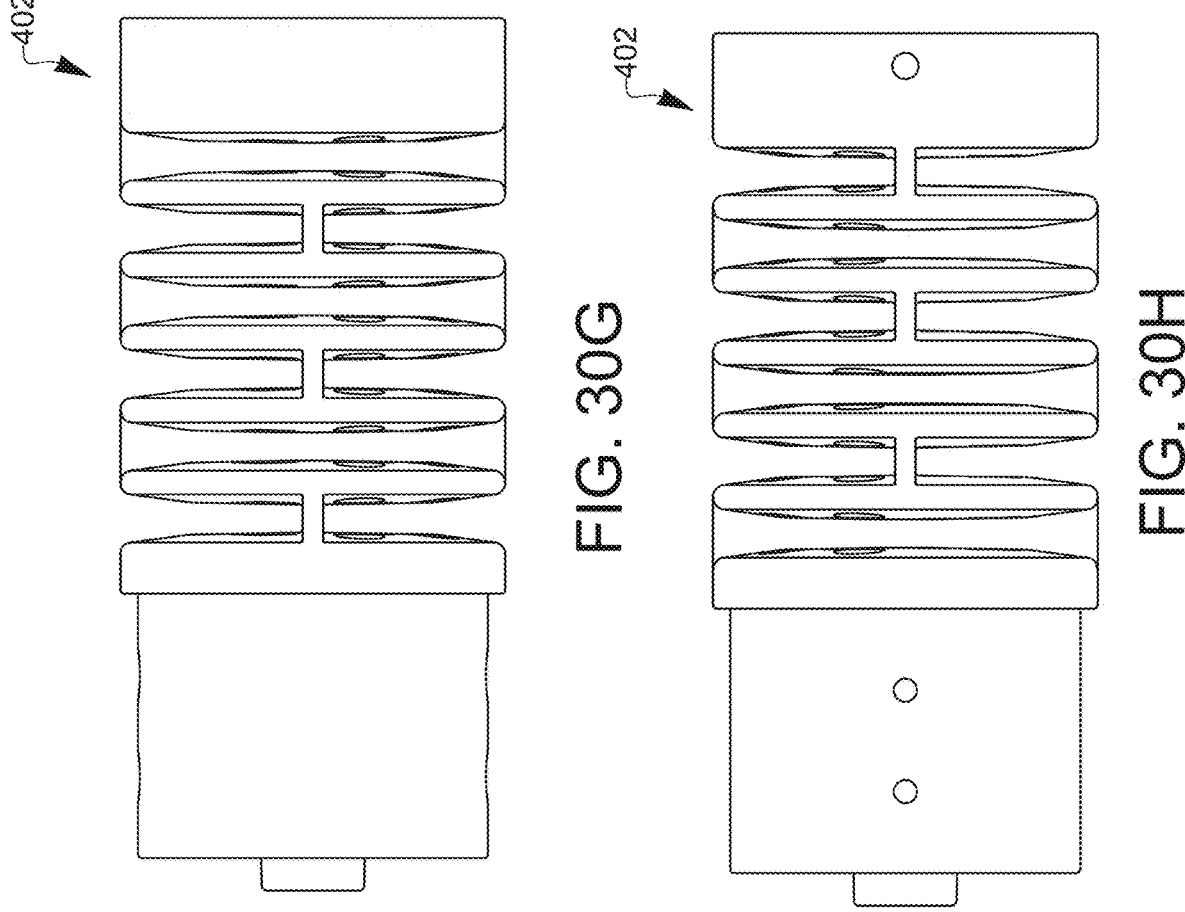
Figures 30I, 30J, 30K, 30L, 30M:
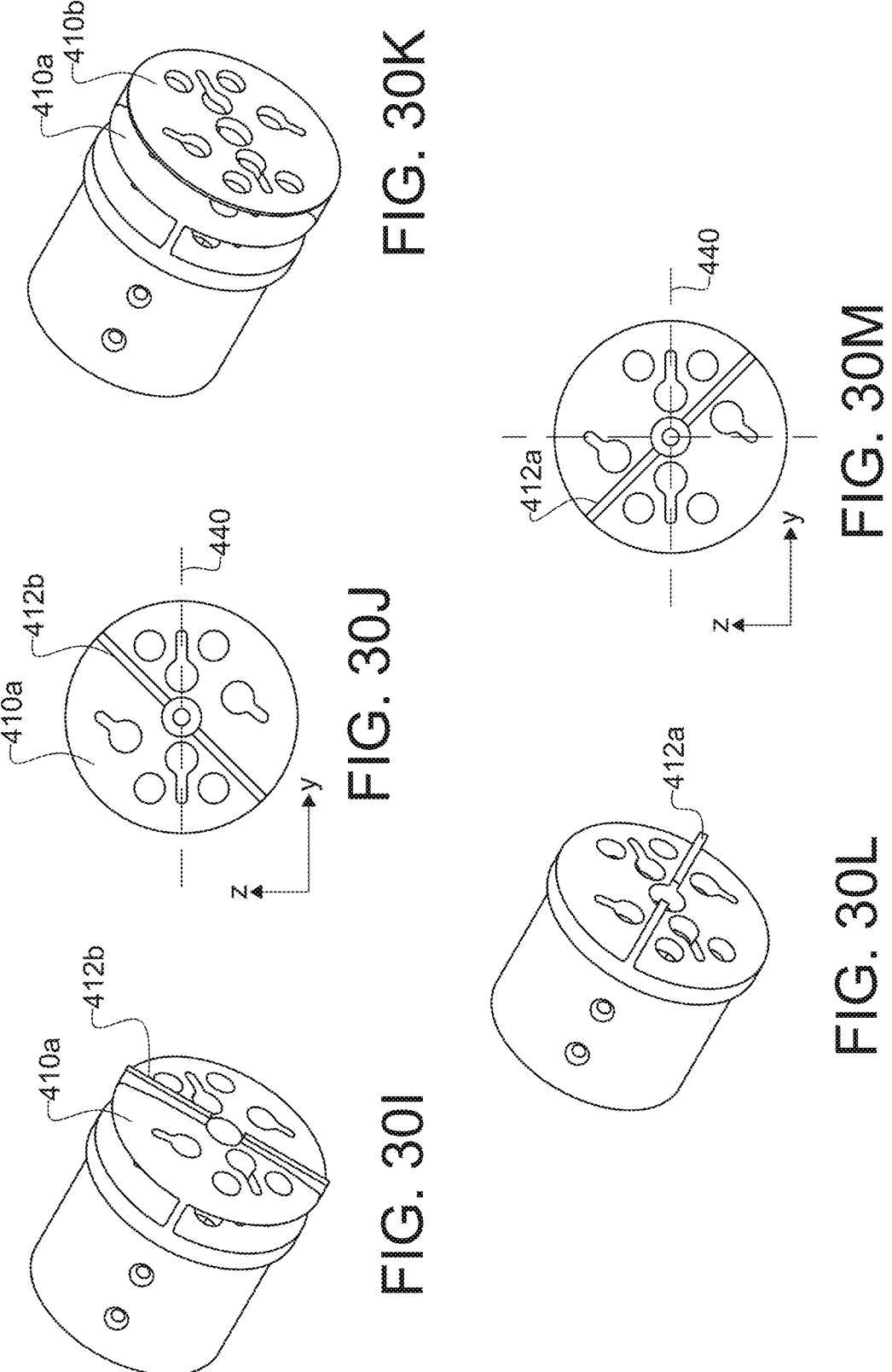
Figures 31A, 31B:
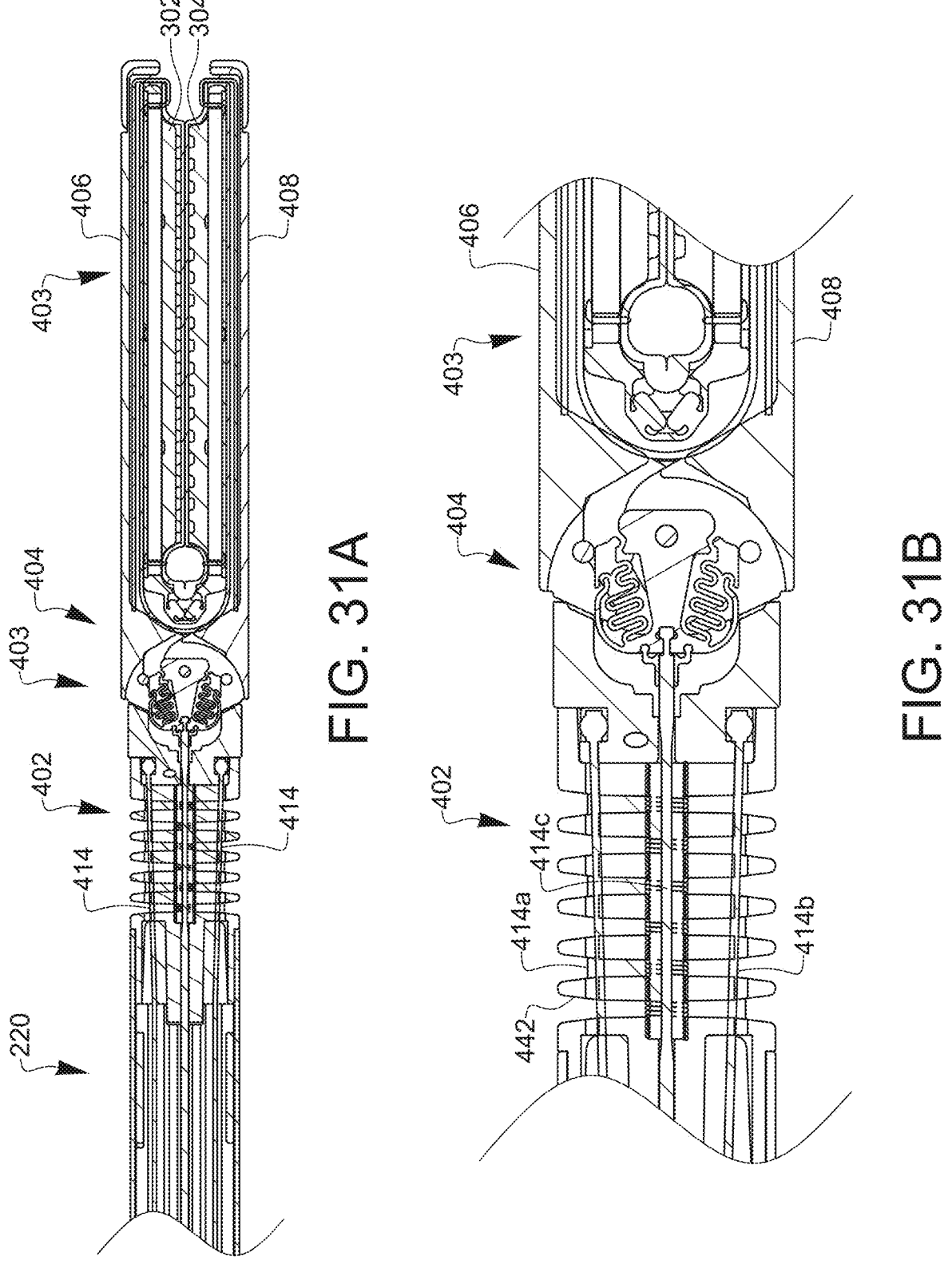
Figure 32A:
Figures 32B, 32C:
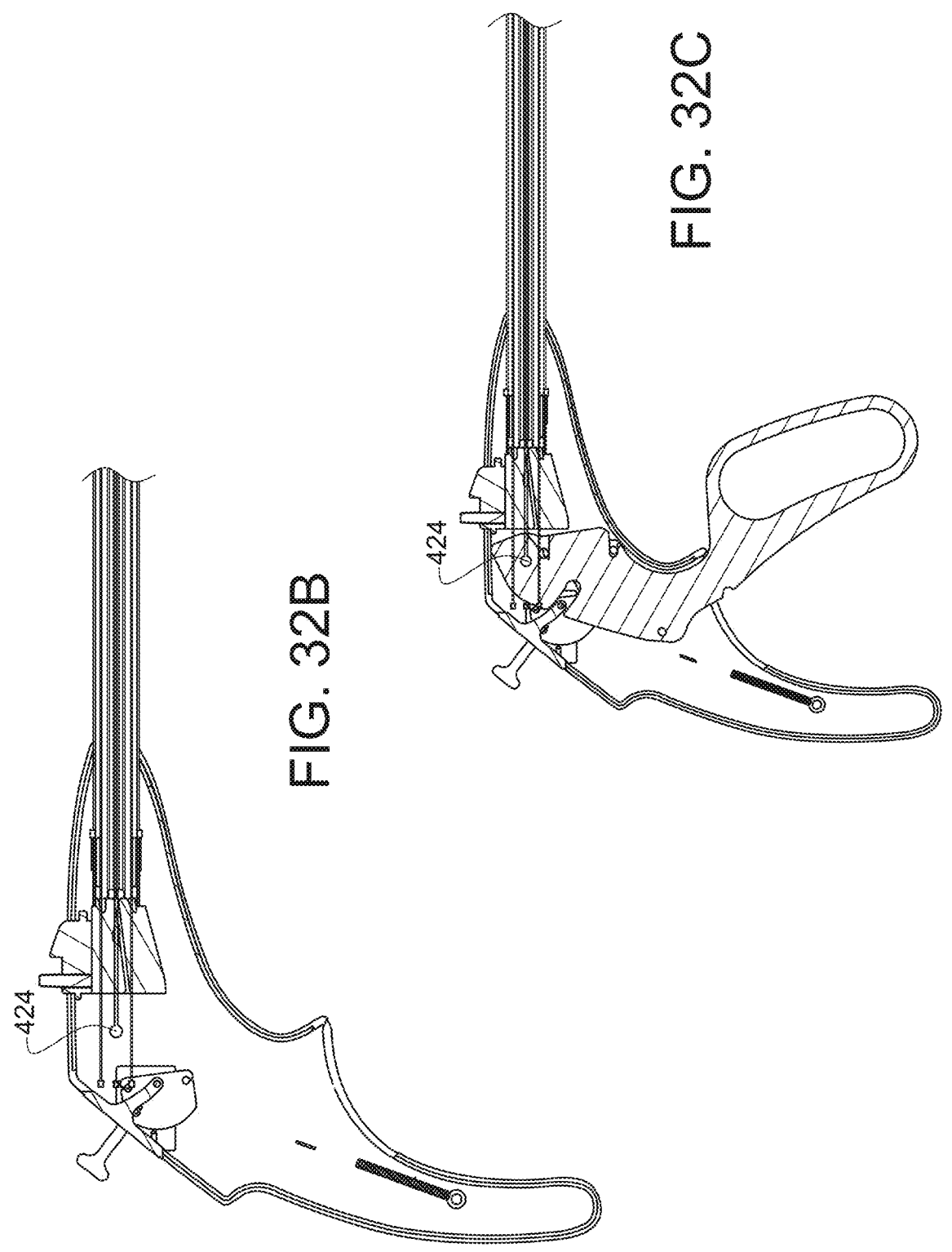
Figure 32D:
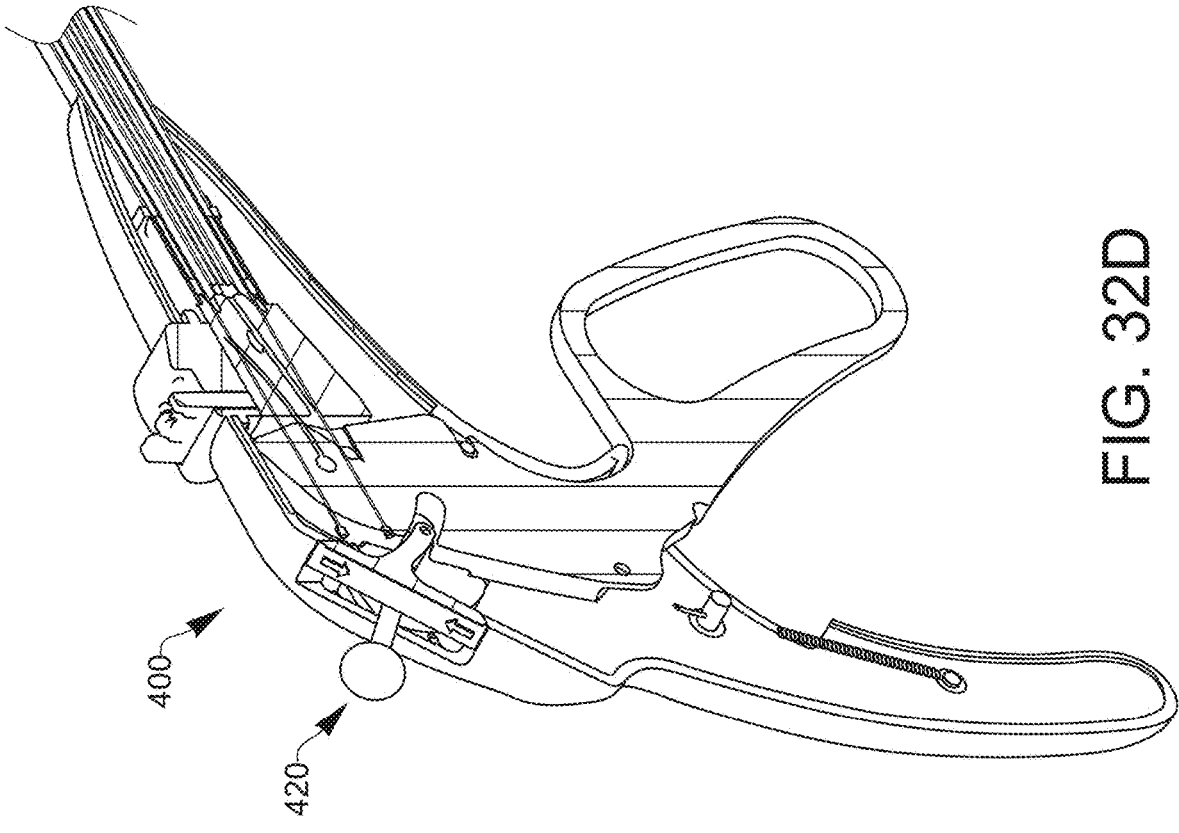
Figures 33A, 33B:
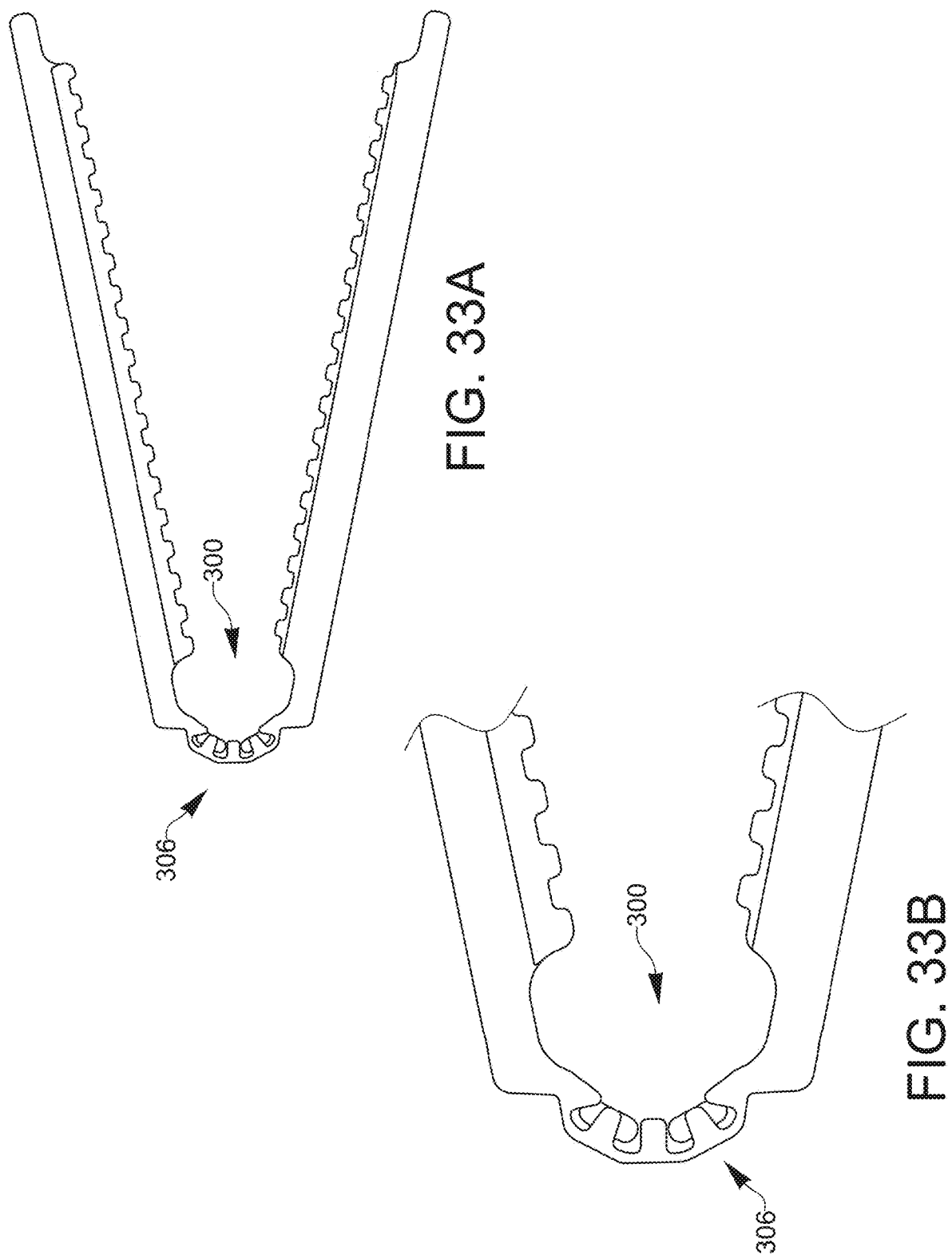
Figures 33C, 33D:
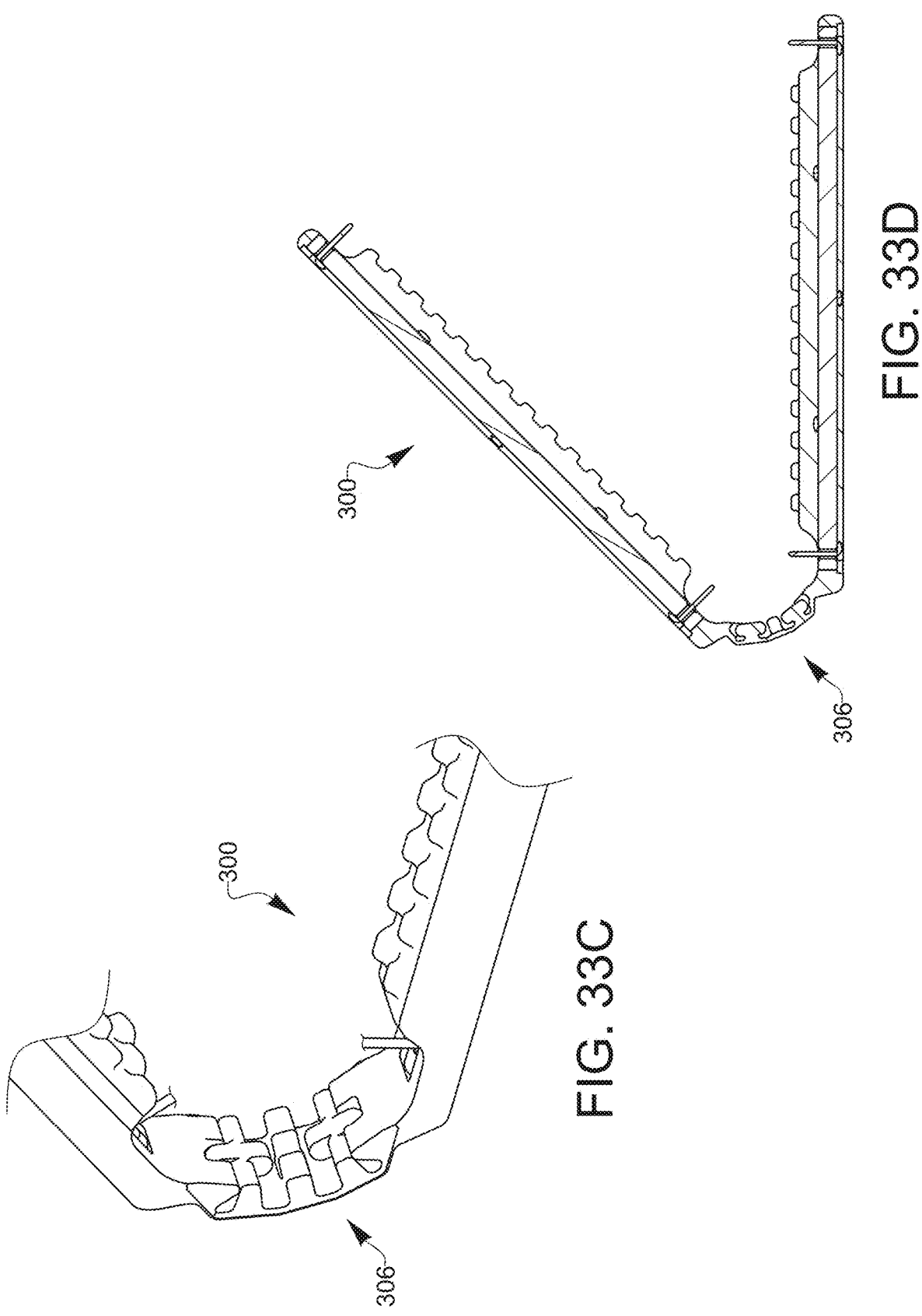
Figures 34A, 34B:
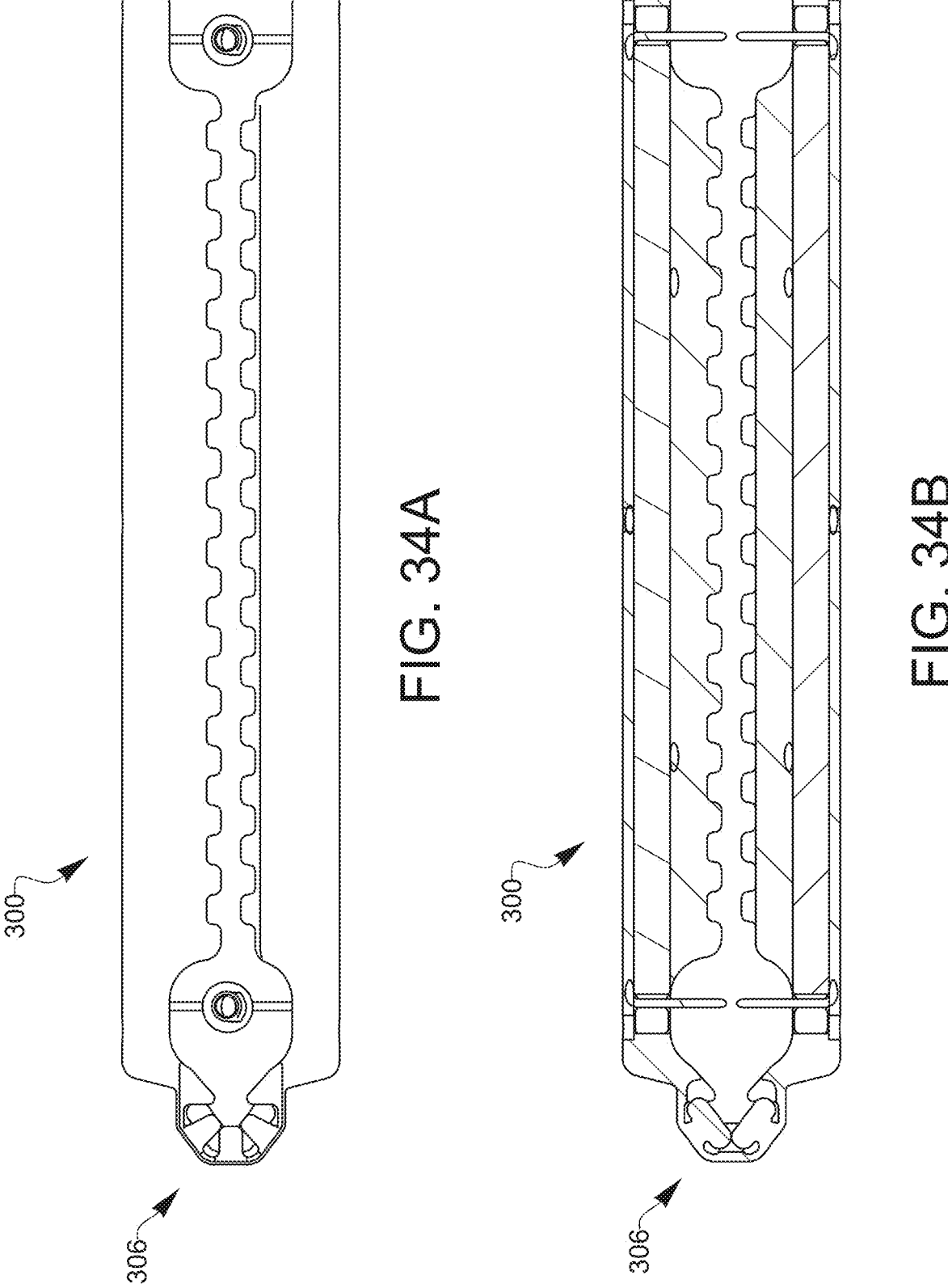

As illustrated in FIGS. 14 to 29, a further embodiment of an introducer device 400 is provided that may be similar to the introducer device 200, and specific features of the introducer device 400 that are similar or identical to those of the introducer device 200 will share the same reference numbers. In particular, FIGS. 16, 17, 18A to 18B, and 29 illustrate the introducer device 400 that may include a flexible coupling 402, and as illustrated in FIGS. 30A to 30M, the flexible coupling 402 may extend from a proximal end 432 to a distal end 434 along a coupling axis 436 that may be aligned with the shaft axis 208. The proximal end 432 of the flexible coupling 402 may be coupled to and/or disposed at or adjacent to the distal end 220 of the shaft 210. For example, as illustrated in FIG. 31A, all or a portion of the proximal end 432 of the flexible coupling 402 may have a cylindrical shape with a diameter equal to or slightly less than the diameter of portion of the internal surface at the distal end 220 of the shaft 210, and the all or portion of the proximal end 432 of the flexible coupling 402 may be received into the opening at the distal end 220 of the shaft 210. The distal end 434 of the flexible coupling 402 may be coupled to and/or disposed at or adjacent to a portion of a yoke portion 404, as illustrated in FIGS. 28, 31A, and 31B. The yoke portion 404 may be a portion of a coupling assembly 228 of a jaw assembly 403.

Referring to FIG. 30B, the flexible coupling 402 may include an intermediate portion 438 disposed between the proximal end 432 and the distal end 434, and the intermediate portion 438 may include a plurality of radial members 410 that are spaced along the coupling axis 436, and each of the plurality of radial members 410 may be identical. In some embodiments, each of the plurality of radial members 410 may be disk-shaped and may have a diameter equal to or approximately equal to the outer diameter of the shaft 210. The intermediate portion 438 may also include a plurality of axial walls 412 that are disposed between and/or extend from the plurality of radial members 410. In particular, a single one of the plurality of axial walls 412 may extend between adjacent radial members 410, and each of the plurality of axial walls 412 may be identical except for an orientation relative to a reference axis 440 (that extends through the coupling axis 436 and parallel to the Y-axis of the reference coordinate system of FIG. 30B, as illustrated in FIGS. 30J and 30M). In particular, each of the plurality of axial walls 412 may be planar and may have an equal or approximately equal "length" dimension that extends along the X-axis of the reference coordinate system of FIG. 30B, and each of the plurality of axial walls 412 may have a thickness that may range from approximately 50% to 100% of the thickness of each (or some) of the plurality of radial members 410. Each of the plurality of axial walls 412 may intersect the coupling axis 436, as illustrated in the cross-sectional views of FIGS. 301, 30J, 30L, and 30M. In addition, each of the plurality of axial walls 412 may have an orientation relative to the reference axis 440 that regularly alternates between two positions relative to each radial member 410. For example, a first 412*a* of the plurality of axial walls 412 that may extend proximally from a proximal surface of a first of the plurality of radial members 410*a* may form an angle of 135 degrees with the reference axis 440, as illustrated in FIG. 30M. Further, a second 412*b* of the plurality of axial walls 412 that may extend distally from a distal surface of the first of the plurality of radial members 410*a* may form an angle of 45 degrees with the reference axis 440, as illustrated in FIG. 30J. This alternating configuration of axial walls 412 that extend from opposite surfaces of each of the plurality of radial members 410a may repeat for at least a portion of the plurality of radial members 410a in the intermediate portion 438, and in some embodiments, may repeat for each of the plurality of radial members 410a in the intermediate portion 438. For example, with respect to a second of the plurality of radial members 410b, the second 412b of the plurality of axial walls 412 may extend proximally from a proximal surface, which may form an angle of 45 degrees with the reference axis 440, and a third 412c of the plurality of axial walls 412 may extend distally from a distal surface of second of the plurality of radial members 410b, and the third 412c of the plurality of axial walls 412 may be aligned with the first 412a of the plurality of axial walls 412 when viewed along the coupling axis 436. Similarly, a fifth 412e of the plurality of axial walls 412 may be aligned with the first 412a and the third 412c of the plurality of axial walls 412 when viewed along the coupling axis 436, and a fourth 412d and a sixth 412f of the plurality of axial walls 412 may be aligned with the second 412b of the plurality of axial walls 412 when viewed along the coupling axis 436. As illustrated in FIGS. 30A, 30C, and 30D, each of the plurality of radial members 410b may include two or more apertures 442, and each of the two or more apertures 442 may be configured such that corresponding apertures 442 through the plurality of radial members 410b may be aligned along axes that extend parallel to the X-axis of the reference coordinate system of FIG. 30B.

The flexible coupling 402 may be manufactured, fabricated, or comprised of a flexible material that may allow the distal end 434 of the flexible coupling 402 to bend about the fixed proximal end 432 of the flexible coupling 402. For example, the flexible coupling 402 may be made or manufactured as a single, unitary part from a flexible material, such as a plastic material (e.g., a silicone material). In other embodiments, the flexible coupling 402 may be made from an assembly of two or more components.

Referring to FIGS. 28, 31A, and 31B, the jaw assembly 403 may include the coupling assembly 228, which may include the yoke portion 404. The jaw assembly 403 may further include a first jaw 406 that may pivotably coupled to a first portion the yoke portion 404. The first jaw 406 may be configured to be releasably coupled to the first arm assembly 12, 302 of the atrial clip assembly 10, 300. The jaw assembly 403 may also include a second jaw 408 the may be pivotably coupled to a second portion of the yoke portion 404. The second jaw 408 may be configured to be releasably coupled to the second arm assembly 14, 304 of the atrial clip assembly 10, 300.

The jaw assembly 403 may be displaceable between an open position, illustrated in FIG. 45B, and a closed position, illustrated in FIG. 45A, as will be described in more detail below. In some embodiments, the yoke portion 404 may be integrally formed with the second jaw 408 such that the first jaw 406 pivots relative to the yoke portion 404 and the first jaw 406. In other embodiments, such as the embodiments of FIGS. 45A and 45B, the yoke portion 404 may be a separate component from the first jaw 406 and the second jaw 408.

Figures 49A, 49B:
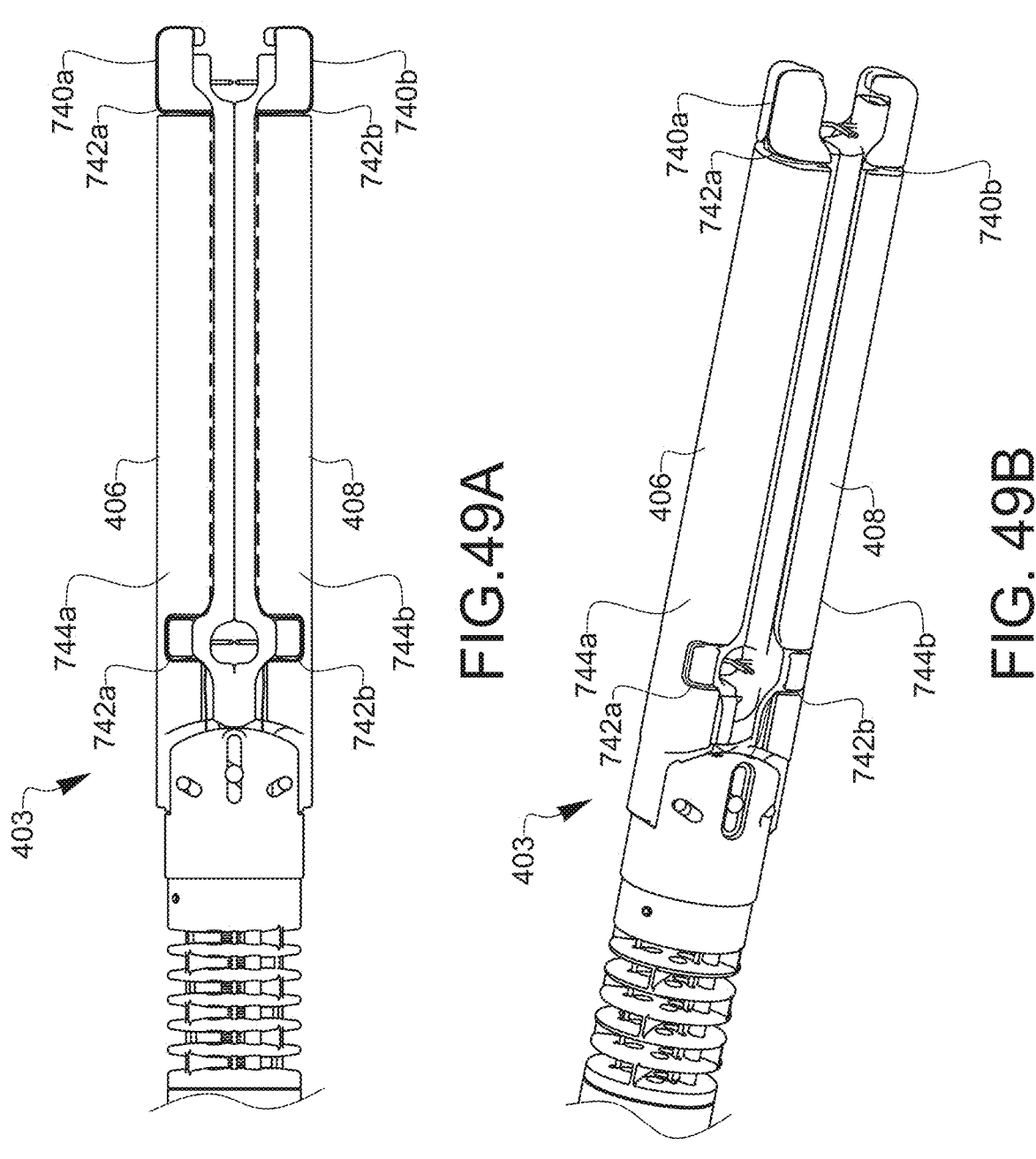
FIGS. 49A and 49B illustrate the atrial clip assembly releasably coupled to the jaw assembly.

As illustrated in FIGS. 49A and 49B, the first arm assembly 12, 302 of the atrial clip assembly 10, 300 may be releasably coupled to the first jaw 406 with one or more portions of suture. In particular, a first coupling suture 740a may be routed along one or more channels 742a formed on or along an outer surface 744a of the first jaw 406. A distal end portion of the first coupling suture 740a may be coupled to a portion of the first arm assembly 12, 302 of the atrial clip assembly 10, 300 or a portion (i.e., a distal portion) of the sheath 444 covering the first arm assembly 12, 302. A proximal end portion of the first coupling suture 740a may extend through the shaft 210 and be secured to or disposed at any suitable location of the introducer device 200, 400. In addition, the second arm assembly 14, 304 of the atrial clip assembly 10, 300 may be releasably coupled to the second jaw 406 with one or more portions of suture. In particular, a second coupling suture 740b may be routed along one or more channels 742b formed on or along an outer surface 744b of the second jaw 406. A distal end portion of the second coupling suture 740b may be coupled to a portion of the second arm assembly 14, 304 of the atrial clip assembly 10, 300 or a portion (i.e., a distal portion) of the sheath 444 covering the second arm assembly 14, 304. A proximal end portion of the second coupling suture 740b may extend through the shaft 210 and be secured to or disposed at any suitable location of the introducer device 200, 400.

In this manner, the first arm assembly 12, 302 of the atrial clip assembly 10, 300 may be releasably coupled to the first jaw 406 and the second arm assembly 14, 304 of the atrial clip assembly 10, 300 may be releasably coupled to the second jaw 406 when the jaw assembly 403 is displaced from the open position to the closed position. Further, releasing the first coupling suture 740a from the first jaw 406 releases the first arm assembly 12, 302 from the first jaw 406 and releasing the second coupling suture 740b from the second jaw 408 releases the second arm assembly 14, 304 from the second jaw 408.

Figures 20A, 20B:
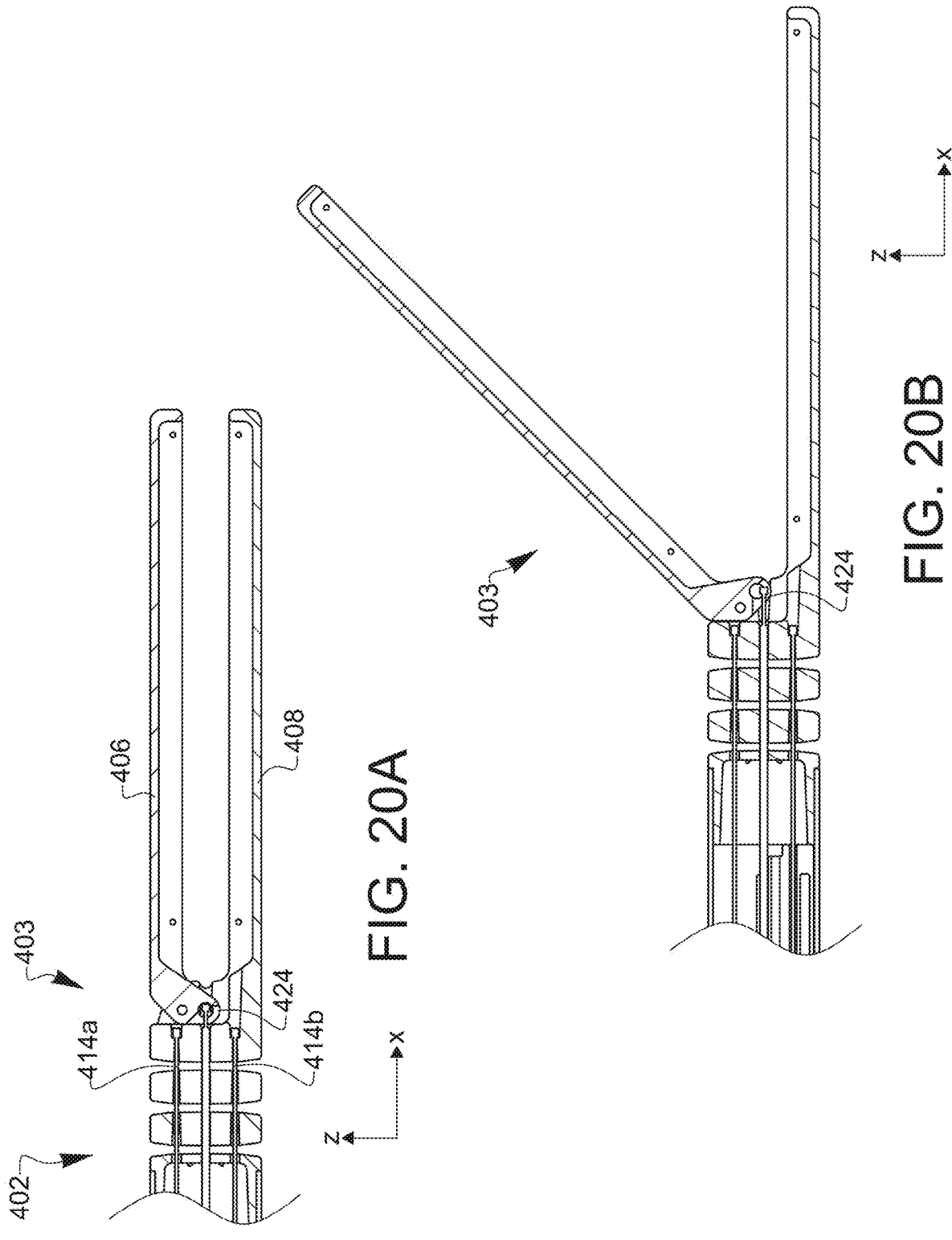
Figures 21, 22:
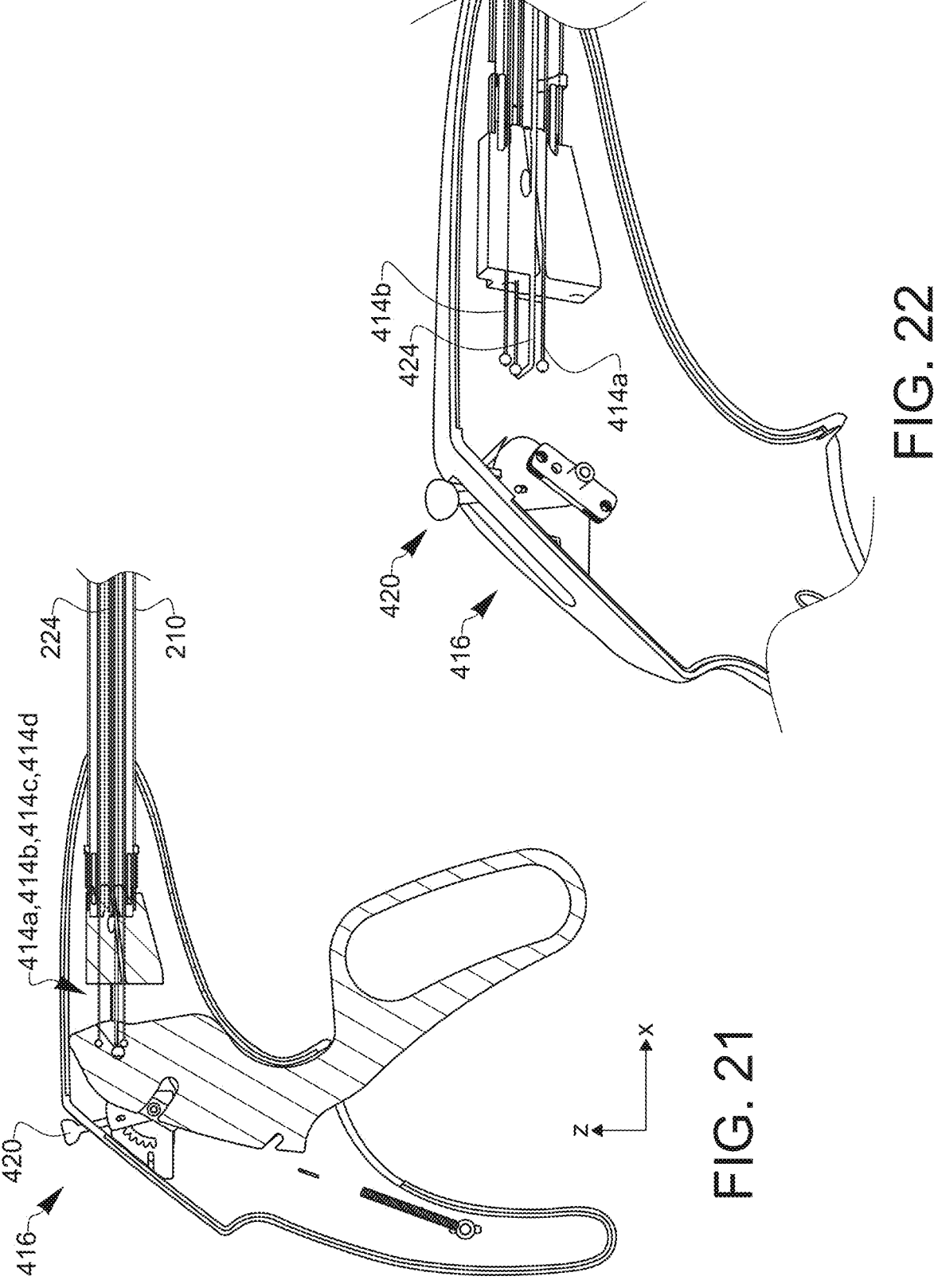
Figures 23, 24:
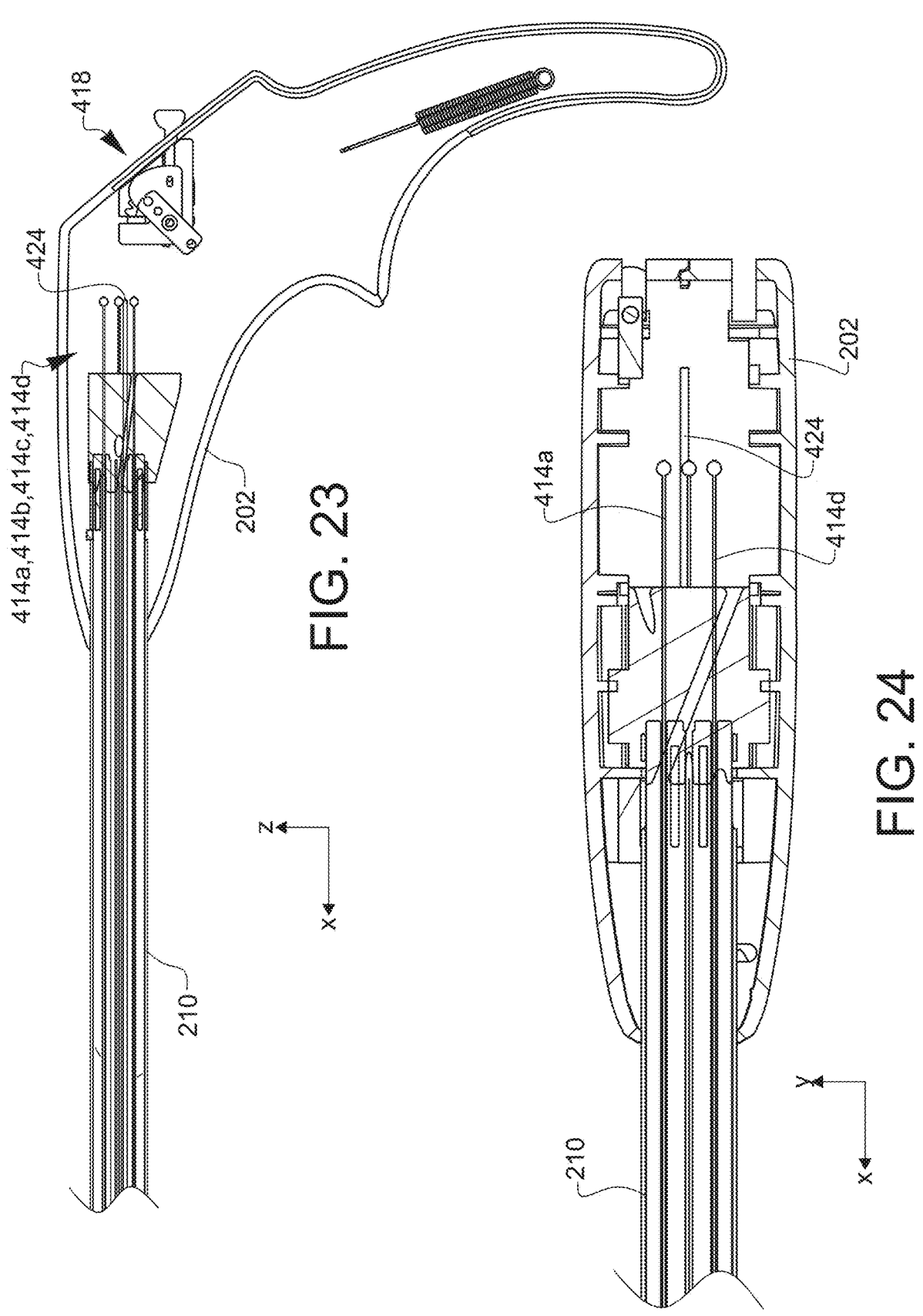
Figure 25:
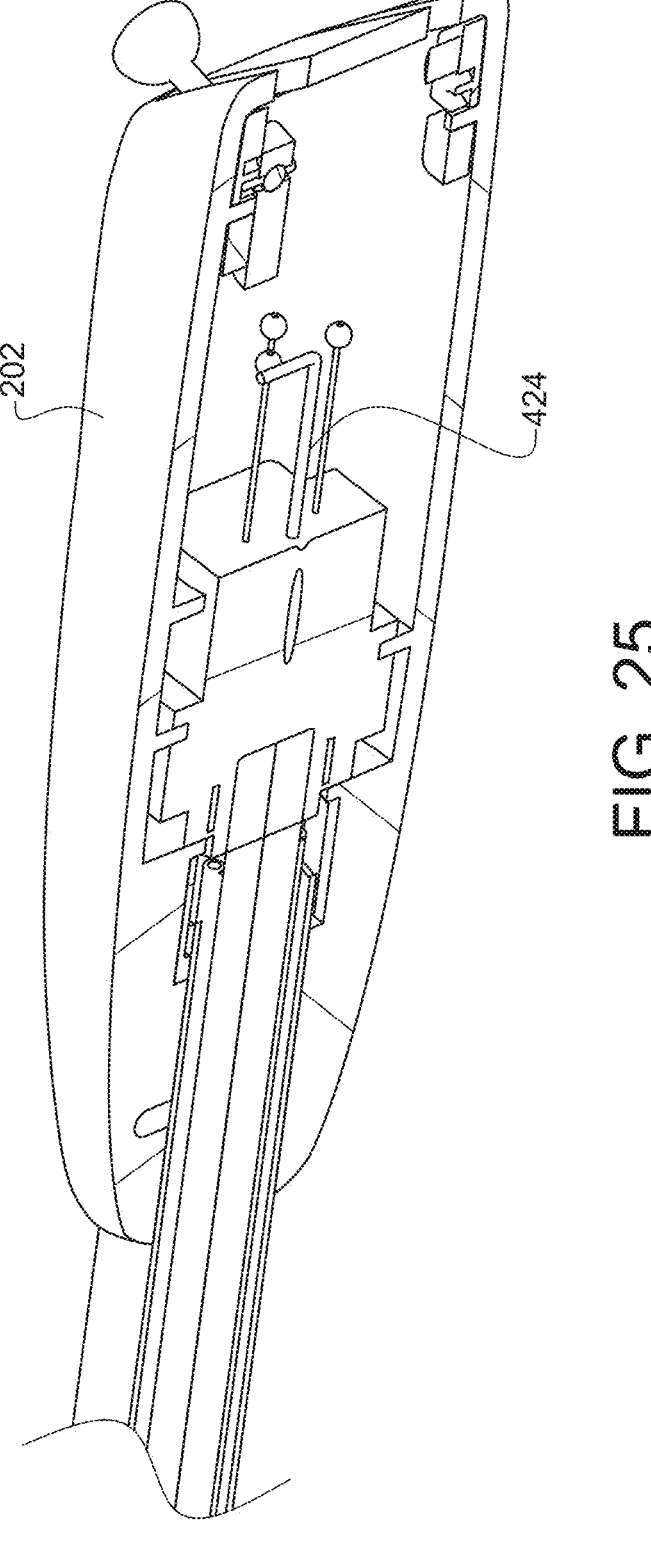
Figures 26, 27:
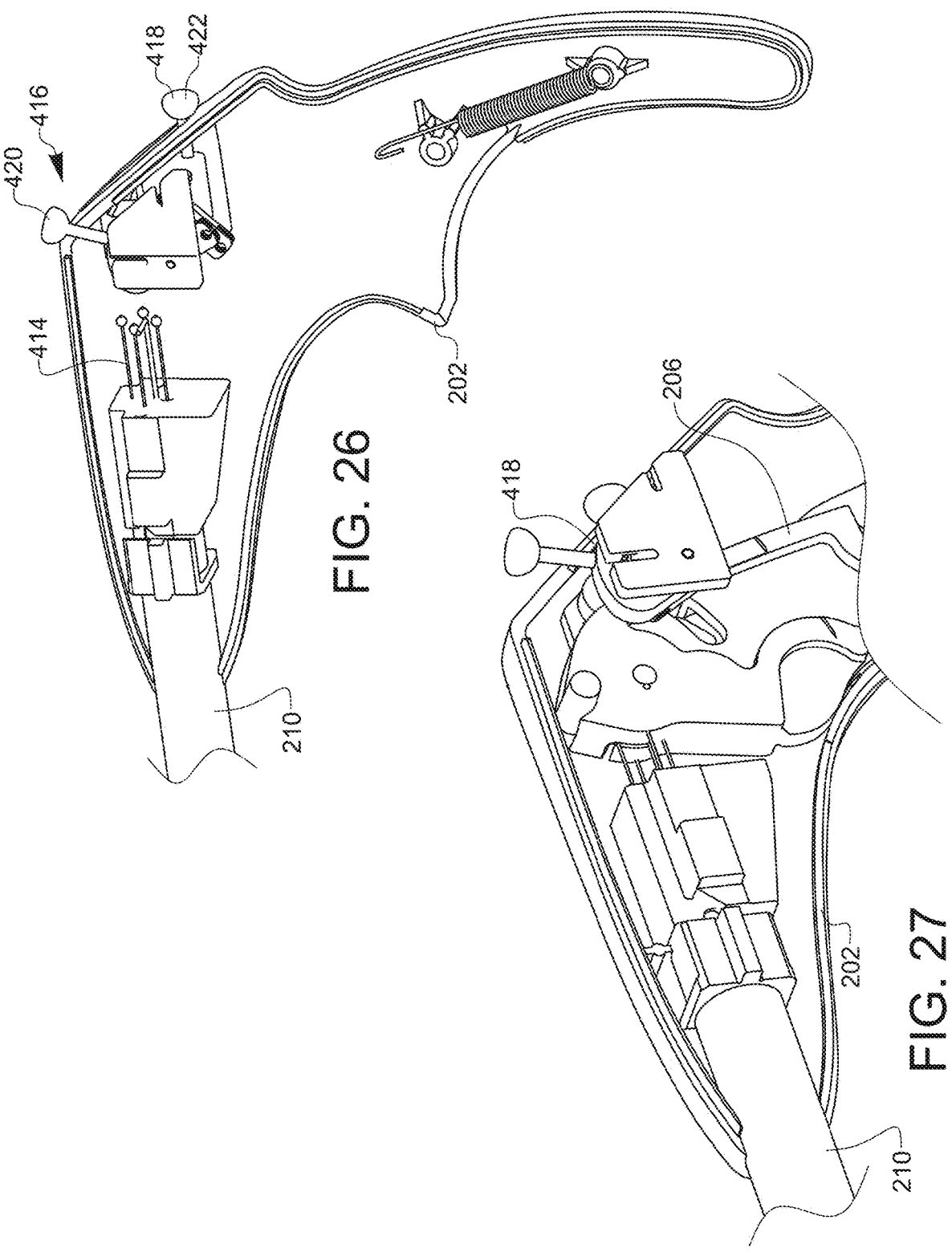

Referring to FIG. 28, two or more control wires 414a, 414b, 414c, 414d may each extend from a proximal end to a distal end, and a portion of each may extend through the interior portion 224 (see FIG. 21) of the shaft 210. The two or more control wires 414a, 414b, 414c, 414d may each extend through corresponding apertures 442 of each of the plurality of radial members 410b, as illustrated in FIG. 31B. With reference to FIG. 20A, the distal end of each control wire 414a, 414b, 414c, 414d may be coupled to a corresponding portion of the jaw assembly 403 (i.e., the first jaw 406 and/or the second jaw 408). Further, with reference to FIG. 26, the proximal end of each control wire 414a, 414b, 414c, 414d may be coupled to a corresponding portion of a first control lever assembly 416 and/or a second control lever assembly 418. For example, pivoting a lever 420 of the first control lever assembly 416 may displace the distal end of a corresponding one or more of the control wires 414a, 414b, 414c, 414d, thereby displacing the jaw assembly 403, by virtue of the flexible coupling 402, in a first direction relative to the distal end 220 of the shaft 210. Further, pivoting a lever 422 of the second control lever assembly 418 may displace the distal end of a corresponding one or more of the control wires 414a, 414b, 414c, 414d, thereby displacing the jaw assembly 403, by virtue of the flexible coupling 402, in a second direction relative to the distal end 220 of the shaft 210. Thus, by manipulating the first control lever assembly 416 and/or the second control lever assembly 418, the orientation or position of the jaw assembly 403 relative to the distal end 220 of the shaft 210 may be adjusted during a procedure by a surgeon. In some embodiments, the proximal end of one or more control wires 414a, 414b, 414c, 414d may be coupled to a corresponding portion of the actuation lever 206 and the orientation or position of the jaw assembly 403 relative to the distal end 220 of the shaft 210 may be changed by pivoting the actuation lever 206. FIGS. 19, 21 to 27, and 32A to 32D show various views of the first control lever assembly 416 and/or the second control lever assembly 418 with portions of the housing portion 202, and various other components, omitted for clarity.

Referring to FIG. 20A, an actuation wire 424 may extend from a proximal end to a distal end, and a portion of may extend through the interior portion 224 (see FIG. 21) of the shaft 210. The distal end of the actuation wire 424 may be coupled to a corresponding portion of the jaw assembly 403 (i.e., the first jaw 406). Further, with reference to FIGS. 19, 32C, and 32D, the proximal end of the actuation wire 424 may be coupled to a corresponding portion of an actuation lever 206. So configured, the atrial clip assembly 10, 300 may be coupled to the jaw assembly 403 and introduced to the treatment area in an open position of the jaw assembly 403 (illustrated in FIG. 20B). When the jaw assembly 403 has been positioned as desired (in the manner previous explained), the surgeon may close the jaw assembly 403 by displacing the actuation lever 206 from the first lever position (illustrated in FIG. 18A) to the second lever position, in which the actuation lever is pivoted towards the grip portion 204. Such a displacement distally displaces the distal end of the actuation wire 242, which may be coupled to a portion of the first jaw 406, which pivots the first jaw 406 towards the second jaw 208, thereby closing the jaw assembly 403, and the atrial clip assembly 10, 300 coupled to the jaw assembly 403.

Figure 37A:
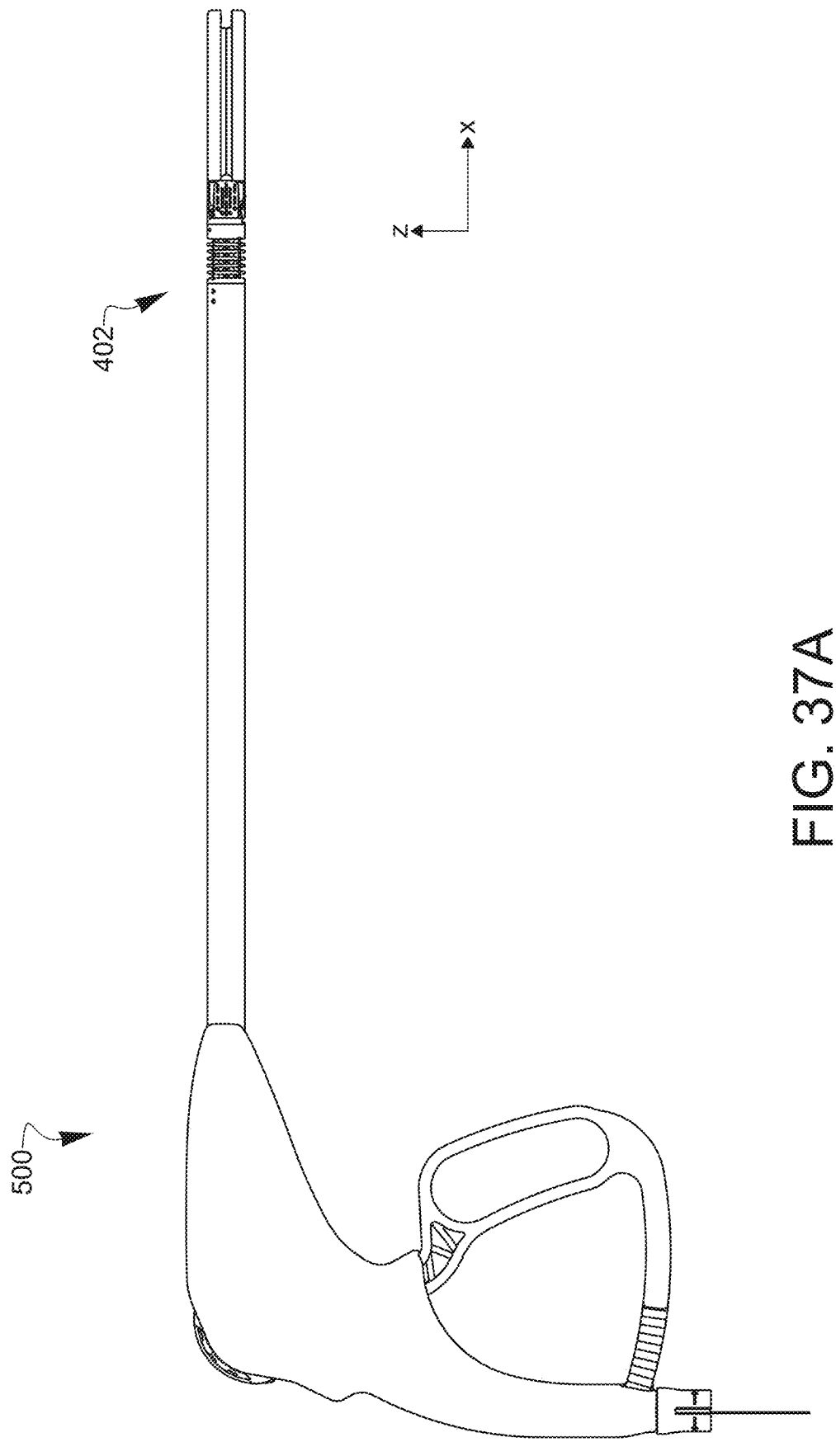
FIGS. 37A to 37C illustrate various views of further embodiments of an introducer device for the atrial clip assembly.
Figure 37B:
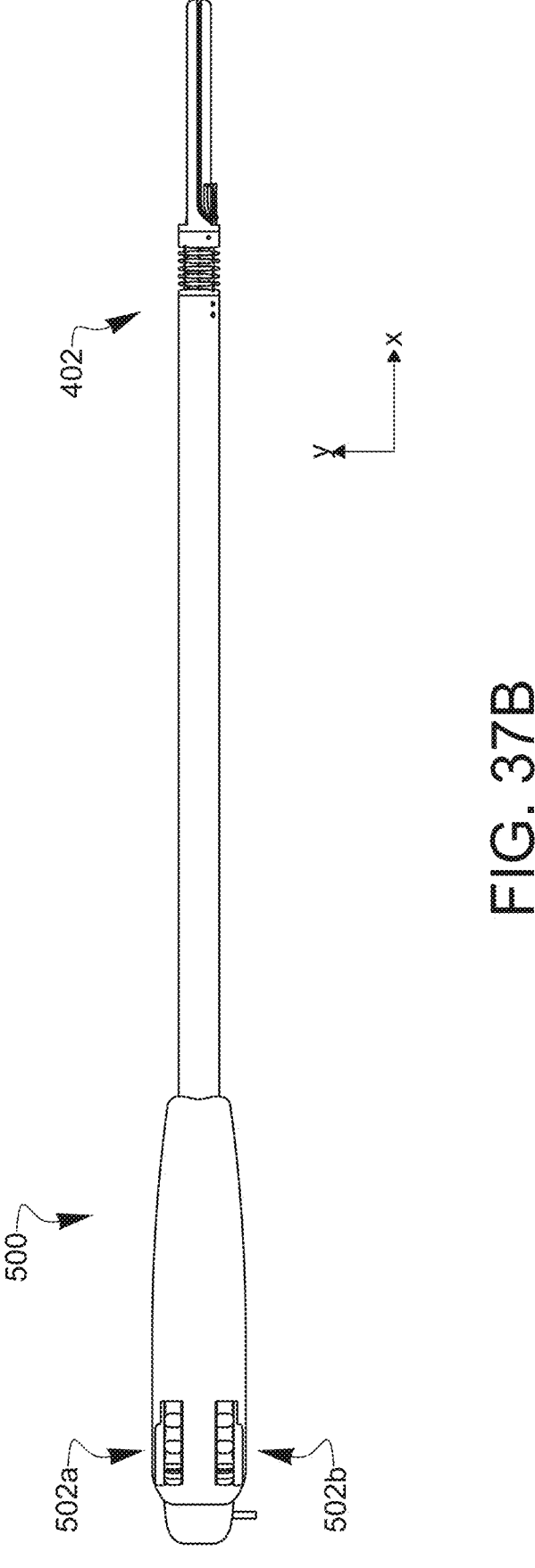
Figures 37C, 37D:
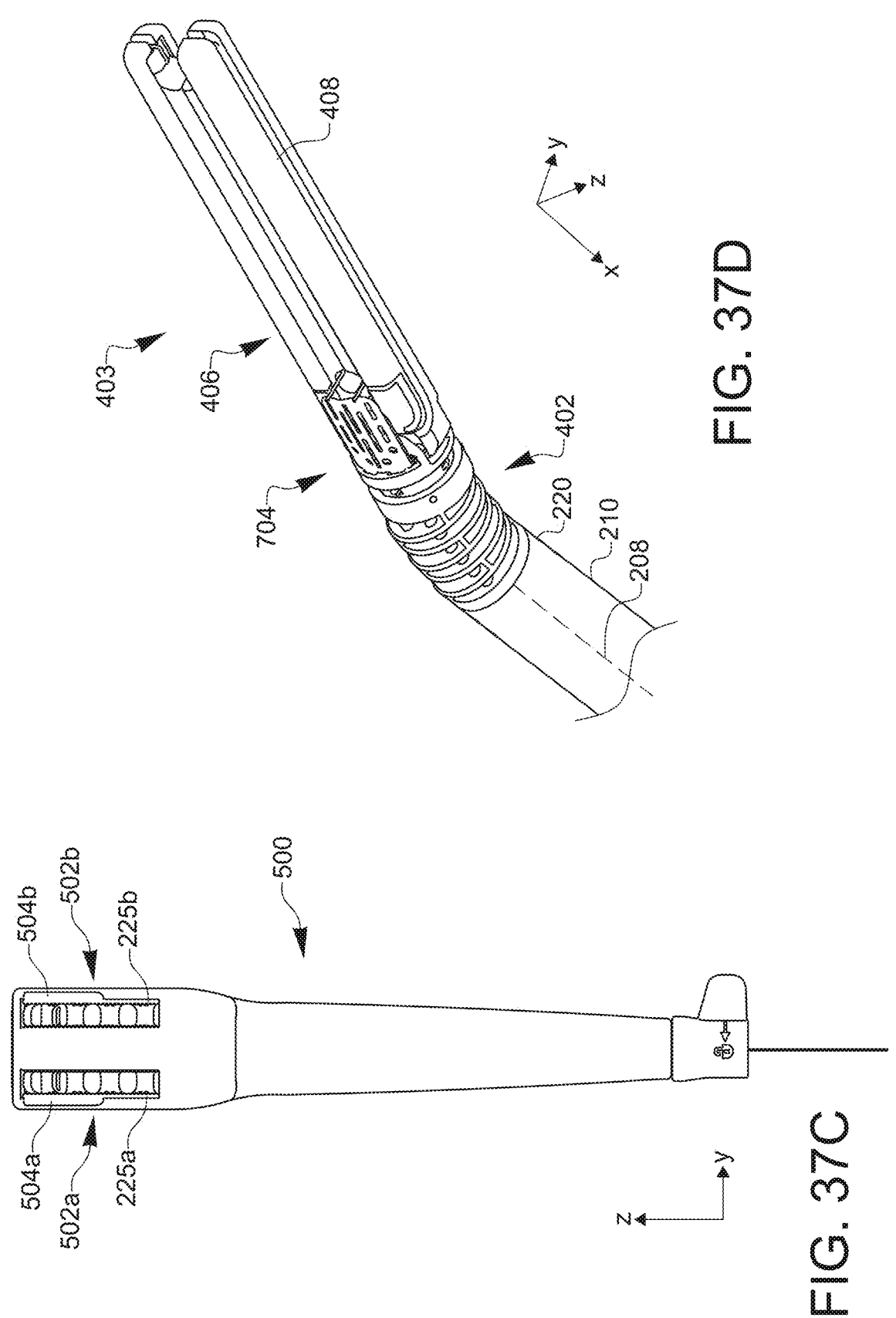
FIG. 37D is a perspective view of a distal end of a shaft, a flexible coupling, and a jaw assembly of the introducer device of FIGS. 37A to 37C.

As illustrated in FIGS. 37A to 37C, a further embodiment of an introducer device 500 is provided that may be similar to the introducer devices 200, 400, and specific features of the introducer device 500 that are similar or identical to those of the introducer devices 200, 400 will share the same reference numbers. Turning to the introducer device 500 in more detail, and as illustrated in FIGS. 45A and 45B, the jaw assembly 403 is illustrated in the open position and the closed position, respectively, with the atrial clip assembly 300 being omitted for clarity. The coupling assembly 228 may include a yoke portion 704, which may be similar or identical to yoke portion 404 illustrated in FIG. 15, and the yoke portion 704 may be coupled to the distal end 434 of the flexible coupling 402.

Figures 45A, 45B:
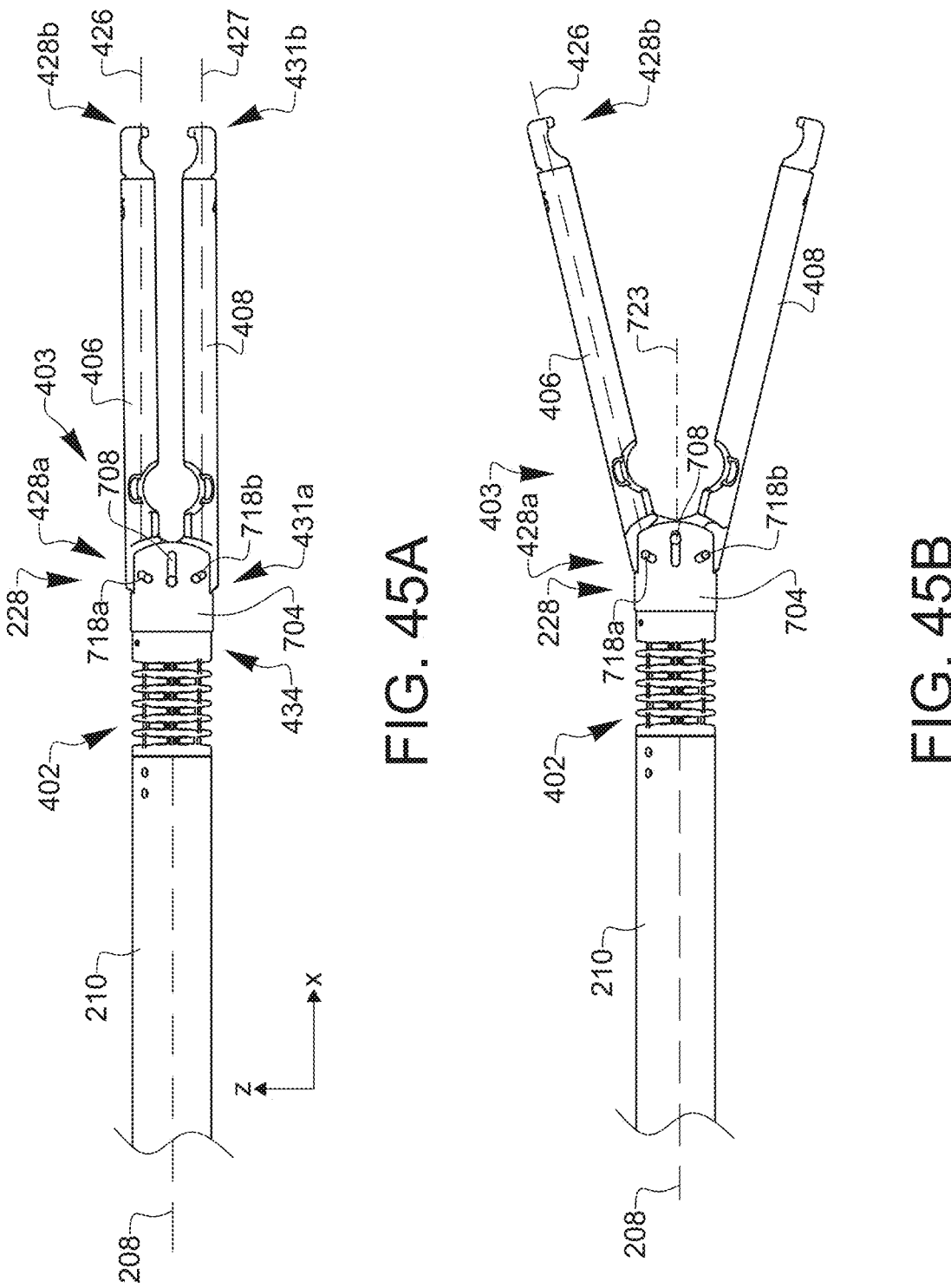
FIG. 45A illustrates a jaw assembly in a closed position.
FIG. 45B illustrates the jaw assembly in an open position.
Figures 45C, 46:
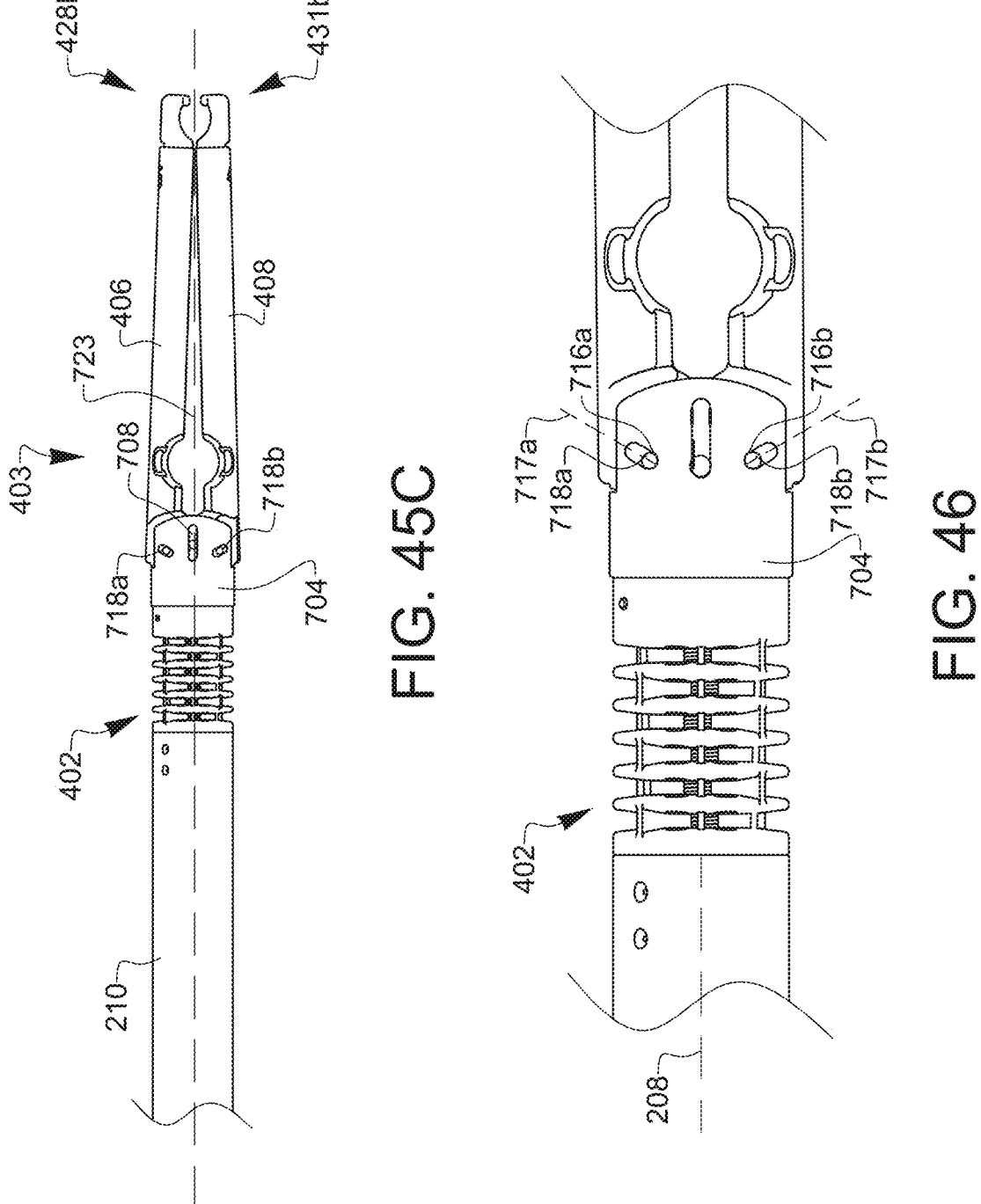
FIG. 45C illustrates the jaw assembly in an intermediate position.
FIG. 46 illustrates the jaw assembly.
Figure 48A:
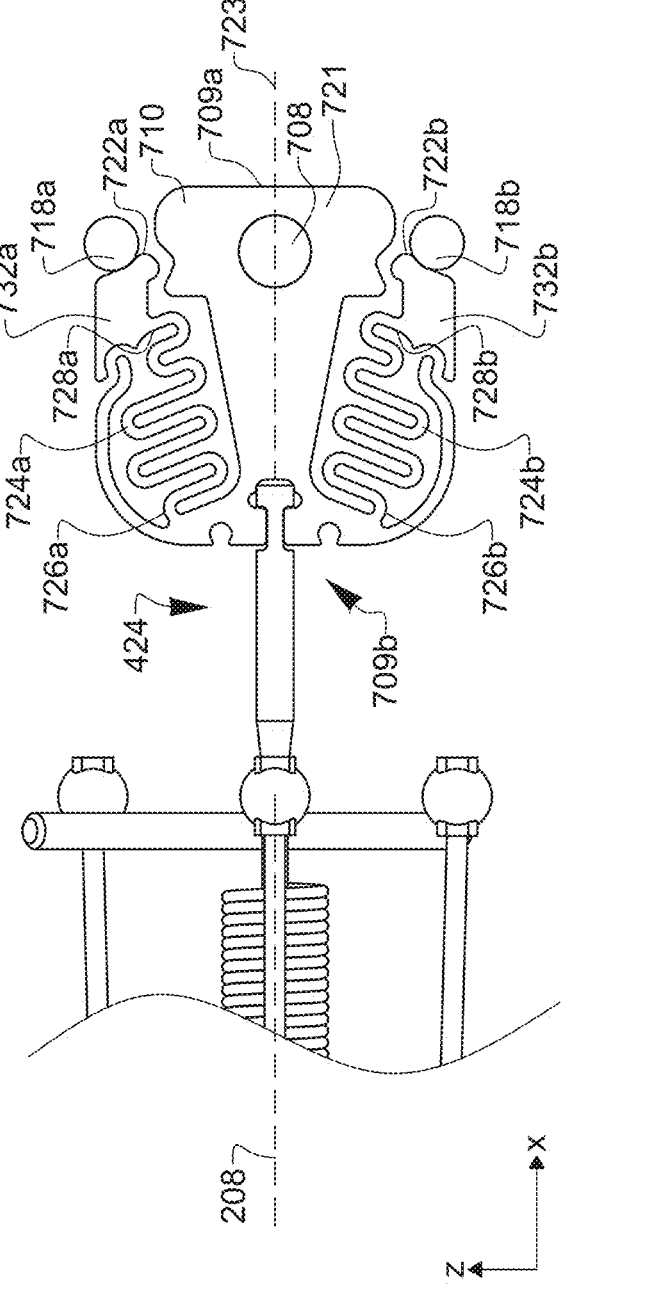
FIGS. 48A to 48G illustrated a jaw spring of the jaw assembly in various positions.
Figure 48C:
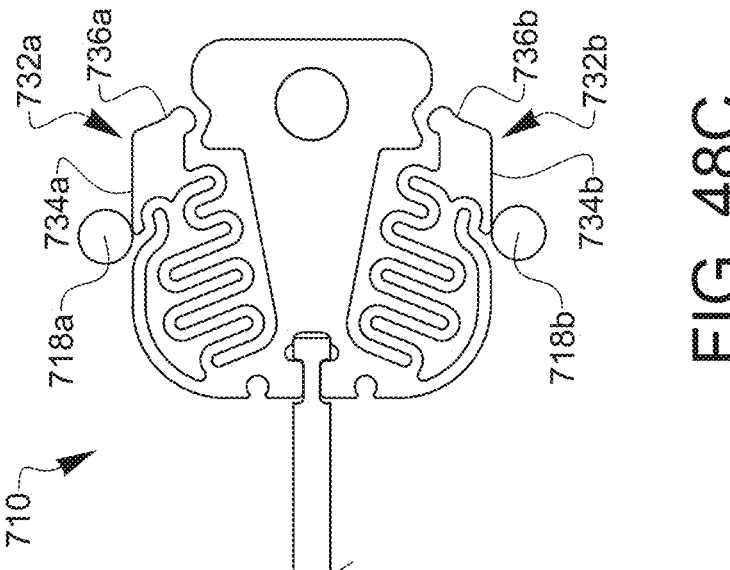
Figure 48B:
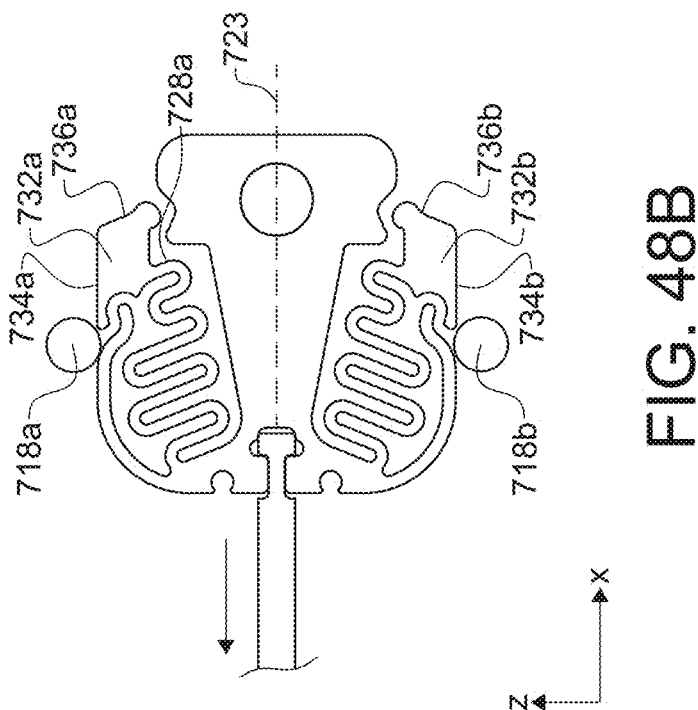

With reference to FIG. 46, the yoke portion 704 may include a drive slot 706 that may extend in a direction along or substantially along the shaft axis 210. In other embodiments, the drive slot 706 may extend in a direction forming an acute angle with the shaft axis 208, may be offset from the shaft axis 208, may have one or more portions that may be offset from the shaft axis 208, and/or may be non-linear or have one or more portions that are non-linear. The drive slot 706 may receive a drive pin 708 that may be configured to displace between a distal position at the distal end of the drive slot 706 and a proximal position at the proximal end of the drive slot 706. The drive pin 708 may be coupled to a portion of a jaw spring 710, which is illustrated in FIGS. 48A and 48B, in which the jaw assembly 403, the atrial clip assembly 300, and the flexible coupling 402 is omitted for clarity. With reference to FIG. 48A, the drive pin 708 may be coupled to a first portion of a base portion 721 of the jaw spring 710, and the base portion 721 may extend from a distal end 709a to a proximal end 709b along a base axis 723. The base axis 723 may be aligned with the shaft axis 208 when the jaw assembly 403 is not rotated or pivoted relative to the distal end 220 of the shaft 210, as illustrated in FIG. 37A. The first portion of the base portion 721 may be at or adjacent to a distal end 709a of the base portion 721 of the jaw spring 710. The distal end of the actuation wire 424 may be coupled to a second portion of the jaw spring 710, such as a portion at or adjacent to the proximal end

709b of the base portion 721. The first portion and the second portion may be aligned along the base axis 723.

Accordingly, as the distal end of the actuation wire 424 is displaced distally (by displacement of the actuation lever 206), the drive pin 708 displaces between the proximal position to the distal position in the drive slot 706, and as the distal end of the actuation wire 424 is moved proximally from the distal position, the drive pin 708 displaces between the distal position to the proximal position within the drive slot 706. FIG. 45A illustrates the drive pin 708 in the proximal position of the drive slot 706, in which the jaw assembly 403 is in the closed position, and FIG. 45B illustrates the drive pin 708 in the distal position of the drive slot 706, in which the jaw assembly 403 is in the open position. FIG. 45C illustrates the drive pin 708 in an intermediate position between the distal position and the proximal position of the drive slot 706, in which the jaw assembly 403 is in an intermediate position in which a distal end 428b of the first jaw 406 is at or adjacent to a distal end 431b of the second jaw 408.

Figures 47A, 47B:
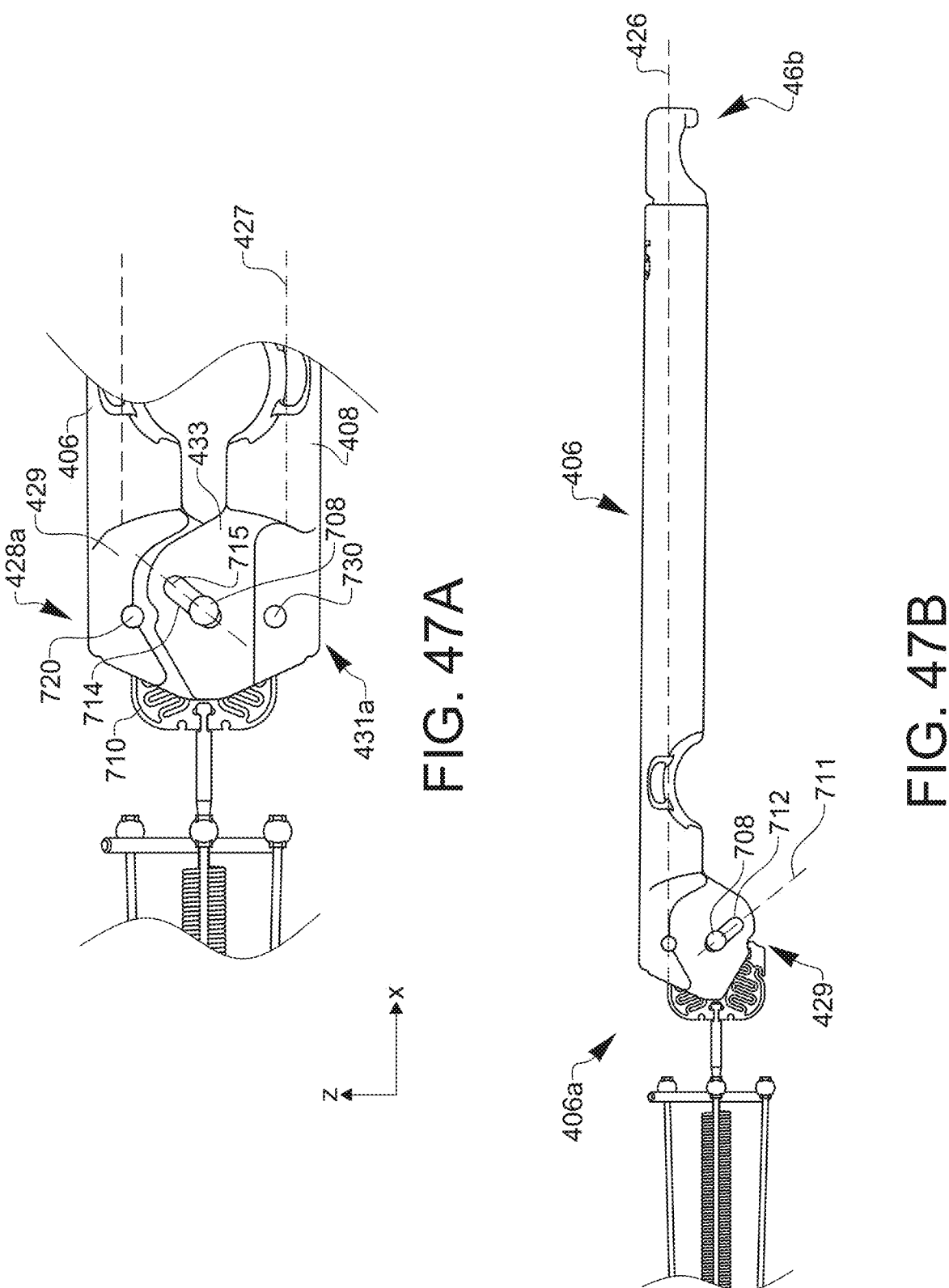
FIG. 47A illustrates the jaw assembly with the yoke portion omitted for clarity.
FIG. 47B illustrates the jaw assembly with the yoke portion and second jaw omitted for clarity.

Turning to FIG. 45A, the first jaw 406 may extend along a first jaw axis 426 from a proximal end 428a to the distal end 428b. As illustrated in FIG. 47A, in which the atrial clip assembly 300, the flexible coupling 402, and the yoke portion 704 are omitted for clarity, the first jaw 406 may include an engagement portion 429 at or adjacent to the proximal end 428a. As illustrated in FIG. 47B, in which the second jaw 408 is additionally omitted for clarity, a first jaw slot 712 may extend through a portion of the engagement portion 429 of the first jaw 406, and the first jaw slot 712 may be configured to receive the drive pin 708. The first jaw slot 712 may extend along an axis 711 that is disposed at an acute angle to the first jaw axis 426, and the first jaw slot 712 may converge towards the first jaw axis 426 as the first jaw slot 712 extends from the distal end 428b to the proximal end 428a. In some embodiments, the angle between the axis 711 and the first jaw axis 426 may be between 80° and 10°, such as a range between 60° and 25°, or a range between 60° and 35°.

Turning again to FIG. 45A, the second jaw 408 may extend along a second jaw axis 427 from a proximal end 431a to the distal end 431b. As illustrated in FIG. 47A, in which the atrial clip assembly 300, the flexible coupling 402, and the yoke portion 704 are omitted for clarity, the second jaw 408 may include an engagement portion 433 at or adjacent to the proximal end 431a. The engagement portion 433 may include a slot (not shown) that may extend along the X-Z pale of the reference coordinate system of FIG. 37A, and the slot may be configured to receive the engagement portion 429 of the first jaw 204 such that the engagement portion 428 may rotate within the X-Z plane within the slot of the engagement portion 433 of the second jaw 408. The engagement portion 433 of the second jaw 408 may include a second jaw slot 714 that may be configured to receive the drive pin 708. The second jaw slot 714 may extend along an axis 715 that is disposed at an acute angle to the second jaw axis 427, and the second jaw slot 714 may converge towards the second jaw axis 427 as the second jaw slot 714 extends from the from the distal end 431b to the proximal end 431a. In some embodiments, the angle between the axis 715 and the second jaw axis 427 may be between 80° and 10°, such as a range between 60° and 25°, or a range between 60° and 35°.

So configured, as the distal end of the actuation wire 424 is moved from a proximal position to a distal position, the drive pin 708 displaces between the proximal position to the distal position in the drive slot 706 of the yoke portion 704.

In this proximal position of the drive pin 708, the jaw assembly 403 is in the closed position of FIG. 45A. As the distal end of the actuation wire 424 is moved distally, the jaw spring 710, and thus the drive pin 708, is also displaced distally. Because the drive pin 708 is disposed within the first jaw slot 712 and the second jaw slot 714, the first jaw 406 and the second jaw 408 pivot about the drive pin 708 towards the open position of the jaw assembly 403 as the drive pin 708 displaces distally. When the distal end of the actuation wire 424 is moved to its most distal position, the drive pin 708, is in the distal position within the drive slot 706 of the yoke portion 704, and the jaw assembly 403 is in the open position of FIG. 45B.

From this position, the distal end of the actuation wire 424 may be displaced (by, e.g., the actuation lever 206) from the distal position towards the proximal position. As the distal end of the actuation wire 424 is moved proximally, the jaw spring 710, and thus the drive pin 708, is also displaced proximally in the drive slot 706 of the yoke portion 704. Because the drive pin 708 is disposed within the first jaw slot 712 and the second jaw slot 714, the first jaw 406 and the second jaw 408 pivot about the drive pin 708 towards the closed position of the jaw assembly 403 as the drive pin 708 displaces proximally. When the distal end of the actuation wire 424 is moved to the intermediate position illustrated in FIG. 45C, the drive pin 708 is in the intermediate position within the drive slot 706 of the yoke portion 704, and the jaw assembly 403 is in the intermediate position, which will be described in more detail in a following section. When the distal end of the actuation wire 424 is then moved to its most proximal position, the drive pin 708, is in the proximal position within the drive slot 706 of the yoke portion 704, and the jaw assembly 403 is in the closed position of FIG. 45A.

Turning again to FIG. 46, the yoke portion 704 may include a first secondary slot 716*a* on a first side (e.g., above) the drive slot 706 and a second secondary slot 716*b* on a second side (e.g., below) the drive slot 706. The first secondary slot 716*a* may extend along a first slot axis 717*a*, and the first slot axis 717*a* may extend in a direction forming an acute angle with the shaft axis 210. In some embodiments, the acute angle may be between 80° and 10°, such as a range between 80° and 45°, or a range between 80° and 60°. In other embodiments, the first slot axis 717*a*, or one or more portions of the first slot axis 717*a*, may extend in any direction or directions relative to the shaft axis 210, and/or may be non-linear or have one or more portions that are non-linear.

The first secondary slot 716*a* may receive a top pin 718*a* that may be configured to displace between a distal position at the distal end of the first secondary slot 716*a*, which corresponds to the open position of the jaw assembly 403 illustrated in FIG. 45B, and a proximal position at the proximal end of the first secondary slot 716*a*, which corresponds to the closed position of the jaw assembly 403 illustrated in FIG. 45A. The top pin 718*a* may be received in an aperture 720 of the first jaw 406, illustrated in FIG. 47A in which the jaw assembly 403 is in the open position and in which the top pin 718*a*, the atrial clip assembly 300, the flexible coupling 402, and the yoke portion 704 are omitted for clarity. The aperture 720 may be disposed in the engagement portion 429 of the first jaw 406 and may be configured and/or sized to prevent the top pin 718*a* from displacing relative to the first jaw 406.

While disposed within the aperture 720, the top pin 718*a* may be in contact with a third portion of the jaw spring 710, as illustrated in FIG. 48A. In particular, the jaw spring 710 may include a first spring arm 724*a* that extends from a first end 726*a* to a second end 728*a*, and a first cam portion 732*a* may be disposed at the second end 728*a* of the first spring arm 724*a*. The first end 726*a* of the first spring arm 724*a* may be coupled to the base portion 721, such as a portion of the base portion 721 that is at or adjacent to the proximal end 709*b* of the base portion 721. In some embodiments, the first end 726*a* of the first spring arm 724*a* may be integrally formed with the portion of the base portion 721. So configured, the first spring arm 724*a* may be cantilevered from the portion of the base portion 721 such that the second end 728*a* (and/or the cam portion 732*a*) may displace in a direction generally normal to the base axis 723 relative to the first end 726*a* (i.e., in a direction along the Z-axis of the reference coordinate system of FIG. 48A). In addition, all or a portion of the first spring arm 724*a* may have a shape that provides a restorative force when the second end 728*a* is displaced towards the first end 726*a* in a direction generally parallel to the base axis 723. For example, the first spring arm 724*a* may have an undulating, wavelike shape between the first end 726*a* and the second end 728*a*. The shape may include two or more segments that are parallel and that are disposed generally normal to an axis that extends form the first end 726*a* and the second end 728*a*.

With reference to FIG. 48B, the first cam portion 732*a* may include a first engagement surface portion 734*a* and a second engagement surface portion 736*a*, and the first engagement surface portion 734*a* and the second engagement surface portion 736*a* may be configured to allow the top pin 718*a* to ride or slide along the first engagement surface portion 734*a* and the second engagement surface portion 736*a* as the top pin 718*a* displaces between the proximal position at the proximal end of the first secondary slot 716*a* and the distal position at the distal end of the first secondary slot 716*a*, and vice versa. In some embodiments, the first engagement surface portion 734*a* may extend in a direction parallel to the base axis 723 and the second engagement surface portion 736*a* may extend in a direction generally normal to the base axis 723. However, the second engagement surface portion 736*a* may include one or more non-linear portions, and the one or more non-linear portion may be contoured, and may be a slightly concave shape.

When the jaw assembly 403 is in the open position, which is illustrated in FIG. 45B, the top pin 718*a* is in the distal position at the distal end of the first secondary slot 716*a*, the drive pin 708 is at the distal end of the drive slot 706, and the jaw spring 710 is in the distal position. In this position, the top pin 718*a* may contact a portion of the first spring arm 724*a* that is at or adjacent to a first end portion of the first engagement surface portion 734*a*, of the top pin 718*a* may contact a portion of the first spring arm 724*a* that is proximal to the first end portion of the first engagement surface portion 734*a*, as illustrated in FIG. 48B.

As the jaw spring 710 begins to move proximally and the distal position drive pin 708 moves proximally in the drive slot 706 from the distal position, the jaw assembly 403 begins to move toward the closed position. In addition, the top pin 718*a* begins to move proximally from the distal end of the first secondary slot 716*a*, and the first arm 406 begins to rotate towards the closed position. During this displacement in the first secondary slot 716*a*, and as the jaw spring 710 begins to move proximally, the top pin 718*a* may contact and glide across a portion of the first spring arm 724*a* that is at the first end portion of the first engagement surface portion 734*a*, as illustrated in FIG. 48C.

As the jaw spring 710 continues to move proximally and displaces the drive pin 708 proximally in the drive slot 706, the jaw assembly 403 continues to move toward the closed position. The top pin 718a, displacing proximally in the first secondary slot 716a, remains in contact with a portion of the first spring arm 724a that is at the first end portion of the first engagement surface portion 734a, and this contact begins to displace the first cam portion 732a towards the base portion 721. Continued contact between the top pin 718a and the first engagement surface portion 734a biases a portion of the first cam portion 732a into contact with a corresponding portion of the base portion 721, as illustrated in FIG. 48D. Due to the pivoting about one or both of the drive pin 708 and the top pin 718a, and because the drive pin 708 is disposed within the first jaw slot 712 of the first jaw 406, the distal end 428b of the first jaw 406 begins to converge towards the base axis 723 while the proximal end 428a does not converge towards the base axis 723.

Figure 48E:
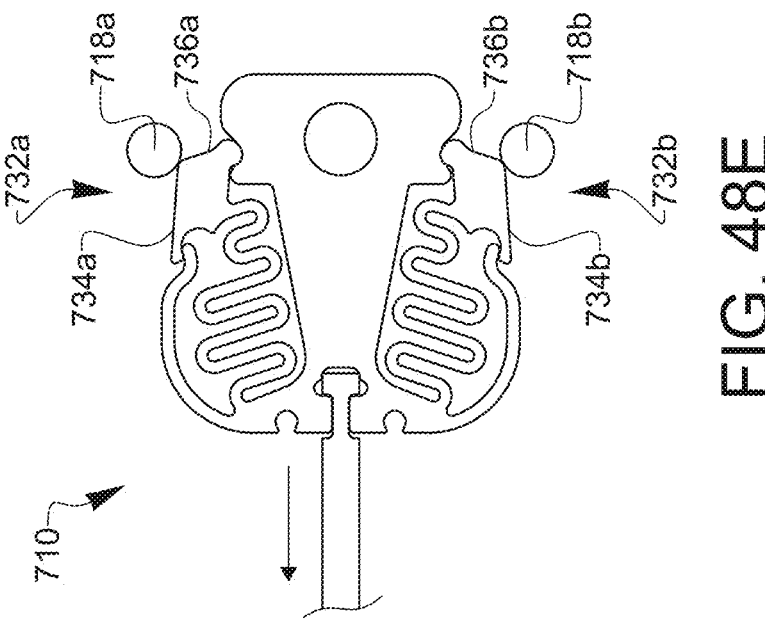
Figure 48D:
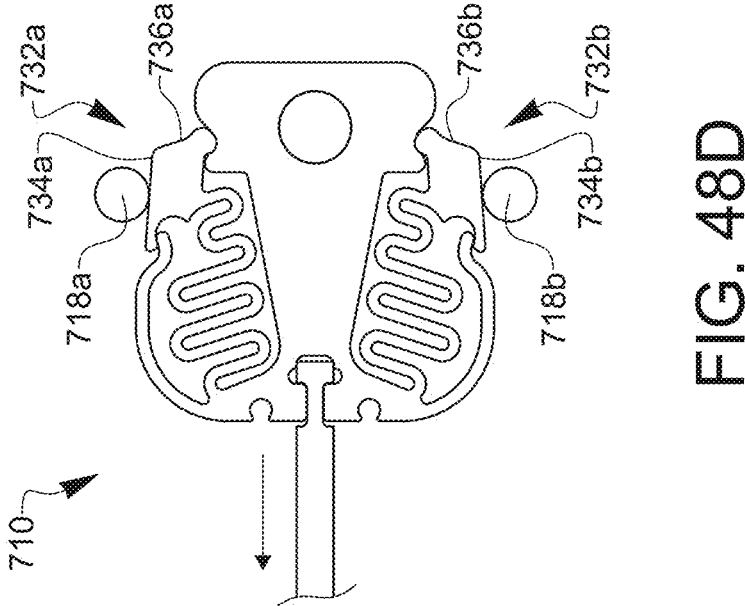

As the jaw spring 710 continues to move proximally, contact between the top pin 718a, displacing proximally in the first secondary slot 716a, and the first engagement surface portion 734a continues to maintain the portion of the first cam portion 732a into contact with a corresponding portion of the base portion 721 until the top pin 718a is disposed at the second end portion of the first engagement surface portion 734a, as illustrated in FIG. 48E. In this position, the distal end 428b of the first jaw 406 is disposed adjacent to the base axis 723 while the proximal end 428a is offset from the base axis, as illustrated in FIG. 45C. In this position, the drive pin 708 in an intermediate position between the distal position and the proximal position of the drive slot 706, and the top pin 718a is in an intermediate position in the first secondary slot 716a. This position allows the distal ends of the atrial clip assembly 10, 300 to engage the left atrial appendage during application before the proximal ends of the atrial clip assembly 10, 300, which results in a more secure engagement with the left atrial appendage when the atrial clip assembly 10, 300 is applied to the left atrial appendage.

Figure 48G:
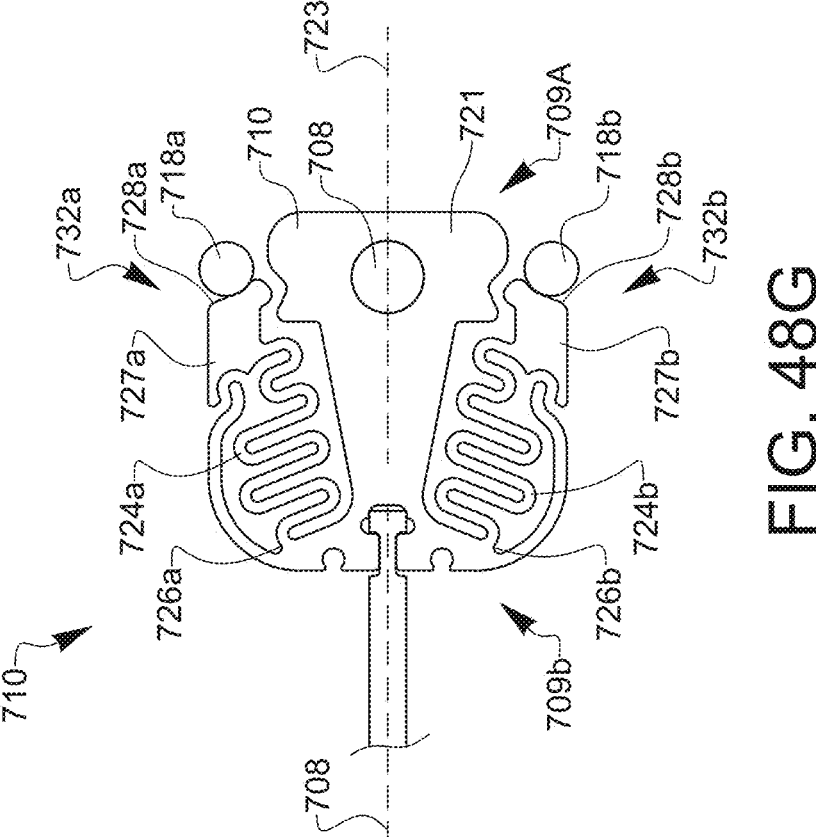
Figure 48F:
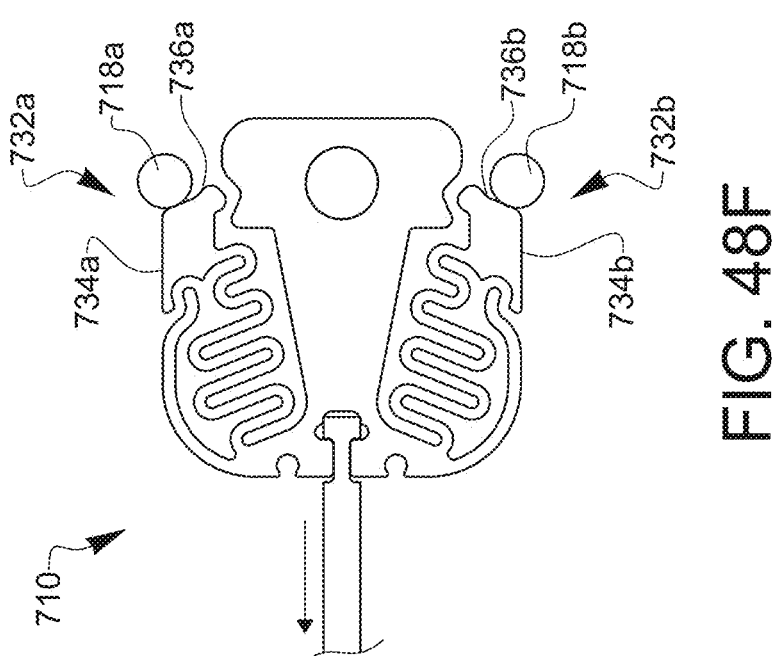

As the jaw spring 710 continues to move proximally, the top pin 718a displaces over an edge between the second end portion of the first engagement surface portion 734a and a first end portion of the second engagement surface portion 736a, and the top pin 718a displaces along the second engagement surface portion 736a from the first end towards a second end, as illustrated in FIG. 48F. When the top pin 718a displaces over the edge, the first cam portion 732a displaces away from the base portion 721. In the position, the distal end 428b of the first jaw 406 does not displace (or does not significantly displace) relative to the base axis 723, but the proximal end 428a begins to converge towards the base axis 723.

As the jaw spring 710 continues to move into the most proximal position, in which the drive pin 708 moves to the most proximal position in the drive slot 706, the top pin 718a continues to displaces along the second engagement surface portion 736a to a point at or adjacent to the second end of the second engagement surface portion 736a, as illustrated in FIG. 48G, which is identical to FIG. 48A. In some embodiments, the top pin 718a continues to displace along the second engagement surface portion 736a to a point between the first end and the second end of the second engagement surface portion 736a. The distal end 428b of the first jaw 406 still does not displace (or does not significantly displace) relative to the base axis 723, but the proximal end 428a continues to converge towards the base axis 723 until the first jaw 406 reaches the closed position of the jaw assembly 403 illustrated in FIG. 45A.

As illustrated in FIG. 46, the yoke portion 704 may include the second secondary slot 716b that may extend along a second slot axis 717b, and the second slot axis 717b may extend in a direction forming an acute angle with the shaft axis 210. In some embodiments, the acute angle formed by the second slot axis 717b and the shaft axis 210 may be equal to the acute angle formed by the first slot axis 717a and the shaft axis 210. In some embodiments, the acute angle may be between 80° and 10°, such as a range between 80° and 45°, or a range between 80° and 60°. In other embodiments, the second slot axis 717b, or one or more portions of the second slot axis 717b, may extend in any direction or directions relative to the shaft axis 210, and/or may be non-linear or have one or more portions that are non-linear.

The second secondary slot 716b may receive a bottom pin 718b that may be configured to displace between a distal position at the distal end of the second secondary slot 716b, which corresponds to the open position of the jaw assembly 403 illustrated in FIG. 45B, and a proximal position at the proximal end of the second secondary slot 716b, which corresponds to the closed position of the jaw assembly 403 illustrated in FIG. 45A. The bottom pin 718b may be received in an aperture 730 of the second jaw 408, illustrated in FIG. 47A in which the jaw assembly 403 is in the open position and in which the bottom pin 718b, the atrial clip assembly 300, the flexible coupling 402, and the yoke portion 704 are omitted for clarity. The aperture 730 may be disposed in the engagement portion 433 of the second jaw 408 and may be configured and/or sized to prevent the bottom pin 718b from displacing relative to the second jaw 408.

While disposed within the aperture 730, the bottom pin 718b may be in contact with a fourth portion of the jaw spring 710, as illustrated in FIG. 48A. In particular, the jaw spring 710 may include a second spring arm 724b that extends from a first end 726b to a second end 728b, and a second cam portion 732b may be disposed at the second end 728b of the second spring arm 724b. The second spring arm 724b may be substantially identical to the first spring arm 724a or may be a mirror image of the first spring arm 724a with the base axis 723 being the axis of symmetry. In particular, the first end 726b of the second spring arm 724b may be coupled to the base portion 721, such as a portion of the base portion 721 that is at or adjacent to the proximal end 709b of the base portion 721. In some embodiments, the first end 726b of the second spring arm 724b may be integrally formed with the portion of the base portion 721. So configured, the second spring arm 724b may be cantilevered from the portion of the base portion 721 such that the second end 728b may displace in a direction generally normal to the base axis 723 relative to the first end 726b (i.e., in a direction along the Z-axis of the reference coordinate system of FIG. 48A). In addition, the second spring arm 724b may have a shape that provides a restorative force when the second end 728b is displaced towards the first end 726b in a direction generally parallel to the base axis 723. For example, the second spring arm 724b may have an undulating, wavelike shape between the first end 726b and the second end 728b. The shape may include two or more segments that are parallel and that are disposed generally normal to an axis that extends form the first end 726b and the second end 728b.

With reference to FIG. 48B, the second cam portion 732b may include a first engagement surface portion 734b and a second engagement surface portion 736b, and the first engagement surface portion 734b and the second engagement surface portion 736*b* may be configured to allow the bottom pin 718*b* to ride or slide along the first engagement surface portion 734*a* and the second engagement surface portion 736*a* as the bottom pin 718*b* displaces between the proximal position at the proximal end of the second secondary slot 716*b* and the distal position at the distal end of the second secondary slot 716*b*, and vice versa. In some embodiments, the second engagement surface portion 734*b* may extend in a direction parallel to the base axis 723 and the second engagement surface portion 736*b* may extend in a direction generally normal to the base axis 723. However, the second engagement surface portion 736*b* may include one or more non-linear portions, and the one or more non-linear portion may be contoured, and may be a slightly concave shape.

When the jaw assembly 403 is in the open position, which is illustrated in FIG. 45B, the bottom pin 718*b* is in the distal position at the distal end of the second secondary slot 716*b*, the drive pin 708 is at the distal end of the drive slot 706, and the jaw spring 710 is in the distal position. In this position, the bottom pin 718*b* may contact a portion of the second spring arm 724*b* that is at or adjacent to a first end portion of the first engagement surface portion 734*b*, of the bottom pin 718*b* may contact a portion of the second spring arm 724*b* that is proximal to the first end portion of the first engagement surface portion 734*b*, as illustrated in FIG. 48B.

As the jaw spring 710 begins to move proximally and the distal position drive pin 708 moves proximally in the drive slot 706 from the distal position, the jaw assembly 403 begins to move toward the closed position. In addition, the bottom pin 718*b* begins to move proximally from the distal end of the second secondary slot 716*b*, and the second arm 408 begins to rotate towards the closed position. During this displacement in the second secondary slot 716*b*, and as the jaw spring 710 begins to move proximally, the bottom pin 718*b* may contact and glide across a portion of the second spring arm 724*b* that is at the first end portion of the first engagement surface portion 734*b*, as illustrated in FIG. 48C.

As the jaw spring 710 continues to move proximally and displaces the drive pin 708 proximally in the drive slot 706, the jaw assembly 403 continues to move toward the closed position. The bottom pin 718*b*, displacing proximally in the second secondary slot 716*b*, remains in contact with a portion of the second spring arm 724*b* that is at the first end portion of the first engagement surface portion 734*b*, and this contact begins to displace the second cam portion 732*b* towards the base portion 721. Continued contact between the bottom pin 718*b* and the first engagement surface portion 734*b* biases a portion of the second cam portion 732*b* into contact with a corresponding portion of the base portion 721, as illustrated in FIG. 48D. Due to the pivoting about one or both of the drive pin 708 and the bottom pin 718*b*, and because the drive pin 708 is disposed within the second jaw slot 714 of the second jaw 408, the distal end 431*b* of the second jaw 408 begins to converge towards the base axis 723 while the proximal end 431*a* does not converge towards the base axis 723.

As the jaw spring 710 continues to move proximally, contact between the bottom pin 718*b*, displacing proximally in the second secondary slot 716*b*, and the first engagement surface portion 734*b* continues to maintain the portion of the second cam portion 732*b* into contact with the corresponding portion of the base portion 721 until the bottom pin 718*b* is disposed at the second end portion of the first engagement surface portion 734*b*, as illustrated in FIG. 48E. In this position, the distal end 431*b* of the second jaw 408 is disposed adjacent to the base axis 723 while the proximal end 431*a* is offset from the base axis 723, as illustrated in FIG. 45C. In this position, the drive pin 708 in an intermediate position between the distal position and the proximal position of the drive slot 706, and the bottom pin 718*b* is in an intermediate position in the second secondary slot 716*b*. This position allows the distal ends of the atrial clip assembly 10, 300 to engage the left atrial appendage during application before the proximal ends of the atrial clip assembly 10, 300, which results in a more secure engagement with the left atrial appendage.

As the jaw spring 710 continues to move proximally, the bottom pin 718*b* displaces over an edge between the second end portion of the first engagement surface portion 734*b* and a first end portion of the second engagement surface portion 736*b*, and the bottom pin 718*b* displaces along the second engagement surface portion 736*b* from the first end towards a second end, as illustrated in FIG. 48F. When the bottom pin 718*b* displaces over the edge, the second cam portion 732*b* displaces away from the base portion 721. In the position, the distal end 431*b* of the second jaw 408 does not displace (or does not significantly displace) relative to the base axis 723, but the proximal end 431*a* begins to converge towards the base axis 723.

As the jaw spring 710 continues to move into the most proximal position, in which the drive pin 708 moves to the most proximal position in the drive slot 706, the bottom pin 718*b* continues to displaces along the second engagement surface portion 736*b* to a point at or adjacent to the second end of the second engagement surface portion 736*b*, as illustrated in FIG. 48G, which is identical to FIG. 48A. In some embodiments, the bottom pin 718*b* continues to displace along the second engagement surface portion 736*b* to a point between the first end and the second end of the second engagement surface portion 736*b*. The distal end 431*b* of the second jaw 408 still does not displace (or does not significantly displace) relative to the base axis 723, but the proximal end 431*a* continues to converge towards the base axis 723 until the second jaw 408 reaches the closed position of the jaw assembly 403 illustrated in FIG. 45A.

To displace the jaw assembly from the closed position of FIG. 45A to the open position of FIG. 45B, which is typically performed prior to the application of the atrial clip assembly 10, 300 on a left atrial appendage, the process previously described is reversed as the jaw spring 710 is moved from the most proximal position of FIG. 45A to the most distal position of FIG. 45B.

Figures 43A, 43B, 43C:
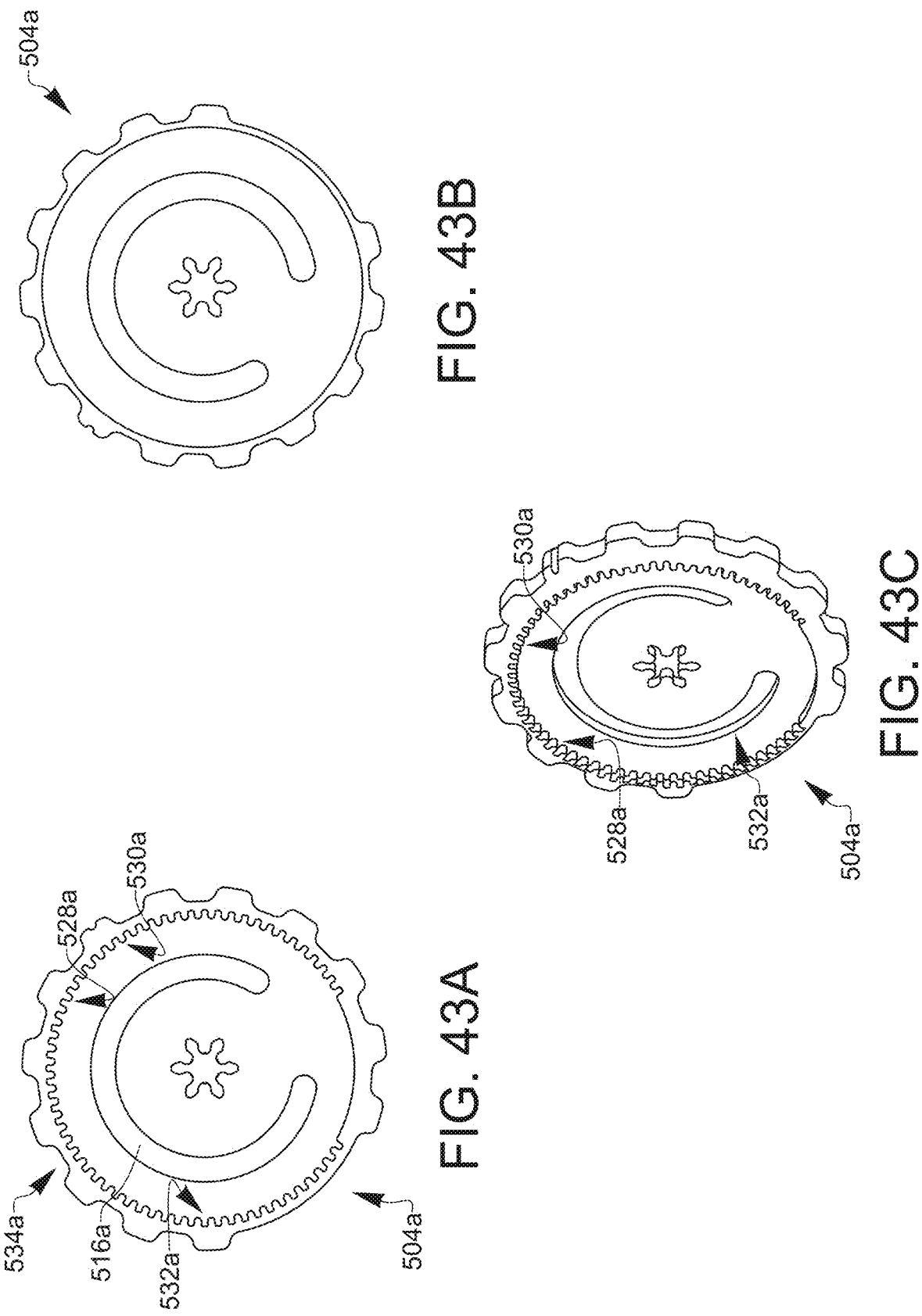

As illustrated in FIGS. 37A to 37C, the introducer device 500 may control the orientation of the jaw assembly 403 in a manner different than the introducer devices 200, 400. In particular, instead of the of the first control lever assembly 416 and the second control lever assembly 418 illustrated in an embodiment of the introducer device 400, the introducer device 500 may include a first adjustment assembly 502*a* and a second adjustment assembly 502*b*. As illustrated in FIGS. 38A to 39D, which provides various views of all or a portion of the first adjustment assembly 502*a* and/or the second adjustment assembly 502*b* (with portions of the introducer device 500 removed for clarity), the first adjustment assembly 502*a* may include a first adjustment wheel 504*a* (illustrated in FIGS. 43A to 43C) that may be rotatably coupled to a first end portion of a first axle 506, and the first axle 506 may be aligned with a center point of the first adjustment wheel 504*a*. The second adjustment assembly 502*b* may include a second adjustment wheel 504*b* that may be rotatably coupled to a second end portion of the first axle 506, and the first axle 506 may be aligned with a center point of the second adjustment wheel 504*b*. The second adjustment wheel 504*b* may be identical to (or substantially identical to, or a mirror image of) the first adjustment wheel 504*a*.

Figure 39A:
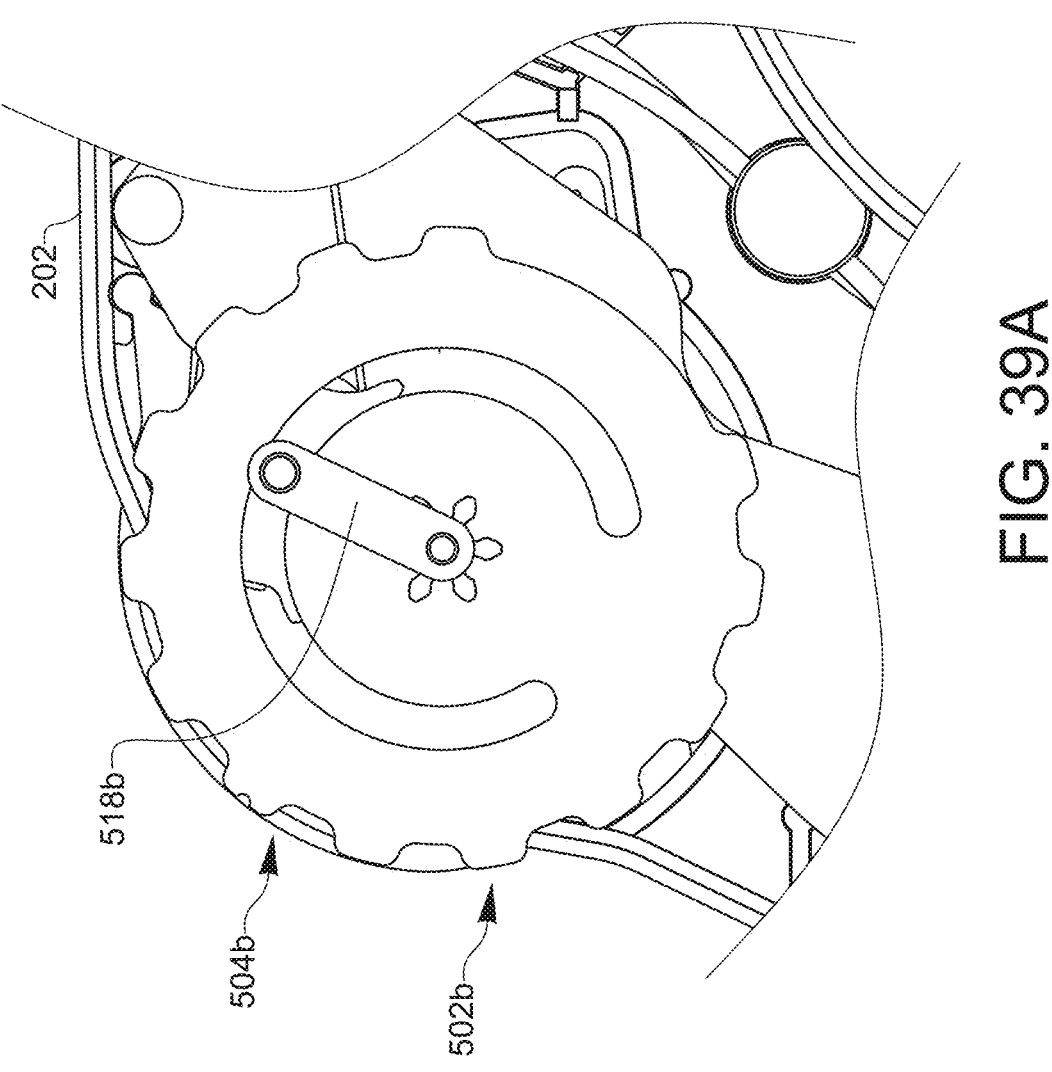

As illustrated in FIG. 39D, a first spur gear 508*a* may be disposed adjacent to the first end portion of the first axle 506, and the first spur gear 508*a* may rotate with the first adjustment wheel 504*a* relative to the first axle 506. A second spur gear 508*b* may be disposed adjacent to the second end portion of the first axle 506, and the second spur gear 508*b* may rotate with the first adjustment wheel 504*a* relative to the first axle 506. The first spur gear 508*a* may intermesh with a portion of a first adjustment gear 510*a*, which may rotate about a first portion of a second axle 512. The second axle 512 may have ends that are secured to portions of the housing portion 202 such that the second axle 512 rotates relative to the housing portion 202 but does not displace relative to the housing portion 202. The second axle 512 may be connected to the first axle 506 by a first bar 518*a* that extends from a point adjacent to the first end of the second axle 512 to a point adjacent to the first end of the first axle 512. The second axle 512 may be further connected to the first axle 506 by a second bar 518*b* that extends from a point adjacent to the second end of the second axle 512 to a point adjacent to the second end of the first axle 512. In this manner, the first axle 506 is not coupled to the housing portion 202. However, the second axle 512 and the first axle 506 may be coupled to each other and/or to the housing portion 202 in any suitable manner.

So configured, a rotation of the first adjustment wheel 504*a* about the first axle 506 results in a corresponding rotation of the first adjustment gear 510*a* about the second axle 512. In particular, a rotation of the first adjustment wheel 504*a* in a first direction results in a corresponding rotation of the first adjustment gear 510*a* in a first direction, and a rotation of the first adjustment wheel 504*a* in a second direction results in a corresponding rotation of the first adjustment gear 510*a* in a second direction.

The proximal end of a corresponding first one or more of the control wires 414*a*, 414*b*, 414*c*, 414*d* may be coupled to a corresponding portion of the first adjustment gear 510*a* (or to a drum member 514 illustrated in FIGS. 39B and 39C that may be fixed to the first adjustment gear 510*a*) such that when the first adjustment wheel 504*a* is rotated in the first direction, the corresponding first one or more of the control wires 414*a*, 414*b*, 414*c*, 414*d* are displaced, thereby displacing the distal ends of the first one or more of the control wires 414*a*, 414*b*, 414*c*, 414*d*, thereby displacing the jaw assembly 403, by virtue of the flexible coupling 402, in a first direction relative to the distal end 220 of the shaft 210, as illustrated in FIG. 37D. For example, the first direction may be a first direction along the Z-axis of the reference coordinate system of FIG. 37D. Correspondingly, when the first adjustment wheel 504*a* is rotated in the second direction, the corresponding first one or more of the control wires 414*a*, 414*b*, 414*c*, 414*d* are displaced, thereby displacing the distal ends of the first one or more of the control wires 414*a*, 414*b*, 414*c*, 414*d*, thereby displacing the jaw assembly 403, by virtue of the flexible coupling 402, in a second direction relative to the distal end 220 of the shaft 210. For example, the second direction may be a direction opposite to the first direction along the Z-axis of the reference coordinate system of FIG. 37D. The first direction and the second direction relative to the distal end 220 of the shaft 210 may be separated by any angular distance, such as by 180 degrees. Thus, by using a thumb to contact a portion of the first adjustment wheel 504*a* that extends through a first slot 225*a* formed in a portion of the housing portion 202 (see FIG.

37C), a user grasping the introducer device 500 may rotate the first adjustment wheel 504*a* to pivot, rotate, or displace the jaw assembly 403 relative to the distal end 220 of the shaft 210 in a first bending plane, such as the X-Z plane of the reference coordinate system illustrated in FIG. 37D, thereby allowing the user to precisely position the jaw assembly 403 during a minimally-invasive procedure.

Figure 39C:
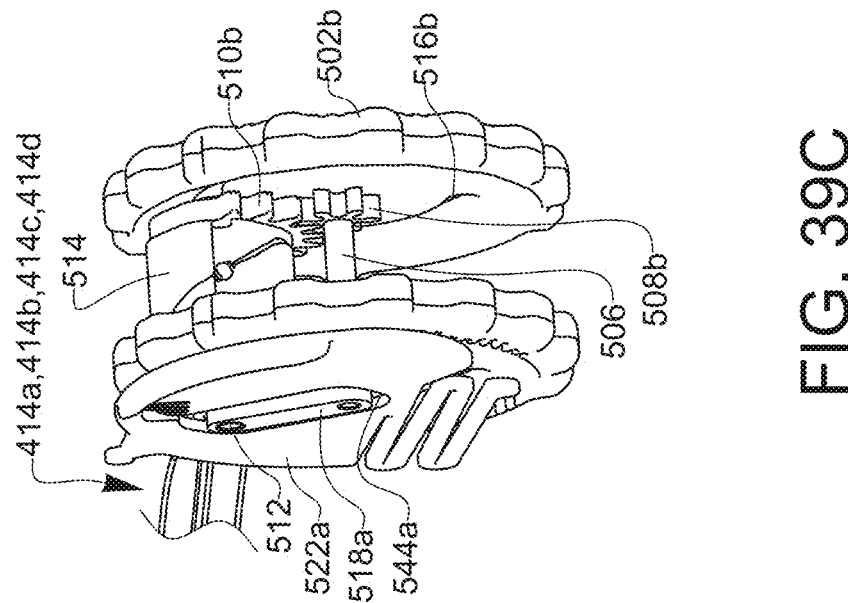
Figure 39B:
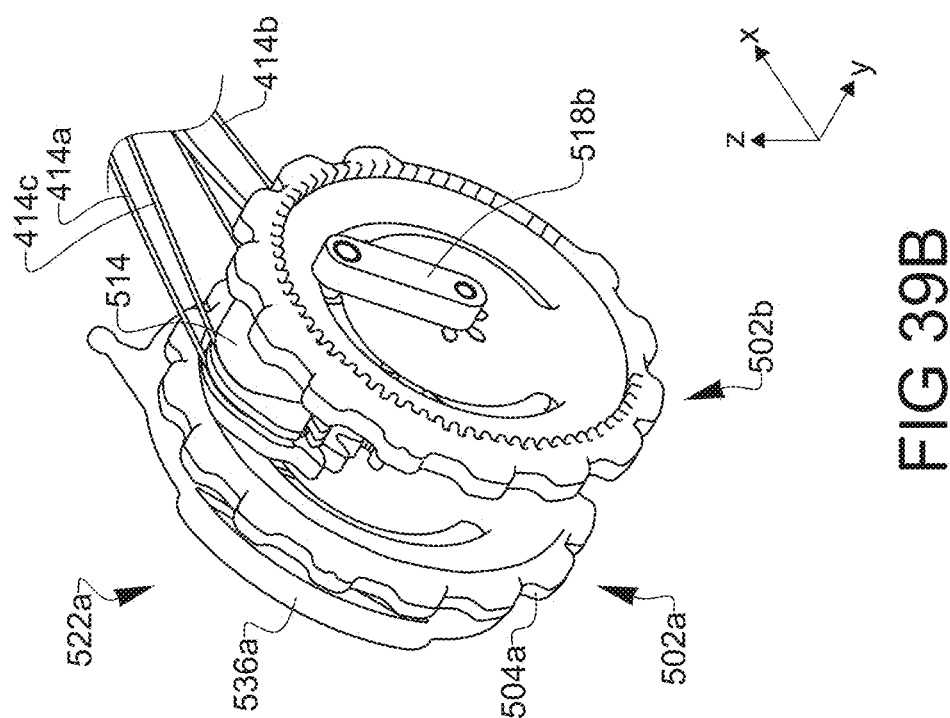

As illustrated in FIG. 39C. the second spur gear 508*b* may intermesh with a portion of a second adjustment gear 510*b*, which may pivot about a second portion of the second axle 512. The second axle 512 may be further connected to the first axle 506 by a second bar 518*b* that extends from a point adjacent to the second end of the second axle 512 to a point adjacent to the second end of the first axle 512. So configured, a rotation of the second adjustment wheel 504*b* results in a corresponding rotation of the second adjustment gear 510*b*. In particular, a rotation of the second adjustment wheel 504*b* in a first direction results in a corresponding rotation of the second adjustment gear 510*b* in a first direction, and a rotation of the second adjustment wheel 504*b* in a second direction results in a corresponding rotation of the second adjustment gear 510*b* in a second direction.

The proximal end of a corresponding second one or more of the control wires 414*a*, 414*b*, 414*c*, 414*d* may be coupled to a corresponding portion of the second adjustment gear 510*b* (or to the drum member 514 illustrated in FIGS. 39B and 39C that may be fixed to the second adjustment gear 510*a* is the drum member 214 is not fixed to the first adjustment gear 510*a*) such that when the second adjustment wheel 504*b* is rotated in the first direction, the corresponding second one or more of the control wires 414*a*, 414*b*, 414*c*, 414*d* are displaced, thereby displacing the distal ends of the second one or more of the control wires 414*a*, 414*b*, 414*c*, 414*d*, thereby displacing the jaw assembly 403, by virtue of the flexible coupling 402, in a third direction relative to the distal end 220 of the shaft 210. For example, the third direction may be a first direction along the Y-axis of the reference coordinate system of FIG. 37D. Correspondingly, when the second adjustment wheel 504*b* is rotated in the second direction, the corresponding second one or more of the control wires 414*a*, 414*b*, 414*c*, 414*d* are displaced, thereby displacing the distal ends of the second one or more of the control wires 414*a*, 414*b*, 414*c*, 414*d*, thereby displacing the jaw assembly 403, by virtue of the flexible coupling 402, in a fourth direction relative to the distal end 220 of the shaft 210. For example, the fourth direction may be a direction opposite to the third direction along the Z-axis of the reference coordinate system of FIG. 37D. The first direction, the second direction, the third direction, and the fourth direction relative to the distal end 220 of the shaft 210 may be separated by any angular distance, such as by 90 degrees. Thus, by using a thumb to contact a portion of the second adjustment wheel 504*b* that extends through a second slot 225*b* formed in a portion of the housing portion 202 (see FIG. 37C), a user grasping the introducer device 500 may rotate the second adjustment wheel 504*b* to pivot, rotate, or displace the jaw assembly 403 relative to the distal end 220 of the shaft 210 in a second bending plane, such as the X-Y plane of the reference coordinate system illustrated in FIG. 37D, that may be normal to the a first bending plane. The ability to rotate in the first bending plane and the second bending place will allow the jaw assembly 403 to pivot about the flexible coupling 402 in any direction along or aligned with the Y-axis and/or the Z-axis of the reference coordinate system, thereby allowing the user to precisely position the jaw assembly 403 during a minimally-invasive procedure to precisely position the jaw assembly 403 prior to securing the atrial clip assembly 10, 300 to the LAA, without moving the shaft 210 relative to the patient.

A portion of the second axle 512 may extend through a partially circular guide path 516a formed in the first adjustment wheel 504a such that the first adjustment wheel 504a is prevented from rotating beyond a first point in which the first portion of the second axle 512 contacts a first end portion of the guide path 516a and beyond a second point in which the first portion of the second axle 512 contacts a second end portion of the guide path 516a. A further portion of the second axle 512 may extend through a partially circular guide path 516b formed in the second adjustment wheel 504b such that the second adjustment wheel 504b is prevented from rotating beyond a first point in which the second portion of the second axle 512 contacts a first end portion of the guide path 516b and beyond a second point in which the second portion of the second axle 512 contacts a second end portion of the guide path 516b. Thus, by limiting the rotational range of motion of each of the first adjustment wheel 504a and the second adjustment wheel 504b, the displacement of the jaw assembly 403 relative to the distal end 220 of the shaft 210 is also limited to an acceptable range.

To prevent an unwanted rotation of the first adjustment wheel 504a or the second adjustment wheel 504b, and/or to allow the first adjustment wheel 504a and/or the second adjustment wheel 504b to be locked in desired positions, the first adjustment assembly 502a may include a first locking assembly 520a and the second adjustment assembly 502b may include a second locking assembly 520b. The first locking assembly 520a may include a first locking member 522a that may be displaceable relative to the first adjustment wheel 504a. As illustrated in FIGS. 39C and 42A to 42D, the first locking member 522a may include a first body portion 523a that extends from a first end to a second end, and the first body portion 523a may be planar and may have the shape of a plate. A first spring portion 524a may be coupled to, or integrally formed with, a portion of (e.g., the second end of) the first body portion 523a. In the embodiment of FIG. 42A, a first end of the first spring portion 524a may be coupled to (or integrally formed with) the second end of the first body portion 523a, and a second end of the first spring portion 524a may be supported by a ledge portion 527a (see FIGS. 41A and 41B) formed on a portion of the housing portion 202. Thus, when the first body portion 523a is displaced towards the ledge portion 527a (see FIG. 40B), the first spring portion 524a biases the first body portion 523a away from the ledge portion 527a.

Figures 41A, 41B:
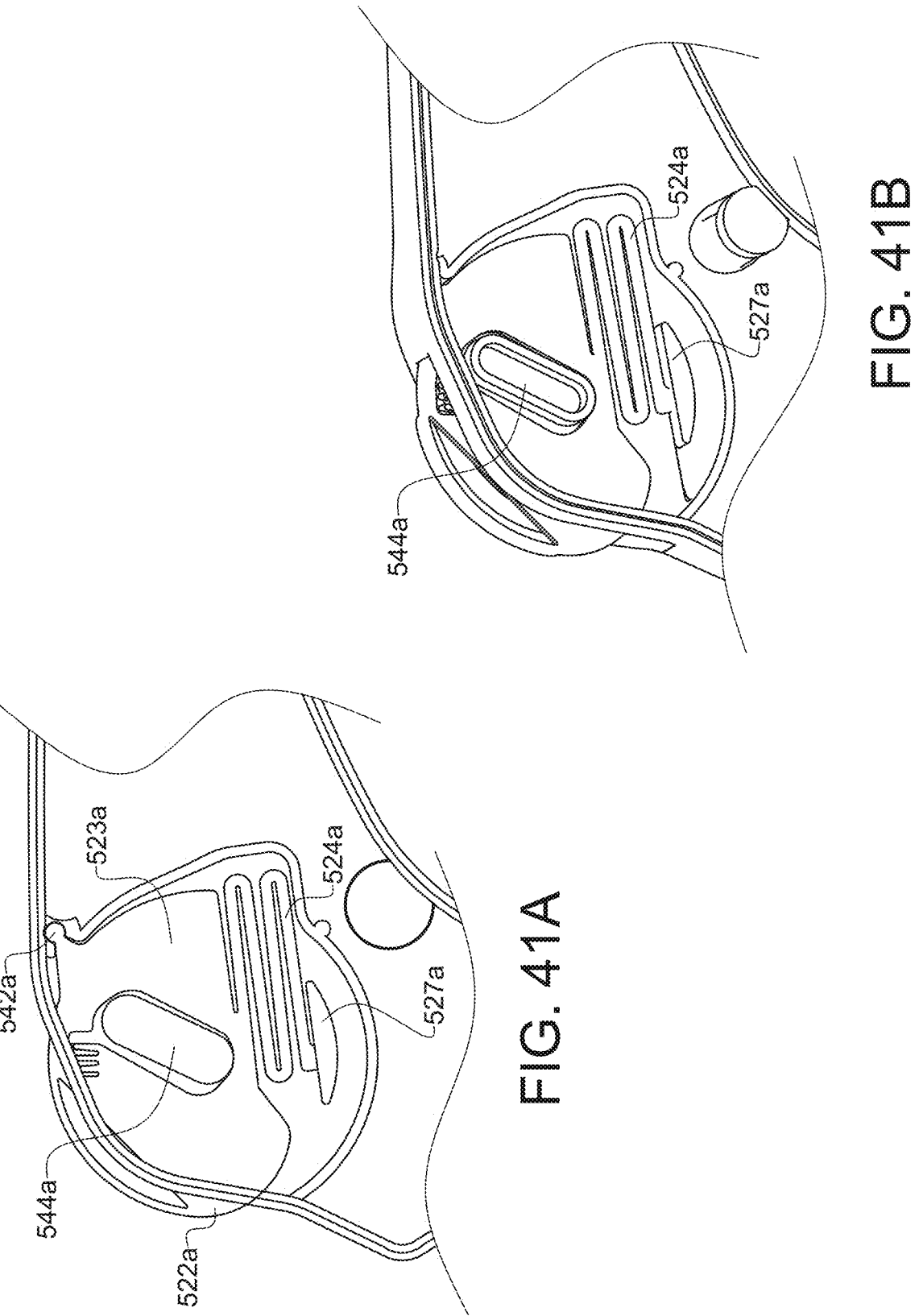
Figure 42B:
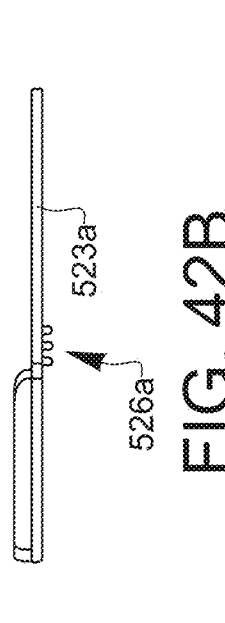
Figure 42D:
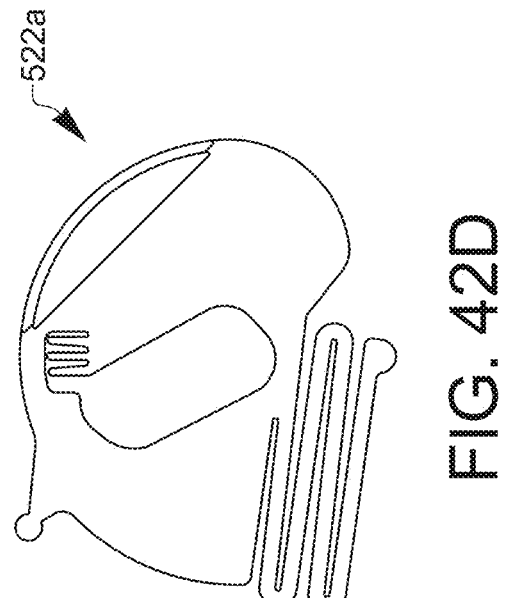
Figure 42A:
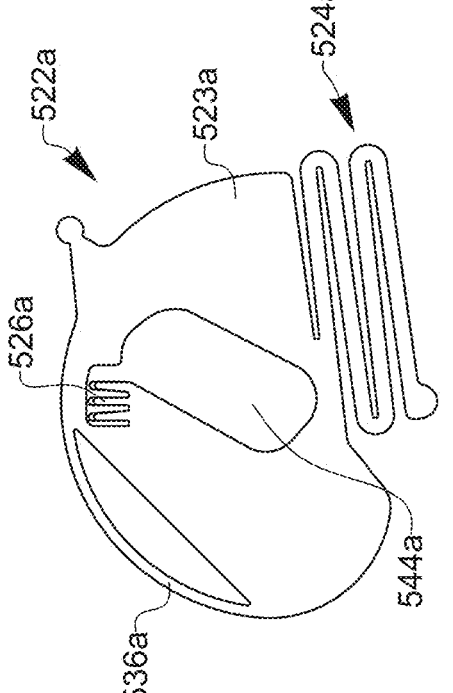
Figure 42C:
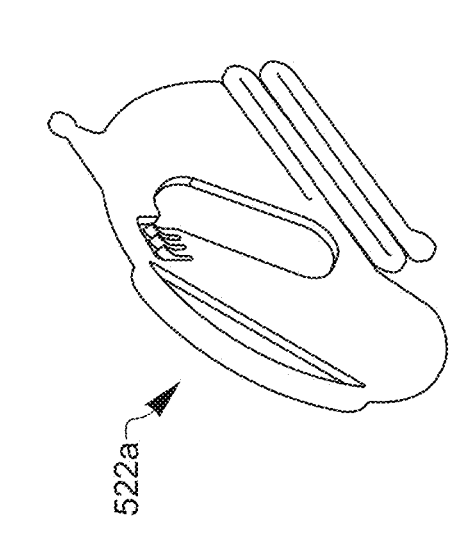

As illustrated in FIG. 41A, the first body portion 523a may also include a first hinge portion 542a that may be secured to a portion at or adjacent to the first end of the first body portion 523a, and the first hinge portion 542a may be secured within or to a portion of the housing portion 202, such as a recess formed within the housing portion 202, such that the first locking member 522a may pivot about the first hinge portion 542a when the first body portion 523a is downwardly displaced (along the arrow 538 of FIG. 40B) by a user. The first body portion 523a may also include a first cutout 544a formed within the first body portion 523a that is configured to receive all or a portion of the first bar 518a. The first cutout 544a may be sized and dimensioned to allow the first locking member 522a to displace as described in more detail below without being obstructed by the first bar 518a.

The first locking member 522a also includes a first engagement portion 526a that may be coupled to, or inte-grally formed with, a portion of (e.g., the first end of) the first body portion 523a. The first engagement portion 526a may be configured to engage a corresponding wheel engagement portion 528a formed on the first adjustment wheel 504a. For example, the wheel engagement portion 528a may be a plurality of teeth 530a formed on or along a circumferential ridge 532a that is inwardly offset from the circumferential edge 534a of the first adjustment wheel 504a. In this embodiment, the first engagement portion 526a of the first locking member 522a may be two or more tines 536a that may each be configured to be disposed between adjacent teeth 530a of the corresponding wheel engagement portion 528a. Thus, when the first locking member 522a is in a first position (i.e., a locked position), the first spring portion 524a (acting against the circumferential ridge 532a) biases the first body portion 523a upwards, and in so doing, biases the first engagement portion 526a into engagement with a portion of the wheel engagement portion 528a formed on the first adjustment wheel 504a, as illustrated in FIG. 40A. That is, in the locked position of the first locking assembly 520a, the two or more tines 536a of the first locking member 522a are biased to be disposed between adjacent teeth 530a of the corresponding wheel engagement portion 528a, thereby preventing the first adjustment wheel 504a from being rotated relative to the first locking member 522a (and to the housing portion 202 and to the first adjustment gear 510a).

The first locking member 522a also includes a first contact portion 536a that extends from a portion of (e.g., the first end of) the first body portion 523a and is coupled to or integrally formed with the first body portion 523a. In the locked position of the first locking assembly 520a, all or a portion of the first contact portion 536a may extend through the first slot 225a formed in the portion of the housing portion 202, and all or a portion of the first contact portion 536a may be aligned with or extend beyond the circumferential edge 534a of the first adjustment wheel 504a.

When it is desired to rotate the first adjustment wheel 504a to displace the jaw assembly 403, the user presses the first contact portion 536a using the same thumb that will contact the first adjustment wheel 504a and press downwards to rotate the first adjustment wheel 504a. This downward force on the first contact portion 536a displaces the first locking member 522a downwardly (i.e., along or substantially along the arrow 538 in FIG. 40B, which may be parallel or substantially parallel to the Z-axis of the reference coordinate system in FIG. 37C) against the upward (i.e., along or substantially along the arrow 540 in FIG. 40A, which may be parallel or substantially parallel to the Z-axis of the reference coordinate system in FIG. 37C) bias provided by the first spring portion 524a. This downward displacement may be the result of a pivoting of the first locking member 522a about the first hinge portion 542a (see FIG. 41A) caused by the downward force on the first contact portion 536a. This downward displacement of the first locking member 522a displaces the first locking member 522a into a second position, or an unlocked position, in which the first engagement portion 526a is not in engagement with a portion of the wheel engagement portion 528a formed on the first adjustment wheel 504a, as illustrated in FIG. 40B. That is, in the unlocked position of the first locking assembly 520a, the two or more tines 536a of the first locking member 522a are offset from the teeth 530a of the corresponding wheel engagement portion 528a, thereby allowing the first adjustment wheel 504a to rotated relative to the first locking member 522a (and to the housing portion 202 and to the first adjustment gear 510a). When the user displaces the jaw assembly 403 to a desired location, the pressure on the first contact portion 536a is released, and the first spring portion 524a biases the first locking member 522a from the unlocked position back to the locked position.

The second locking assembly 520b may be identical to, substantially identical to, or a mirror image of the first locking assembly 520a, and the second locking assembly 520b may operate in an identical manner to the first locking assembly 520a. That is, the second locking assembly 520b may include a second locking member 522b that may be displaceable relative to the second adjustment wheel 504b. As illustrated in FIGS. 39C and 42A to 42D (showing the first locking member 522a), the second locking member 522b may include a second body portion 523b that extends from a first end to a second end, and the second body portion 523b may be planar and may have the shape of a plate. A second spring portion 524b may be coupled to, or integrally formed with, a portion of (e.g., the second end of) the second body portion 523b. In the embodiment of FIG. 42A, a first end of the second spring portion 524b may be coupled to (or integrally formed with) the second end of the second body portion 523b, and a second end of the second spring portion 524b may be supported by a ledge portion 527b (not shown, but identical to the ledge portion 527a in FIG. 41A) formed on a portion of the housing portion 202. Thus, when the second body portion 523b is displaced towards the ledge portion 527b (see FIG. 40B), the second spring portion 524b biases the second body portion 523b away from the ledge portion 527b.

Figures 38A, 38B:
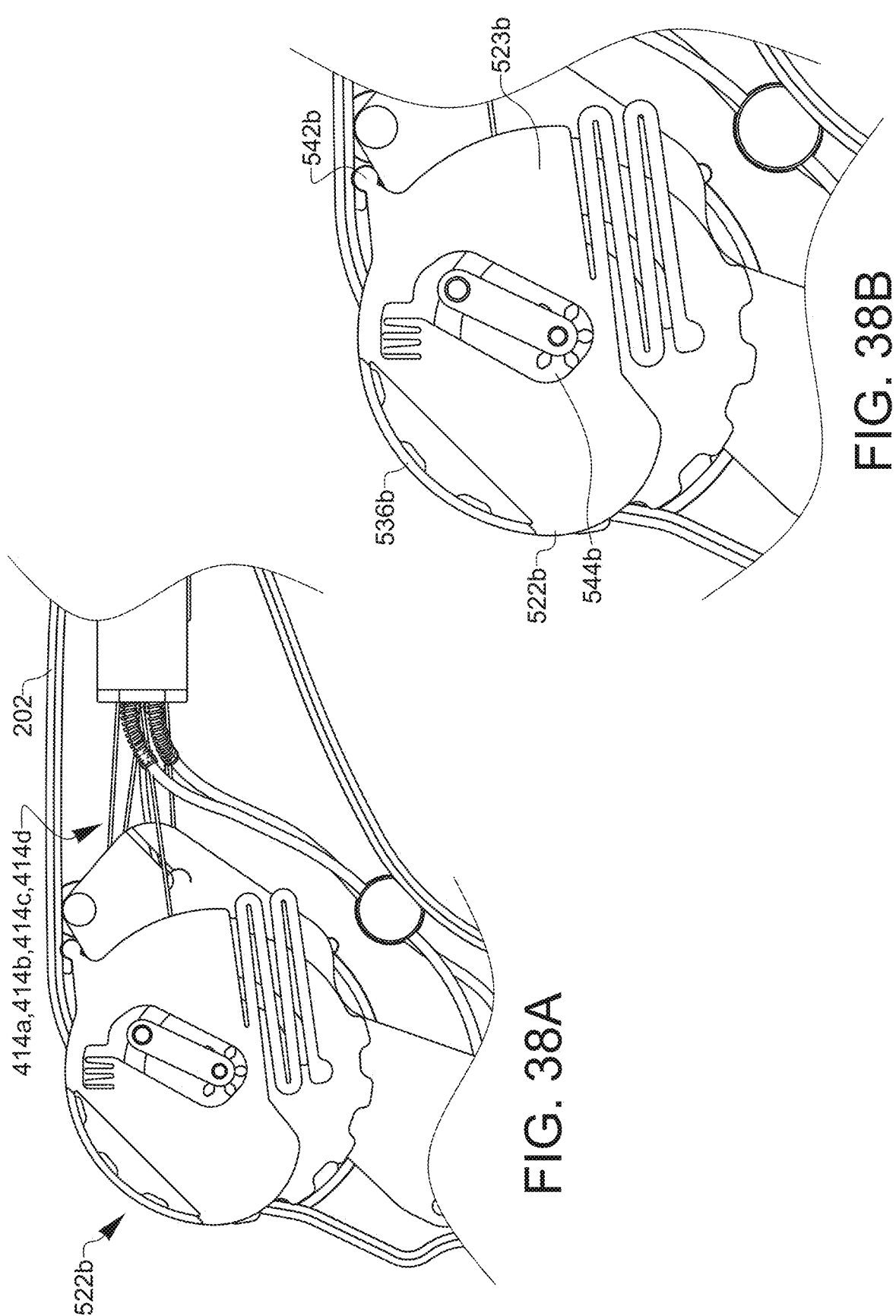

As illustrated in FIG. 38B, the second body portion 523b may also include a second hinge portion 542b that may be secured to a portion at or adjacent to the second end of the second body portion 523b, and the second hinge portion 542b may be secured within or to a portion of the housing portion 202 in the same manner as the first hinge portion 542a of the first body portion 523b. The second body portion 523b may also include a second cutout 544b formed within the second body portion 523b that is configured to receive all or a portion of the second bar 518b, and the second cutout 544b may be identical in function to the first cutout 544a.

The second locking member 522b also includes a second engagement portion 526b that may be coupled to, or integrally formed with, a portion of (e.g., the first end of) the second body portion 523b. The second engagement portion 526b may be configured to engage a corresponding wheel engagement portion 528b formed on the second adjustment wheel 504b. For example, the wheel engagement portion 528b may be a plurality of teeth 530b formed on or along a circumferential ridge 532b that is inwardly offset from the circumferential edge 534b of the second adjustment wheel 504b. In this embodiment, the second engagement portion 526b of the second locking member 522b may be two or more tines 536b that may each be configured to be disposed between adjacent teeth 530b of the corresponding wheel engagement portion 528b. Thus, when the second locking member 522b is in a first position (i.e., a locked position), the second spring portion 524b (acting against the circumferential ridge 532b) biases the second body portion 523b upwards, and in so doing, biases the second engagement portion 526b into engagement with a portion of the wheel engagement portion 528b formed on the second adjustment wheel 504b, as illustrated in FIG. 40A. That is, in the locked position of the second locking assembly 520b, the two or more tines 536b of the second locking member 522b are biased to be disposed between adjacent teeth 530b of the corresponding wheel engagement portion 528b, thereby preventing the second adjustment wheel 504b from being rotated relative to the second locking member 522b (and to the housing portion 202 and to the second adjustment gear 510b).

The second locking member 522b also includes a second contact portion 536b that extends from a portion of (e.g., the first end of) the second body portion 523b and is coupled to or integrally formed with the second body portion 523b. In the locked position of the second locking assembly 520b, all or a portion of the second contact portion 536b may extend through the second slot 225b formed in the portion of the housing portion 202, and all or a portion of the second contact portion 536b may be aligned with or extend beyond the circumferential edge 534b of the second adjustment wheel 504b.

When it is desired to rotate the second adjustment wheel 504b to displace the jaw assembly 403, the user presses the second contact portion 536b using the same thumb that will contact the second adjustment wheel 504b and press downwards to rotate the second adjustment wheel 504b. This downward force on the second contact portion 536b displaces the second locking member 522b downwardly (i.e., along or substantially along the arrow 538 in FIG. 40B, which may be parallel or substantially parallel to the Z-axis of the reference coordinate system in FIG. 37C) against the upward (i.e., along or substantially along the arrow 540 in FIG. 40A, which may be parallel or substantially parallel to the Z-axis of the reference coordinate system in FIG. 37C) bias provided by the second spring portion 524b. This downward displacement may be the result of a pivoting of the second locking member 522b about the second hinge portion 542b (see FIG. 38B) caused by the downward force on the second contact portion 536b. This downward displacement of the second locking member 522b displaces the second locking member 522b into a second position, or an unlocked position, in which the second engagement portion 526b is not in engagement with a portion of the wheel engagement portion 528b formed on the second adjustment wheel 504b, as illustrated in FIG. 40B. That is, in the unlocked position of the second locking assembly 520b, the two or more tines 536b of the second locking member 522b are offset from the teeth 530b of the corresponding wheel engagement portion 528b, thereby allowing the second adjustment wheel 504b to rotated relative to the second locking member 522b (and to the housing portion 202 and to the second adjustment gear 510b). When the user displaces the jaw assembly 403 to a desired location, the pressure on the second contact portion 536b is released, and the second spring portion 524b biases the second locking member 522b from the unlocked position back to the locked position.

Figures 44A, 44B, 44C:
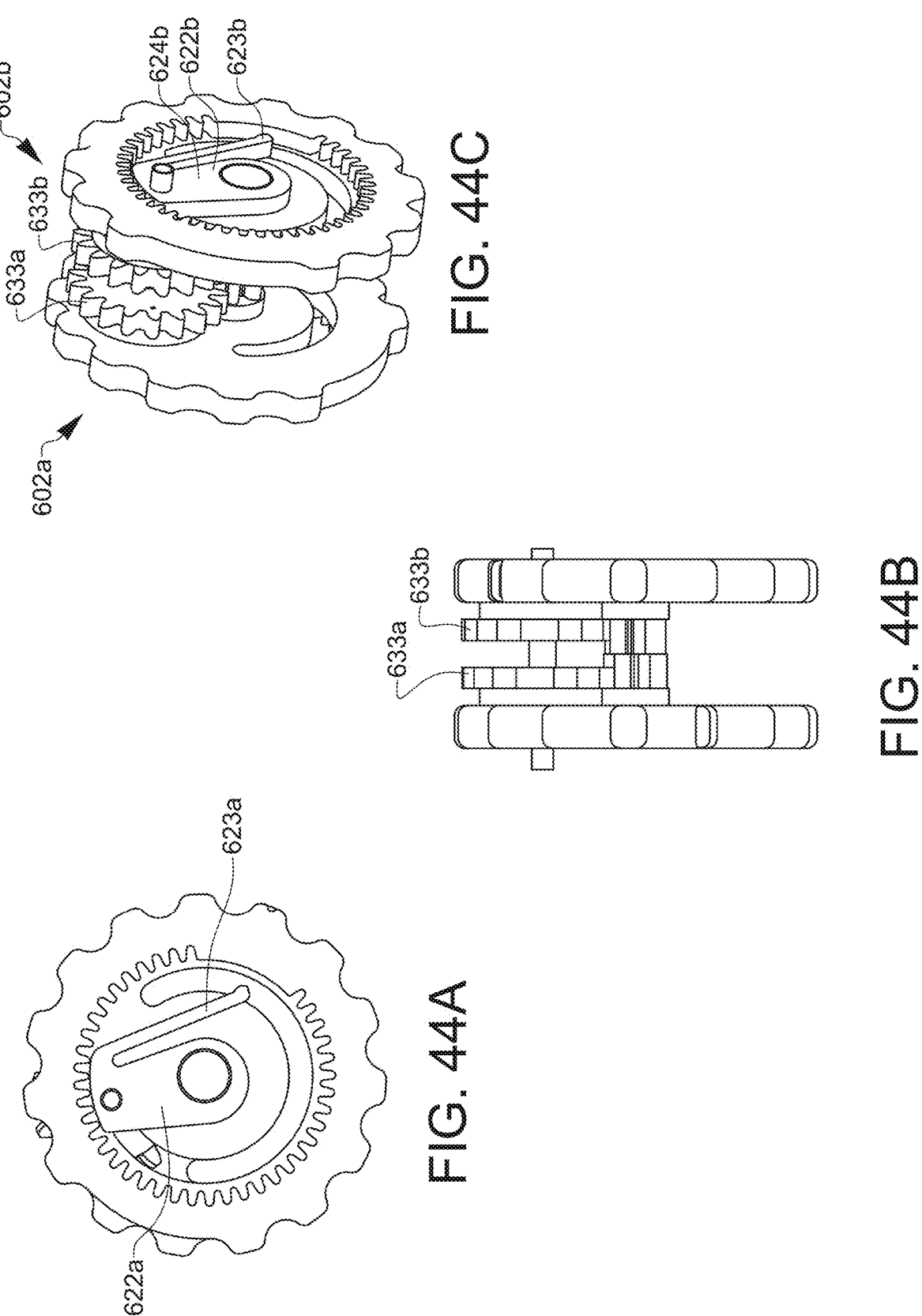
FIGS. 44A to 44H are various views of a further embodiment of a first adjustment assembly and a second adjustment assembly.
Figures 44D, 44E:
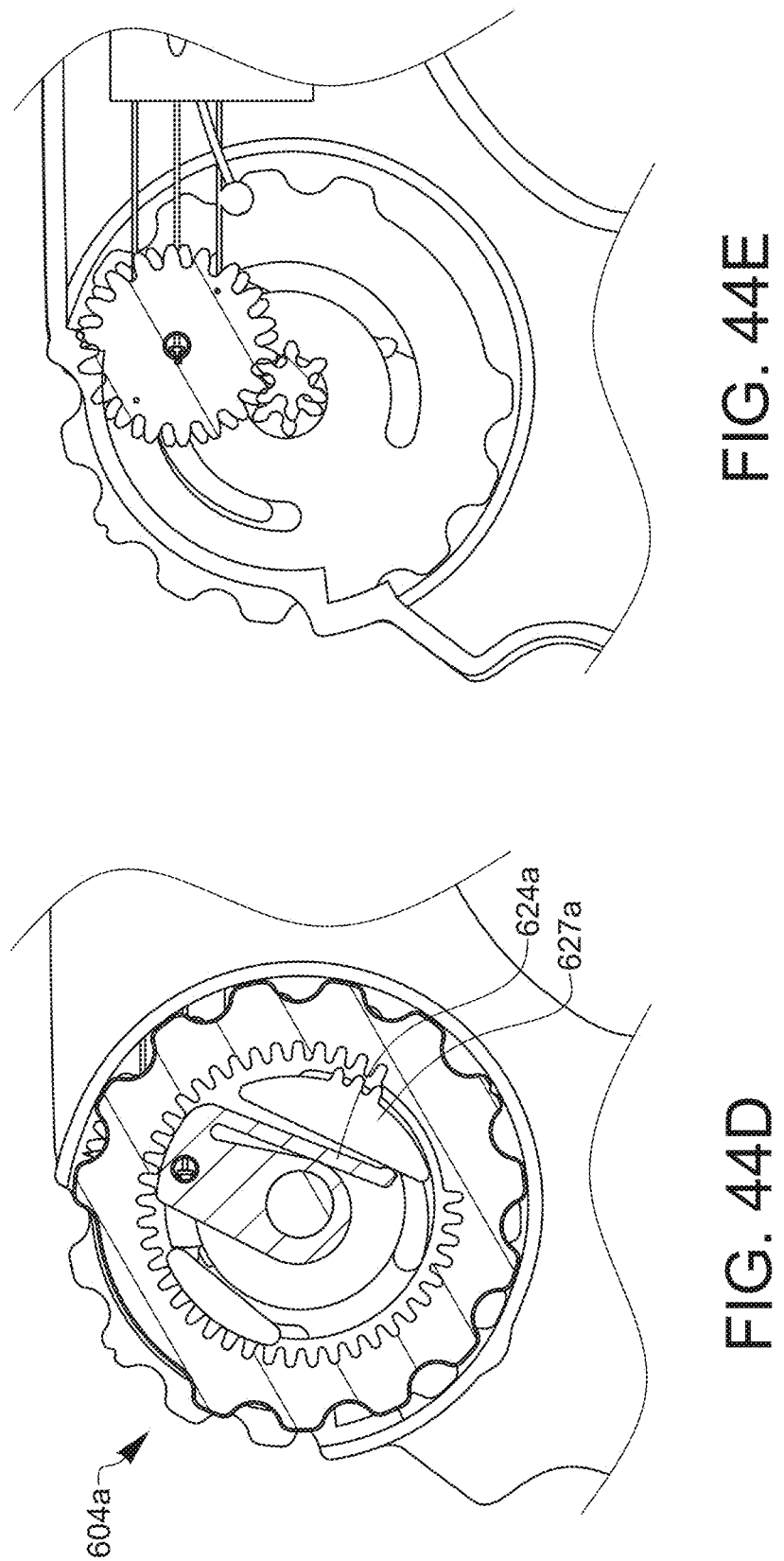
Figure 44G:
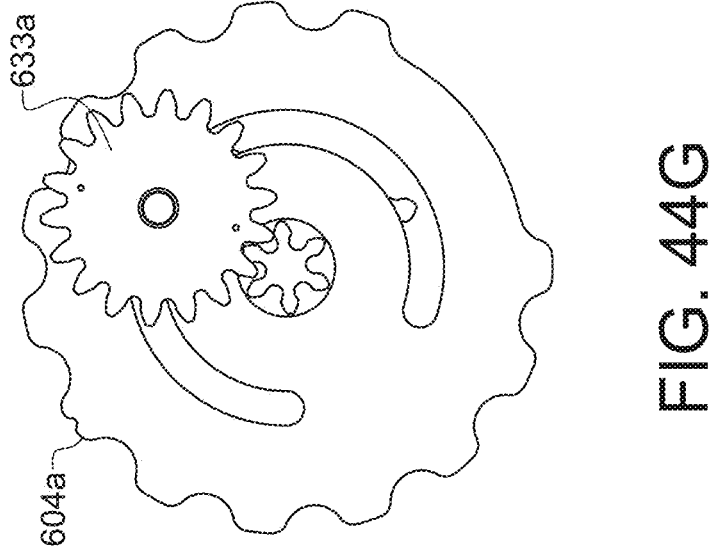
Figure 44F:
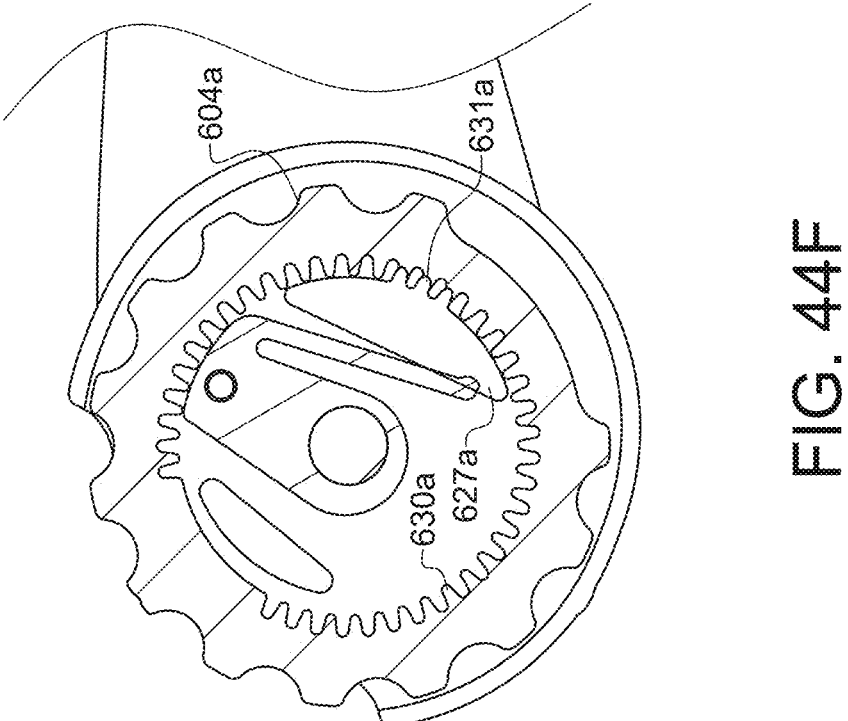
Figure 44H:
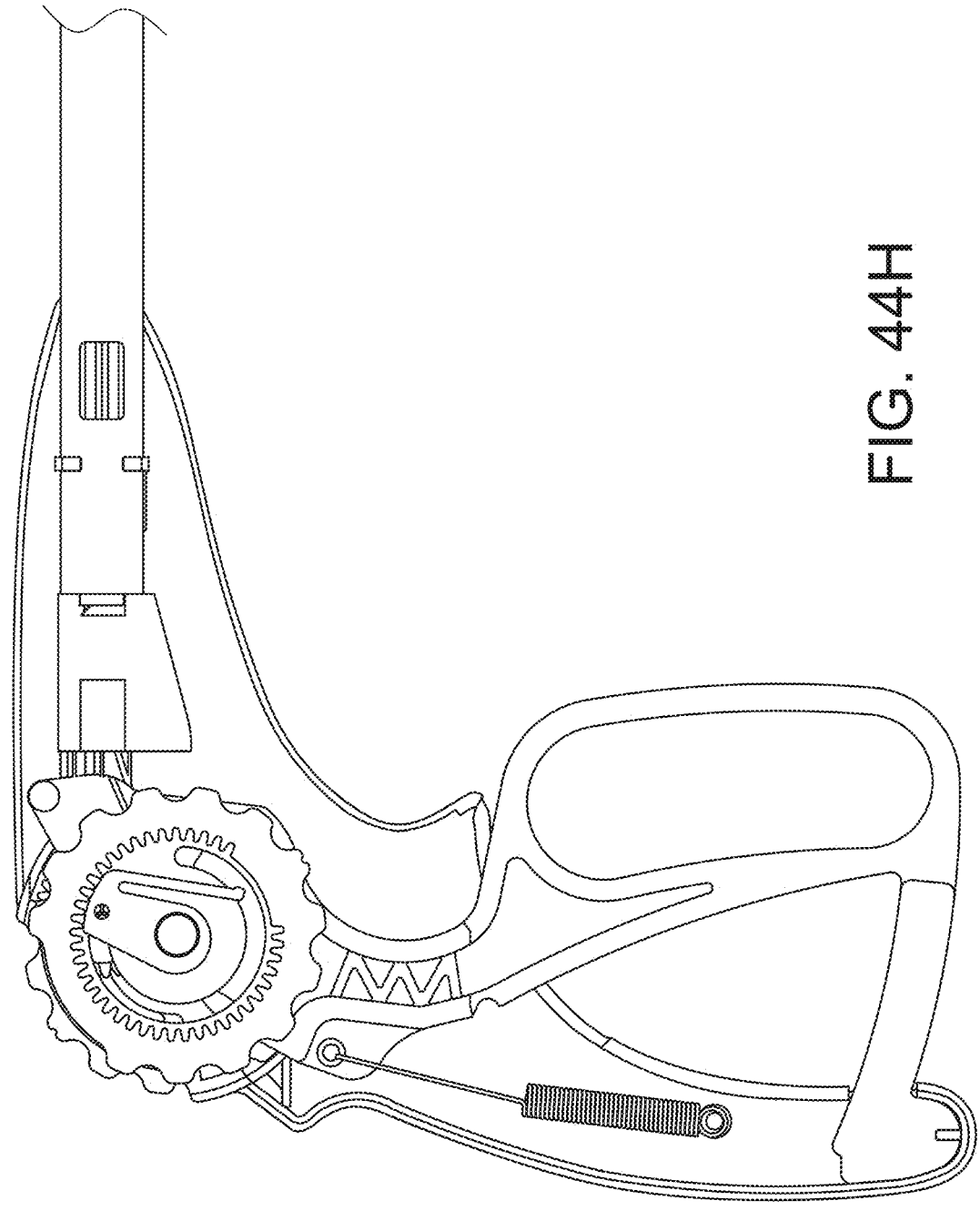

FIGS. 44A to 44H illustrate an alternative embodiment of the first adjustment assembly 602a and a second adjustment assembly 602b. In this embodiment, the first adjustment wheel 604a and the second adjustment wheel 504b are each selectively displaceable relative to the housing portion 202, both linearly and rotatably. The first adjustment wheel 604a of the first adjustment assembly 602a is biased into a first locked position by a first locking member 622a having a first body portion 623a and a first spring portion 624a integrally formed on the first body portion 623a. As illustrated in FIG. 44F, the first spring portion 624a acts on a first ledge portion 627a of the housing portion 202 to bias the first adjustment wheel 604a upwards such that the plurality of teeth 630a of the first adjustment wheel 604a are biased into engagement with a plurality of teeth 631a formed on a lower surface of the first ledge portion 627a.

When it is desired to rotate the first adjustment wheel 604*a* to displace the jaw assembly 403, the user presses a portion of the first adjustment wheel 604*a* to downwardly displace the first adjustment wheel 604*a* into an unlocked position (see FIG. 44D) against the bias of the first spring portion 624*a*. In this unlocked position, the plurality of teeth 630*a* of the first adjustment wheel 604*a* are physically displaced out of engagement with a plurality of teeth 631*a* formed on a lower surface of the first ledge portion 627*a* such that the first adjustment wheel 604*a* can be rotated by a user's thumb. The rotation of the first adjustment wheel 604*a* also rotates a first spur gear 633*a*, and the corresponding first one or more of the control wires 414*a*, 414*b*, 414*c*, 414*d* that may be directly or indirectly coupled to the first spur gear 633*a* are displaced in a manner similar or identical to the manner previously described. To relock the first adjustment assembly 602*a*, the first adjustment wheel 604*a* is released by the user's thumb and the first spring portion 624*a* displaces the first adjustment wheel 604*a* upwards such that the plurality of teeth 630*a* of the first adjustment wheel 604*a* again engage the plurality of teeth 631*a* formed on the lower surface of the first ledge portion 627*a*. The second adjustment assembly 602*b* operates in an identical manner to the first adjustment assembly 602*a*.

Various advantages of the atrial clip assembly and introducer device have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. An atrial clip assembly comprising:
a first arm assembly comprising:
   a first arm body extending along a first arm body axis from a first end to a second end, the first arm body including a first support portion of the first arm body, the first support portion extending from a first end to a second end; and
   a first spine portion extending from a first end to a second end along a first spine axis, and wherein a first portion of the first spine portion extends along a corresponding first portion of the first support portion, wherein the first portion of the first spine portion is disposed within the corresponding first portion of the first support portion; and
   a first suture, wherein a first portion of the first suture is disposed around the first portion of the first spine portion, and wherein a second portion of the first suture extends external to the first support portion; and
a second arm assembly comprising:
   a second arm body extending along a second arm body axis from a first end to a second end, the second arm body including a second support portion of the second arm body, the second support portion extending from a first end to a second end; and
a hinge portion coupling the first end of the first arm body to the first end of the second arm body, wherein the hinge portion is flexible such that the first arm assembly and the second arm assembly are configured to pivot about the hinge portion from a first open position of the atrial clip assembly to a second closed position of the atrial clip assembly.

2. The atrial clip assembly of claim 1, the hinge further comprising:
a base member that extends between the first end of the first arm body and the first end of the second arm body;
a first support protrusion extending from a first portion of the base member and a second support protrusion extending from a second portion, wherein a center gap is formed between a surface of the first support protrusion and a surface of the second support protrusion;
a first engagement protrusion that extends upwards from a third portion of the base member along a first engagement protrusion axis, the first engagement protrusion including
a first inner tab that extends from a first portion the first engagement protrusion in a direction normal to the first engagement protrusion axis,
wherein when the atrial clip assembly is in the first open position, the first inner tab is not disposed within a first portion of the center gap, and when the atrial clip assembly is in the second closed position, the first inner tab is disposed within the first portion of the center gap such that the contact between a surface of the first inner tab and a first portion of the surface of the first support protrusion or a first portion of the surface of the second support protrusion prevents torsional twisting of the hinge portion.

3. The atrial clip assembly of claim 2, the hinge further comprising:
a second engagement protrusion that extends upwards from a fourth portion of the base member along a second engagement protrusion axis, the second engagement protrusion including
a second inner tab that extends from a first portion the second engagement protrusion in a direction normal to the second engagement protrusion axis,
wherein when the atrial clip assembly is in the first open position, the second inner tab is not disposed within a second portion of the center gap, and when the atrial clip assembly is in the second closed position, the second inner tab is disposed within the second portion of the center gap such that the contact between a surface of the second inner tab and a second portion of the surface of the first support protrusion or a second portion of the surface of the second support protrusion prevents torsional twisting of the hinge portion.

4. The atrial clip assembly of claim 1, wherein all or a portion of the hinge portion is a living hinge, and a first end portion of the hinge portion is integrally formed with the first end of the first arm body, and a second end portion of the hinge portion is integrally formed with the first end of the second arm body.

5. The atrial clip assembly of claim 1, wherein:
the first end of the first support portion of the first arm body is at or adjacent to the first end of the first arm body and the second end of the first support portion of the first arm body is at or adjacent to the second end of the first arm body, and

the first end of the second support portion of the second arm body is at or adjacent to the first end of the second arm body, and the second end of the second support portion of the second arm body is at or adjacent to the second end of the second arm body.

6. The atrial clip assembly of claim 1, the second arm assembly further comprising:

a second spine portion extending from a first end to a second end along a second spine axis, and wherein a first portion of the second spine portion extends along a corresponding first portion of the second support portion, wherein the first portion of the second spine portion is disposed within the corresponding first portion of the first support portion; and a second suture, wherein a first portion of the second suture is disposed around the first portion of the second spine portion, and wherein a second portion of the second suture extends external to the second support portion, wherein the second portion of the first suture is configured to be coupled to the second portion of the second suture when the first arm assembly and the second arm assembly are in the second closed position.

7. The atrial clip assembly of claim 6, wherein the second portion of the first suture is configured to be coupled to the second portion of the second suture when the first arm assembly and the second arm assembly are in the second closed position.

8. The atrial clip assembly of claim 1, wherein the first spine portion has a stiffness that is greater than a stiffness of the first arm body.

9. The atrial clip assembly of claim 8, wherein the first spine portion is made of a metal material and the first support portion of the first arm body is made of a plastic material.

10. The atrial clip assembly of claim 1, wherein the first end of the first spine portion is disposed at or adjacent to the first end of the first support portion, and the first portion of the first spine portion is disposed between the first end of the first spine portion and the second end of the first spine portion.

11. The atrial clip assembly of claim 10, wherein the second end of the first spine portion is disposed at or adjacent to the second end of the first support portion.

* * * * *